(12) United States Patent
Takaiwa et al.

(10) Patent No.: US 7,214,851 B2
(45) Date of Patent: May 8, 2007

(54) BZIP TYPE TRANSCRIPTION FACTORS REGULATING THE EXPRESSION OF RICE STORAGE PROTEIN

(75) Inventors: Fumio Takaiwa, Tsuchiura (JP); Yasuyuki Onodera, Koganei (JP)

(73) Assignees: National Institute of Agrobiological Sciences, Ibaraki (JP); National Agriculture and Bio-Oriented Research Organization, Ibaraki (JP)

( * ) Notice: Subject to any disclaimer, the term of this patent is extended or adjusted under 35 U.S.C. 154(b) by 324 days.

(21) Appl. No.: 10/149,553

(22) PCT Filed: Oct. 11, 2001

(86) PCT No.: PCT/JP01/08936

§ 371 (c)(1),
(2), (4) Date: Dec. 19, 2002

(87) PCT Pub. No.: WO02/31154

PCT Pub. Date: Apr. 18, 2002

(65) Prior Publication Data

US 2004/0072159 A1    Apr. 15, 2004

(30) Foreign Application Priority Data

Oct. 11, 2000    (JP)    ............... 2000-311295

(51) Int. Cl.
C12N 15/29    (2006.01)
C12N 15/82    (2006.01)
C12N 5/04    (2006.01)
A01H 1/00    (2006.01)
A01H 5/00    (2006.01)
A01H 5/10    (2006.01)

(52) U.S. Cl. ...................... 800/278; 800/260; 800/286; 435/69.1; 435/320.1; 435/419; 536/23.6; 536/24.1; 536/24.5

(58) Field of Classification Search ............... 536/23.1; 800/295; 435/320.1
See application file for complete search history.

(56) References Cited

FOREIGN PATENT DOCUMENTS

WO    WO 01/83792    11/2001

OTHER PUBLICATIONS

Wu et al. The Plant Journal. 1998. vol. 14(6). p. 673-683.*
Guo et al. PNAS. USA. 2004. vol. 101 (25) p. 9205-9210.*
Kim et al. Nucleic Acids Research. 1990. vol. 18(23). p. 6845-6852.*
Izawa et al. Plant Cell. 1994. vol. 6, p. 1277-12871.*
Lazar et al. Mol. Cell. Biol. 1988. vol. 8(3). p. 1247-1252.*
Whisstock et al. 2003. Quarterly Reviews of Biophysics. 36(3). p. 307-340.*
Izawa et al. J. Mol Biol. 1993. vol. 230. pp. 1131-1144.*
Onodera et al. The Journal of Biological Chemistry 276(17): 14139-14152 (Apr. 2001).*
Izawa et al., "The rice bZIP transcriptional activator RITA-1 is highly expressed during seed development," Plant Cell, 6:1277-1287 [1994] provided to USPTO by WIPO.
Nakase et al., "Characterization of a novel rice bZIP protein which binds to the alpha-globulin promoter," Plant Mol. Biol., 33:513-522 [1997] provided to USPTO by WIPO.
Onodera et al., "A rice functional transcriptional activator, RISBZI, responsible fore endosperm-specific expression of storage protein genes through GCN4 motif," J. Biol. Chem., 276:14139-14152 [2001].
Vincentz et al., "ACGT and vicilin core sequences in a promoter domain required for seed-specific expression of a 2S storage protein gene are recognized by the opaque-2 regulatory protein," Plant Mol. Biol., 34:879-889 [1997] provided to USPTO by WIPO.
Weisshaar et al., "Light-inducible and constitutively expressed DNA-binding proteins recognizing a plant promoter element with functional relevance in light responsiveness," EMBO J., 10:1777-1786 [1991] provided to USPTO by WIPO.
Wu et al., "The GCN4 motif in a rice glutelin gene is essential for endosperm-specific gene expression and is activated by Opaque-2 in transgenic rice plants," Plant J., 14: 673-683 [1998].
Pysh et al., "OHP1: a maize basic domain/leucine zipper protein that interacts with Opaque 2," Plant Cell, 5:227-236, 1993.
Pysh et al., "Characterization of the maize OHP1 gene: evidence of gene copy variability among inbreds," Gene, 177:203-208, 1996.
EMBL Accession No. AJ001265, XP-002315019, Jun. 30, 1998.
EMBL Accession No. AJ001266, XP-002315020, Jun. 30, 1998.
EMBL Accession No. AJ001267, XP-002315021, Jun. 30, 1998.
EMBL Accession No. O82034, XP-002315022, Nov. 1, 1998.

* cited by examiner

Primary Examiner—David T. Fox
(74) Attorney, Agent, or Firm—Medlen & Carroll LLP

(57) ABSTRACT cDNAs (RISBZ1, RISBZ4, and RISBZ5) encoding bZIP transcription factors were isolated from a cDNA library originating in rice plant seed. The cDNAs encode novel proteins and have binding activity to the GCN4 motif. Among them, RISBZ1 activated transcription mediated by the GCN4 motif by 100-fold or more. Since the expression of RISBZ1 precedes the expression of a seed storage protein gene and is expressed only in maturing seeds, it is suggested that RISBZ1 controls the expression of rice seed storage proteins. In addition, by linking the recognition sequence of the transcription factor, the GCN4 motif, in tandem and introducing it into the promoter for a gene encoding seed storage protein to facilitate its binding to the transcription factor RISBZ1, expression of a foreign gene under the control of the modified promoters is greatly enhanced.

18 Claims, 14 Drawing Sheets

Figure 2

```
RISBZ1  1 ...VAVD.IPDG.SAPDP...PV....QPAAAAGVDDVGAVSG.................LLE.....RCPSG.NLE.FLEE.LDGVPAPAASPDGAAIYPS.
RISBZ2  1 ...VES.EE.ISDP.NPDP...PP....QSAAAAQQQGGGGVASG.GGGVAGGGGG....NA.N....RCPSE.VY.QKFL.EL..............AVL.S.
OHP1    1 ...VES.EE.PNDY.VP....HP....QSAAAGAVAAPAGEAA...............L.N....RCPSE.VY.QKF.EE..............AVL.S.
BLZ1    1 ...VES.EE.PDP.SGQD..........SPRQRGRRPPE..............A.N....RCPSE.VY.QKF.EE..............AVL.S.
SPA     1 ..PV.ESL.EA.PEPDSN...PC.....RTSSPPLEA..HMLVA.L...GG.V.A....EVVGGCATNE.AT..C.QKE.VD.PWLLN.......VPTAPVAN.
BLZ2    1 NEPVESLL.EA.PEPDSN...PG.....RTSPPQLQA..HVLA.GVRGAGG.V.V....EIVG.....DGATELC.DKSNE.PSLLN.......VPTEPYAN.
O2-sorg 1 ...VES..E.IL.GD.SDL..SP.P...PE.QQPLVIGTSSVVIDG.VTHGG.NGE..SNM.DQI...QNTT...T.ERL..E.ELLT........DTTPVANS
O2-coix 1 ...V.GM.E.IL.GD.SDL.PSP.PLPLPE.QQPLVTDTGSVVIDG.VTQGGGD.E..GDM.G....QNTT...T.ERL..E.EILIN.......KTTLVTNS
OPAQUE2 1 ...V.IS..E.IL.GP..ELL..P.PAPEPEREQPPVTG...IVV.SVIDVAA.A..DGDM.DQ....QHATE.T.ERL.E.EALTTS...TPPPVVVPNS
RISBZ3  1 .........................................K.....K.PSEL.N.EA.FHGE............RGEDAD
RISBZ4  1 ...................................................ND.EA..IHGG............SGGG.AD
RISBZ5  1 .........................................K......K.PSEL.QL.A.IR.E............AGAG.RK RISBZ1  77 MPAAAAEAAARHSR.YGDRE....AVGVMPHPAA.LP.APAS.AM.PVEYNA.E.RK.DEDEA.T.AAHRAS.GATHSESPLGNKTSLSIVG.ILSSQKCIE
RISBZ2  75 VPNPSPRAEAGGIR.AGGVVP..VDVKQPQLSAA.AA.TTSA.V.DPVEYNA..V.QKLEK.DLAAVAN.RASGTVPPERPG.GSS.LLNADV.HIGAPISIG
OHP1    61 VP......VAGVSR.SVGAG...VEAAERKTPGT.AA.AASSS..V.DPVEYNA.IV.QKLEK.DLAAVA..HRASGAAPPDNSP.GSSLPSVDVPHAGPLKPMG
BLZ1    54 AAD......PSP.S.ASGRG.......QAACRPRGVAGTATGPAV.DPVEYNA.L.QKLEK.DLAAVA.HRASGAMPPERFA.SP.SCPNADGQHIGTINPIG
SPA     80 EAS.TLYPN.PTAE.SRKRPYDVHEMVGPEEVIPT.P.AS...P.V.DPVA.YAM.RRKLDA.LAAVA..L.TT.RGICPQ..SSHDNGASQN..........
BLZ2    78 DAS.TLHPN.PTAEVSRKRRYDVHEEEEVVGVIPT.P.AG...V.V.DP.Y.NA.R.RKLDA.LAAVAM..TT.RGICRQ..SSHDNRASQNP..........
O2-sorg 83 SCP.ALNVD.PVVEVDQGA..........KA.E.VS..AV.GDP.EYNA.I.KRNV.EDI..V.AFK.HRAS.TSGVNSE.GSNNENGGVSS.........
O2-coix 87 SCS.TLNID.PVVEVDQGT..........HA.SGA.VS..AV.GDP.EYNA.IL.KRKLEVD.V.AFK..RAS..SVVNSE.RSQD.NNHNGG.........
OPAQUE2 88 CCSGALNADRPPVMEEAVT..........HA.AAVSSA.V.GDP.EYNA.I.RRKL.ED..AFK.HRAASSWVTSDQRSQG.NNHTGG.SI......
RISBZ3  25 AAA......DQKP.GGPHP.............PP.F.MFSA.DLSSFGFADSVTSTITGVIPNH..INPQSQSLNARHP.VYT..IES.........
RISBZ4  18 AD..............H.............P.LGIFSA.DLSGFGFADS..STITGGIPNH..INPQSQNLNARHP.VSTT.IES.........
RISBZ5  26 PGV.......LS.P.DGAR.............KSGLFSPG.D.GENSVLDQ..ST.DGSGGGHQL.HPESVRTPPRAA.AF.ATADERT.........
```

| | | | | |
|---|---|---|---|---|
| RISBZ1 | SEQ ID NO. 2 | | O2-sorg | SEQ ID NO. 58 |
| RISBZ2 | SEQ ID NO. 53 | | O2-coix | SEQ ID NO. 59 |
| OHP1 | SEQ ID NO. 54 | | OPAQUE2 | SEQ ID NO. 60 |
| BLZ1 | SEQ ID NO. 55 | | RISBZ3 | SEQ ID NO. 61 |
| SPA | SEQ ID NO. 56 | | RISBZ4 | SEQ ID NO. 5 |
| BLZ2 | SEQ ID NO. 57 | | RISBZ5 | SEQ ID NO. 7 |

Figure 3

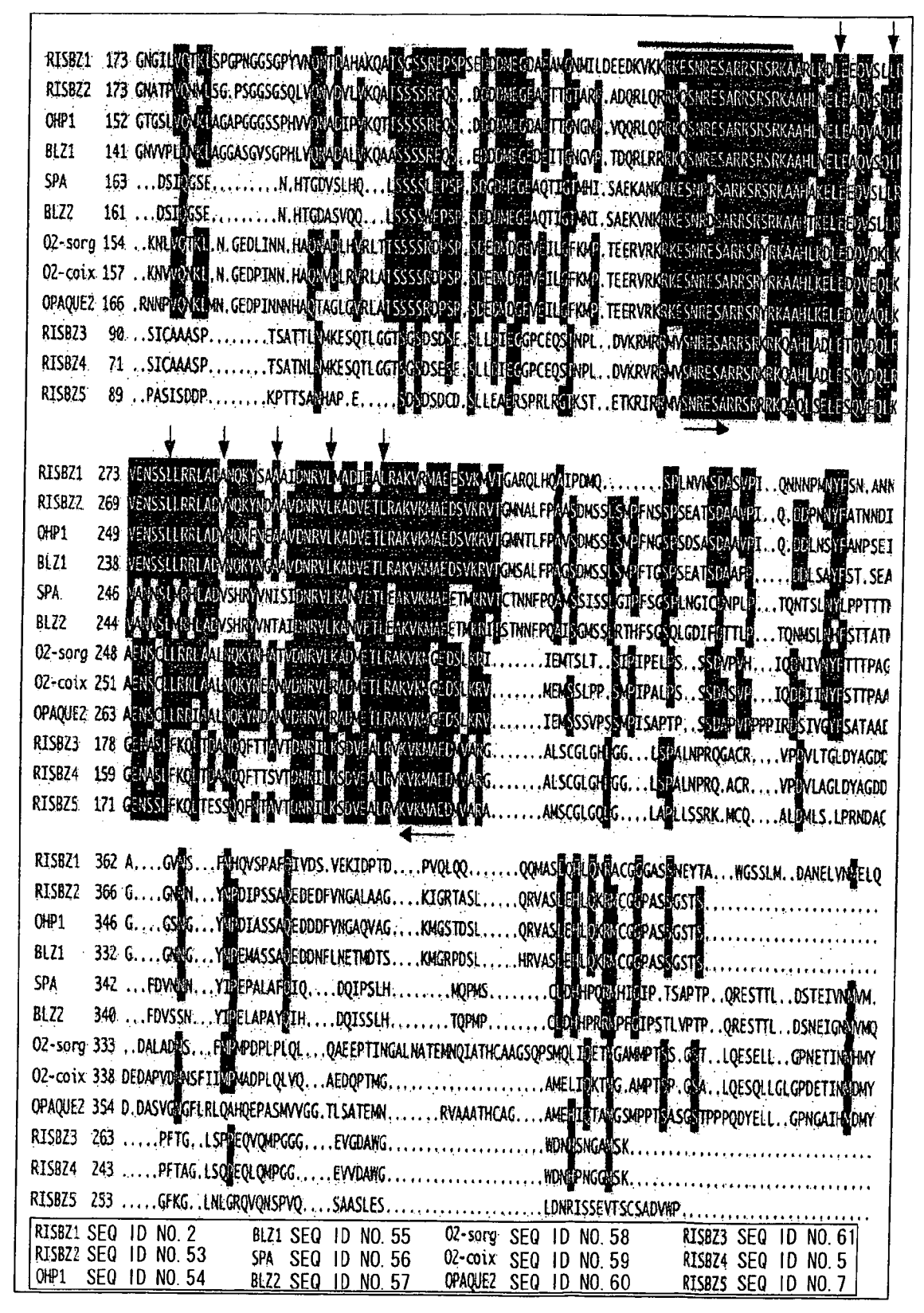

| | | |
|---|---|---|
| RISBZ1 SEQ ID NO. 2 | BLZ1 SEQ ID NO. 55 | 02-sorg SEQ ID NO. 58 | RISBZ3 SEQ ID NO. 61 |
| RISBZ2 SEQ ID NO. 53 | SPA SEQ ID NO. 56 | 02-coix SEQ ID NO. 59 | RISBZ4 SEQ ID NO. 5 |
| OHP1 SEQ ID NO. 54 | BLZ2 SEQ ID NO. 57 | OPAQUE2 SEQ ID NO. 60 | RISBZ5 SEQ ID NO. 7 |

Figure 6
(A)
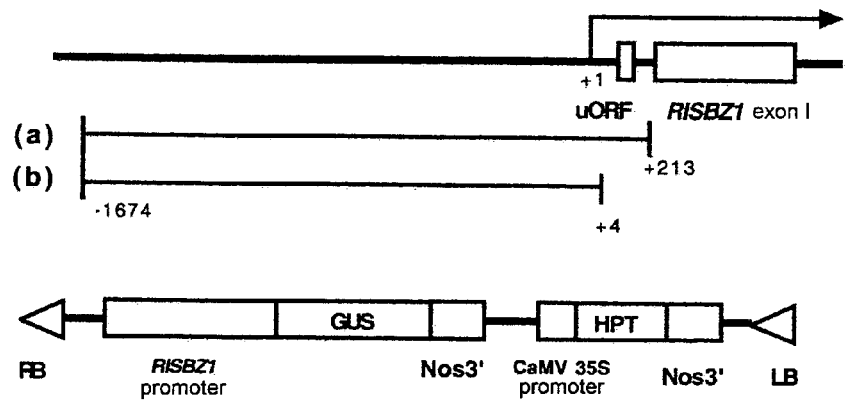
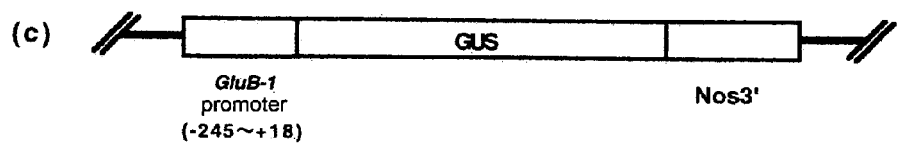
(B)
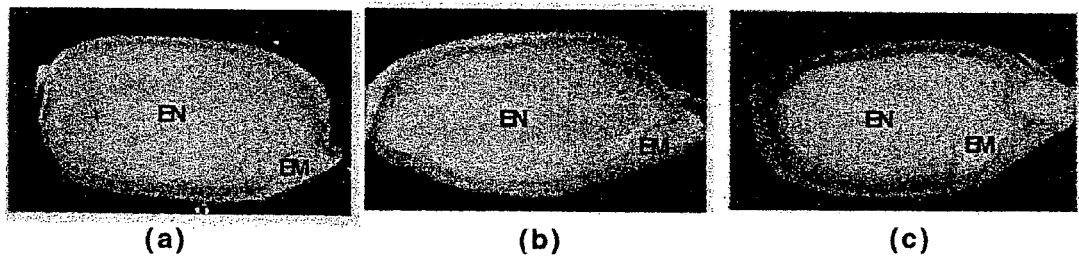
(C)
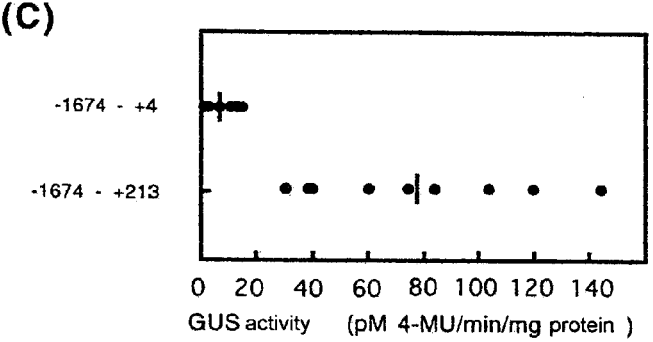

Figure 9
(A)
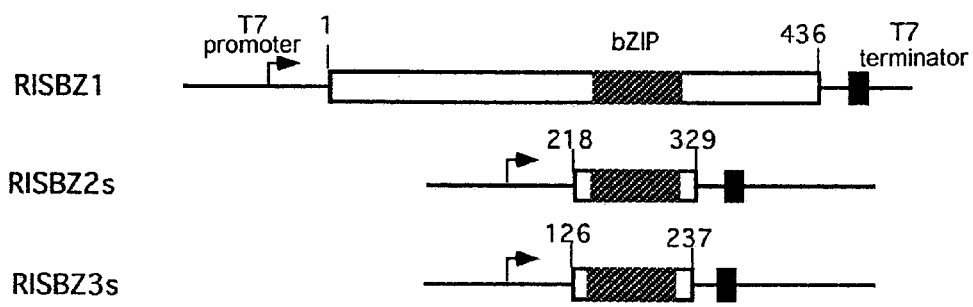
(B)
RISBZ1    − + + −
RISBZ2s   − − + +
RISBZ1    − + + −
RISBZ3s   − − + +
← RISBZ1
← RISBZ1 +RISBZ2s
← RISBZ1
← RISBZ1 +RISBZ3s
← RISBZ2s
← RISBZ3s
Free probe
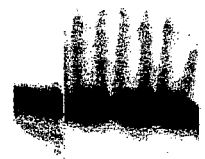
1  2  3  4
Free probe
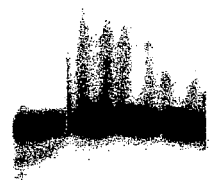
5  6  7  8

| | | |
|---|---|---|
| 4xG | AGCCACGTGGCA | SEQ ID NO. 79 |
| 4xA | ACCTACGTAGGA | SEQ ID NO. 80 |
| 4xC | AGTGACGTCACA | SEQ ID NO. 81 |
| 4xG/C | AGCCACGTCACA | SEQ ID NO. 15 |
| 4xA/G | AGGTACGTGGCA | SEQ ID NO. 82 |
| 4xC/A | ACTGACGTAAGA | SEQ ID NO. 83 |
| 4xGCN4 | GCTGAGTCATGA | SEQ ID NO. 8 |
| 4x22kD | TTCCACGTAGAT | SEQ ID NO. 84 |
| 4xb-32 | GATGACATGGCT | SEQ ID NO. 85 |

| | | |
|---|---|---|
| GCTGAGTCATGA | GluB-1 | SEQ ID NO. 8 |
| CATGAGTCACTT | GluA-1 | SEQ ID NO. 9 |
| AGTGAGTCACTT | GluA-3 | SEQ ID NO. 10 |
| GGTGAGTCATAT | LMWG | SEQ ID NO. 11 |
| GGTGAGTCATGT | Hordein | SEQ ID NO. 12 |
| GATGAGTCATGC | Gliadin | SEQ ID NO. 13 |
| AATGAGTCATCA | Secalin | SEQ ID NO. 14 |

US 7,214,851 B2

BZIP TYPE TRANSCRIPTION FACTORS REGULATING THE EXPRESSION OF RICE STORAGE PROTEIN

TECHNICAL FIELD

The present invention relates to a novel transcription factor and its use pertaining to the endosperm-specific expression of the storage protein in the rice plant seed.

BACKGROUND ART

Seed storage protein is expressed in seeds only during the maturing stage, and the expression of genes encoding this protein is analyzed as a suitable model for investigating the transcription regulatory mechanism of plant genes (Goldberg, R. B. et al., Science 266: 605–614, 1994). The expression of a gene that codes for a seed storage protein is known to be regulated by the cooperation of a plurality of cis factors in a promoter. The binding of a transcription factor to a specific cis regulatory factor is important in the initiation of transcription and the tissue- and time-specific expression. It can be explained that the expression of a seed storage protein is induced by several types of cis regulatory factors relating to the regulation of seed-specific expression when transcription factors that recognize specific cis regulatory factor bind and aggregate. Functional analyses of cis regulatory factors and transcription factors of crop storage protein genes have been conducted in order to elucidate the molecular mechanism of the expression of seed storage proteins (Thomas, T. L., Plant Cell 5: 1401–1410, 1993; Morton, R. L. et al., in Seed Development and Germination, pp. 103–138, Marcel Dekker, Inc., 1995).

However, despite considerable research, analyses using transformed plants failed to identify the cis regulatory factors essential for gene expression regulation in nearly all crops studied, and the gene expression regulatory mechanism has still not been clearly understood. In the case of monocotyledons in particular, the promoter analyses using stable transformed plants has been performed in only the seed storage protein, glutelin, of the rice plants. On the other hand, in the case of maize, wheat and barley, analyses have been conducted using particle guns or tobacco transformants (Muller, M. and Knudsen, S., Plant J. 6:343–355, 1993; Albani, D. et al., Plant Cell 9: 171–184, 1997; Marzabal, P. M. et al., Plant J. 16: 41–52, 1998).

It has been shown that the endosperm-specific expression of the seed storage protein gene of grains is controlled by the collaborative action of several types of cis regulatory factors. The Prolamin box (TGTAAAG), GCN4 motif (TGA(G/C)TCA), AACA motif (AACAAAA), and ACGT motif, which are conserved in the seed storage protein gene promoters of numerous grains, have been characterized as cis regulatory factors involved in endosperm-specific expression by loss-of-function and gain-of-function analyses (Morton, R. L. et al., In: Seed Development and Germination, pp. 103–138, Marcel Dekker Inc., 1995).

The GCN4 motif has been frequently found not only from seed storage protein gene, but also from promoters of genes involved in the metabolism (Muller, M. and Knudsen, S., Plant J. 6: 343–355, 1993). Recently, a polymer of the GCN4 motif of rice plant glutelin gene has been found to reproduce endosperm-specific expression in transformed rice plants, and remarkable decrease in promoter activity and changes in its expression pattern have been found due to the substitution or deletion of nucleotides in the GCN4 motif. These facts prove that the GCN4 motif plays an important role in endosperm-specific expression (Wu, C. Y. et al., Plant J. 14: 673–683, 1998). The GCN4 motif is coupled to a Prolamin box (TGTAAAG) via a plurality of bases in many cases, and is one of the constituents of the two-factor endosperm box found in the prolamin gene promoters of nearly all grains, including wheat glutenin, barley hordein, rye secalin, sorghum cafulin and adlay coixin. The AACA motif is involved in the expression of nearly all rice glutelin genes. Although the combination of two motifs (GCN4 motif and Prolamin box or GCN4 motif and AACA motif) is required for gene expression, in order to adequately function as an endosperm-specific promoter, an additional motif is essential (Takaiwa, F. et al., Plant Mol. Biol. 30: 1207–1221, 1996; Yoshihara, T. et al., FEBS Letts. 383: 213–218, 1996; Wu, C. Y. et al., Plant J. (in press)). Recently, it has been demonstrated that, in order to function as a minimum promoter capable of reproducing endosperm-specific expression in glutelin genes (GluB1) of rice plant, at least three constituents, the GCN4 motif, the AACA motif, and the ACGT motif, present in the −197 bp promoter region, are essential (Wu, C. Y. et al., Plant J. 14: 673–683, 1998; Wu, C. Y. et al., Plant J. 23: 415–421, 2000).

Opaque2 (O2) of maize is an endosperm-specific transcription factor of the bZIP type, and this O2 binds to the ACGT motif in the 22 kDa α-zein gene promoter of maize to activate transcription (Schmidt, R. J. et al., Plant Cell 4: 689–700, 1992). O2 has been reported to be involved in endosperm-specific transcription of b-32 ribosome deactivating protein gene by binding to the (Ga/tTGAPyPuTGPu) sequence (Lohmer, S. et al., EMBO J. 10: 617–624, 1991). O2 is thus considered to have a wide-ranging binding capability. Reportedly, the GCN4 motif is recognized by O2, and transcription is activated through the binding of O2 to the GCN4 motif (Wu, C. Y. et al., Plant J. 14: 673–683, 1998; Holdsworth, M. J. et al., Plant Mol. Biol. 29: 711–720, 1995). In seeds, during the maturing stage, in vivo footprint analysis showed that the nuclear protein binds to the GCN4 motif and Prolamin box present in wheat low molecular weight glutenin gene promoter (Vicente-Carbajos, J. et al., Plant J. 13: 629–640, 1998) and maize γ-zein gene promoter (Marzabal, P. M. et al., Plant J. 16: 41–52, 1998). In addition, the results of an in vitro DNaseI footprint analysis showed that the nuclear protein of maturing rice plant seeds as well as GST-O2 fused protein specifically recognize the GCN4 motif of the rice glutelin gene promoter (Wu, C. Y., et al., Plant J. 14: 673–683, 1998; Kim, S. Y. and Wu, R., Nucl. Acids Res. 18: 6845–6852, 1990). These findings indicate that an O2-like transcription factor is present in grain seeds, and that it controls the endosperm-specific expression of numerous seed storage protein genes mediated by the GCN4 motif.

Recently, cDNA clones of transcription factors that recognize the GCN4 motif have been isolated in wheat (Albani, D. et al., Plant Cell 9: 171–184, 1997) and barley (Vicente-Carbajos, J. et al., Plant J. 13: 629–640, 1998; Onate, L. et al., J. Biol. Chem. 274: 9175–9182, 1999), and have been named SPA, BLZ1 and BLZ2. These transcription factors have been determined to activate the transcription of seed storage protein genes mediated by the GCN4 motif in wheat low molecular weight glutenin and barley B1 hordein gene promoter. Interestingly, these transcription factors were expressed seed-specifically. Although cDNA that codes for a transcription factor having a high homology with the bZIP domain of O2 has previously been isolated from rice plants, it remains to be confirmed whether or not it activates transcription of seed storage protein gene mediated by the GCN4 motif (Izawa, T. et al., Plant Cell 6: 1277–1287, 1994; Nakase, M. et al., Plant Mol. Biol. 33: 513–522, 1997).

DISCLOSURE OF THE INVENTION

An object of the present invention is to provide a novel transcription factor that regulates the expression of rice seed storage protein by binding to the GCN4 motif, a gene that codes for the factor, plant cells and plant bodies in which the gene has been introduced, and a method for production and use thereof.

The present inventors conducted research to resolve the above problems. As mentioned above, the GCN4 motif is a sequence that is highly conserved in the promoters of grain seed storage protein genes, and plays a central role in the endosperm-specific expression of the genes. This GCN4 motif is recognized by the bZIP transcription factor family that is closely related to the Opaque2 (O2) protein of maize. Therefore, the present inventors thought that, by isolating bZIP transcription factor from the rice seeds, it would be possible to identify the transcription factor that binds to the GCN4 motif to control the expression of rice seed storage protein.

First, the present inventors screened a cDNA library originating in rice seed and isolated cDNA that codes for five types of bZIP transcription factors (RISBZ1, RISBZ2, RISBZ3, RISBZ4, and RISBZ5). Based on the homology of the presumed amino acid sequences, RISBZ2 and RISBZ3 were identical to RITA1 (Izawa, T. et al., Plant Cell 6: 1277–1287, 1994) and REB (Nakase, M. et al., Plant Mol. Biol. 33: 513–522, 1997), respectively, and the remaining RISBZ1, RISBZ4; and RISBZ5 were revealed to code for novel proteins. When the binding ability of RISBZ1, RISBZ2, RISBZ3, RISBZ4, and RISBZ5 to GCN4 motif was investigated, they all exhibited binding activity to the GCN4 motif. Furthermore, the transcription activation ability of the five proteins by binding to the GCN4 motif was investigated. As a result, only RISBZ1 activated transcription 100-fold or more by binding to the GCN4 motif. In addition, an analysis using the GAL4 DNA binding domain of yeast revealed that proline-rich, 27 amino acid residues of the N-terminal side of RISBZ1 functioned as a transcription-activating domain. The difference in transcription activation ability between RISBZ1 and the other RISBZ proteins was primarily due to the mutation of 7 amino acid residues (for RISBZ2) or deletion of the transcription-activating domain (for RISBZ3, RISBZ4, and RISBZ5). This finding suggests that the difference in transcription activation ability between RISBZ1 and other RISBZ proteins occur due to a structural mutation of the transcription activating domain. In addition, RISBZ1 was found to form not only a homodimer, but also heterodimers with other RISBZ proteins. Since the expression of RISBZ1 precedes the expression of seed storage protein gene and is expressed only in maturing seeds, RISBZ1 may control the expression of seed storage protein. In order to investigate the expression of RISBZ1 gene, the promoter of the RISBZ1 gene was coupled to a GUS reporter gene, and this construct was introduced into a rice plant. In this rice plant the GUS gene was strongly expressed in the aleurone layer.

As described above, the present inventors demonstrated that the novel proteins RISBZ1, RUSBZ4, and RISBZ5 actually bind to the GCN4 motif, and clarified that RISBZ1 is a transcription activation factor involved in endosperm-specific expression of the rice seed storage protein gene.

The present inventors also produced a transformed plant that contained a DNA construct in which the RISBZ1 of the present invention was connected downstream of a promoter and a DNA construct in which a reporter gene was connected downstream of a promoter containing the target sequence of RISBZ1. The inventors then succeeded in measuring the transcription activity of RISBZ1 in the transformed plant by using the expression of the reporter gene as an indicator. These findings enable high level expression of a useful, highly value-added foreign gene within the transformed plant cells in which the foreign gene is connected downstream of a promoter containing the target sequence of RISBZ1 instead of the above reporter gene.

The present invention relates to a novel transcription factor that regulates the expression of rice seed storage protein by binding to the GCN4 motif, a gene encoding the factor, plant cells and plants in which the gene has been introduced, and methods for production and use thereof. More specifically, the present invention provides the following:

[1] a DNA selected from the following (a) through (d):
  (a) a DNA encoding a protein comprising the amino acid sequence set forth in any one of SEQ ID NOs: 2, 5, and 7;
  (b) a DNA comprising a coding region of the nucleotide sequence set forth in any one of SEQ ID NOs: 1, 3, 4, and 6;
  (c) a DNA comprising the amino acid sequence set forth in any one of SEQ ID NOs: 2, 5, and 7, in which one or more amino acids are substituted, deleted, added, and/or inserted, and encoding a protein that is functionally equivalent to a protein comprising the amino acid sequence set forth in any one of SEQ ID NOs: 2, 5, and 7; and
  (d) a DNA hybridizing under stringent conditions with a DNA comprising the nucleotide sequence set forth in any one of SEQ ID NOs: 1, 3, 4, and 6, and encoding a protein functionally equivalent to a protein comprising the amino acid sequence set forth in any one of SEQ ID NOs: 2, 5, and 7;

[2] the DNA according to [1], which encodes a protein that binds to the GCN4 motif or activates expression of rice seed storage protein;

[3] the DNA according to [1] or [2], which is derived from rice plant;

[4] a DNA encoding antisense RNA complementary to a transcription product of the DNA according to any one of [1] through [3];

[5] a DNA encoding an RNA having ribozyme activity that specifically cleaves a transcription product of the DNA according to any one of [1] through [3];

[6] a DNA encoding an RNA that suppresses the expression of the DNA according to any one of [1] through [3] in plant cells by co-inhibition effects, and having 90% or more homology with the DNA according to any one of [1] through [3];

[7] a DNA encoding a protein having a dominant negative phenotype of a protein encoded by the DNA according to any one of [1] through [3] which is endogenous in plant cells;

[8] a vector containing the DNA according to any one of [1] through [3];

[9] a transformed cell retaining the DNA according to any one of [1] through [3] or the vector according to [8];

[10] a protein that is encoded by the DNA according to any one of [1] through [3];

[11] a method of producing the protein according to [10], the method comprising steps of culturing the transformed cell according to [9] and collecting the expressed protein from said transformed cell or their culture supernatant;

[12] a vector containing the DNA according to any one of [4] through [7];

[13] a transformed plant cell retaining the DNA according to any one of [1] through [7] or the vector according to [8] or [12];

[14] a transformed plant containing the transformed plant cell according to [13];

[15] a transformed plant that is a progeny or clone of the transformed plant according to [14];

[16] a reproductive material of the transformed plant according to [14] or [15];

[17] an antibody that binds to the protein according to [10];

[18] a plant having on its genome a DNA construct in which the DNA according to [1] is operably connected downstream of an expression control region and a DNA construct in which a foreign gene is operably connected downstream of an expression control region having the target sequence of the protein according to [10];

[19] the plant according to [18], wherein the target sequence is a sequence containing the GCN4 motif;

[20] the plant according to [19], wherein the GCN4 motif has the sequence set forth in any one of SEQ ID NOs: 8, 13, and 14;

[21] the plant according to [18], wherein the target sequence is a sequence containing a G/C box; and,

[22] a method of producing the plant according to any one of [18] through [21], the method comprising a step of crossing a plant having on its genome a DNA construct in which the DNA according to [1] is operably connected downstream of an expression control region, with a plant having on its genome a DNA construct in which a foreign gene is operably connected downstream of an expression control region containing the target sequence of the protein according to [10].

The present invention provides DNAs encoding RISBZ1, RISBZ4, and RISBZ5 protein originating in the rice plant. The nucleotide sequence of the cDNA of RISBZ1 is shown in SEQ ID NO: 1, the amino acid sequence of the protein encoded by the cDNA is shown in SEQ ID NO: 2, and the nucleotide sequence of the genome DNA is shown in SEQ ID NO: 3 (the genome DNA sequence set forth in SEQ ID NO: 3 contains introns and is composed of six exons). The nucleotide sequences of the cDNAs of RISBZ4 and RISBZ5 proteins are shown in SEQ ID NO: 4 and 6, respectively, while the amino acid sequences of the proteins encoded by the cDNAs of RISBZ4 and RISBZ5 proteins are shown in SEQ ID NO: 5 and 7, respectively. In the present specification, the RISBZ1, RISBZ4, and RISBZ5 of the present invention are collectively referred to as RISBZ.

The RISBZ proteins of the present invention are thought to be bZIP transcription factors having the ability to bind the GCN4 motif. Among these, RISBZ1 remarkably activates transcription by binding to the GCN4 motif. Since the promoter of the RISBZ1 gene is activated in the aleurone layer of rice seeds, RISBZ1 is thought to be a transcription-activating factor that controls the expression of rice seed storage protein.

In addition, it has been reported that bZIP transcription factors form various homo/heterodimers through the combination of various factors belonging to the bZIP transcription factor family. As a result, control factors with various functions are formed, which control gene transcription. In the Examples described below, RISBZ2 and RISBZ3 were shown to form a heterodimer with RISBZ1. In addition, RISBZ4 and RISBZ5 have extremely high homology (96% and 82.7%, respectively) with the bZIP domain of RISBZ3, and these factors would also form heterodimers with RISBZ1. These facts suggest that RISBZ4 and RISBZ5 of the present invention would form, with the RISBZ1 and other RISBZ members of the present invention, heterodimers having various transcription activating abilities and DNA binding properties depending on the maturation stage and tissue to control the expression of seed storage protein.

Thus, the DNA encoding the RISBZ protein of the present invention, or a molecule that controls the expression of the DNA, would be useful in, for example, regulating the expression of seed storage protein. Regulation of the expression of seed storage protein has various industrial advantages. For example, it would be possible to accumulate abundant foreign gene products in the endosperm by deleting seed storage protein in the endosperm. On the other hand, by highly accumulating seed storage protein in the endosperm, it would be possible to produce seeds (e.g., rice) having greater nutritional value.

The DNA encoding the RISBZ protein of the present invention includes genomic DNA, cDNA, and chemically synthesized DNA. A genomic DNA and cDNA can be prepared according to conventional methods known to those skilled in the art. More specifically, a genomic DNA can be prepared, for example, as follows: (1) extracting genomic DNA from plant cells or tissues; (2) constructing a genomic library (utilizing a vector, such as plasmid, phage, cosmid, BAC, PAC, and so on); (3) spreading the library; and (4) conducting colony hybridization or plaque hybridization using a probe prepared based on the DNA encoding the protein of the present invention (e.g. SEQ ID NO: 1, 3, 4, or 6). Alternatively, a genomic DNA can be prepared by PCR, using primers specific to the DNA encoding the protein of the present invention (e.g. SEQ ID NO: 1, 3, 4, or 6). On the other hand, cDNA can be prepared, for example, as follows: (1) synthesizing cDNAs based on mRNAs extracted from plant cells or tissues; (2) preparing a cDNA library by inserting the synthesized cDNA into vectors, such as λZAP; (3) spreading the cDNA library; and (4) conducting colony hybridization or plaque hybridization as described above. Alternatively, cDNA can also be prepared by PCR.

The present invention includes DNAs encoding proteins functionally equivalent to the RISBZ protein of SEQ ID NO: 2, 5, or 7. Herein, the term "functionally equivalent to the RISBZ protein" means that the object protein has the biological function equivalent to those of RISBZ protein of SEQ ID NO: 2, 5, or 7, such as the function of binding to GCN4 motif and/or regulating the expression of rice seed storage proteins. The rice seed storage proteins include, for example, rice glutelins.

Examples of such DNAs include those encoding mutants, derivatives, alleles, variants, and homologues comprising the amino acid sequence of. SEQ ID NO: 2, 5, or 7 wherein one or more amino acids are substituted, deleted, added, and/or inserted.

Examples of methods for preparing a DNA encoding a protein comprising altered amino acids well known to those skilled in the art include the site-directed mutagenesis (Kramer, W. and Fritz, H. -J., Oligonucleotide-directed construction of mutagenesis via gapped duplex DNA. Methods in Enzymology, 154: 350–367, 1987). The amino acid sequence of a protein may also be mutated spontaneously due to the mutation of a nucleotide sequence. A DNA encoding proteins having the amino acid sequence of a natural RISBZ protein (SEQ ID NOs: 2, 5, or 7) wherein one or more amino acids are substituted, deleted, and/or added are also included in the DNA of the present invention, so long as they encode a protein functionally equivalent to the natural RISBZ protein. Additionally, nucleotide sequence mutants that do not give rise to amino acid sequence changes in the protein (degeneracy mutants) are also included in the DNA of the present invention. The numbers of nucleotide mutations in the object DNA at amino acid level is typically 100 amino acids or less, preferably 50 amino acids or less, more preferably 20 amino acids or less, and most preferably 10 amino acids or less (for example, amino acids or less or 3 amino acids or less).

Whether or not a certain DNA codes for a protein having the function of binding to the GCN4 motif can be determined by, for example, gel shift assay usually used by those skilled in the art. More specifically, this assay can be carried out as follows: First, the detected DNA is incorporated into a vector so that its gene product forms a fused protein with GST and the vector is allowed to express the fused protein. The expression product is purified using GST as an indicator followed by mixing with a labeled DNA probe containing the GCN4 motif. This mixed solution is analyzed by electrophoresis using nondenaturing acrylamide gel. Binding activity can then be evaluated based on the locations of the detected bands on the gel.

In addition, whether or not a certain DNA codes for a protein having the function of activating expression of rice seed storage protein can be determined by, for example, a reporter assay. More specifically, this assay can be carried out as follows. First, a vector is constructed so that a reporter gene is connected to and downstream of the promoter of rice seed storage protein. This vector and a vector that expresses the gene product of a test DNA are introduced into the cells for the reporter assay, and the transcription activity of the test DNA gene product is evaluated by measuring the activity of the reporter gene product. An example of the promoter of rice seed storage protein that can be used for the reporter assay is the rice glutelin gene promoter. There are no particular restrictions to the reporter gene provided its expression can be detected, and any reporter gene that are usually used in various assay systems by those skilled in the art, can be used. A preferable example of the reporter gene is the β-glucuronidase (GUS) gene.

A DNA encoding a protein functionally equivalent to the RISBZ protein set forth in SEQ ID NO: 2, 5, or 7 can be produced by, for example, methods well known to those skilled in the art including: methods using hybridization techniques (Southern, E. M., Journal of Molecular Biology, Vol. 98, 503, 1975); and polymerase chain reaction (PCR) techniques (Saiki, R. K. et al. Science, 230, 1350–1354, 1985; Saiki, R. K. et al. Science, 239, 487–491, 1988). It is routine for a person skilled in the art to isolate a DNA with high homology to the RISBZ gene from rice and so forth using the RISBZ gene (SEQ ID NO: 1, 3, 4, or 6) or parts thereof as a probe, and oligonucleotides hybridizing specifically to the gene as a primer. Such a DNA encoding a protein functionally equivalent to the RISBZ protein, isolable by hybridization techniques or PCR techniques, is included in the DNA of this invention.

Hybridization reactions to isolate such DNAs are preferably conducted under stringent conditions. Stringent hybridization conditions of the present invention include conditions such as: 6 M urea, 0.4% SDS, and 0.5×SSC; and those which yield a similar stringency to the conditions. DNAs with higher homology are expected to be isolated efficiently when hybridization is performed under conditions with higher stringency, for example, 6 M urea, 0.4% SDS, and 0.1×SSC. These DNAs isolated under such conditions are expected to encode a protein having a high amino acid level homology with RISBZ protein (SEQ ID NO: 2, 5, or 7). Herein, high homology means an identity of at least 50% or more, more preferably means an identity of at least 70% or more, and most preferably means an identity of at least 90% or more (e.g., 95% or more) throughout the entire amino acid sequence. The degree of sequence identity can be determined by FASTA search (Pearson W. R. and D. J. Lipman Proc. Natl. Acad. Sci. USA. 85:2444–2448, 1988) or BLAST search.

The DNA of the present invention can be used, for example, to prepare recombinant proteins and to produce transgenic plants as described above.

A recombinant protein is usually prepared by inserting a DNA encoding a protein of the present invention into an appropriate expression vector, introducing the vector into an appropriate cell, culturing the transformed cells, and purifying expressed proteins. A recombinant protein can be expressed as a fusion protein with other proteins so as to be easily purified, for example, as a fusion protein with maltose binding protein in *Escherichia coli* (New England Biolabs, USA, vector pMAL series), as a fusion protein with glutathione-S-transferase (GST) (Amersham Pharmacia Biotech, vector pGEX series), or tagged with histidine (Novagen, pET series). The host cell is not limited so long as the cell is suitable for expressing the recombinant protein. It is possible to utilize, for example, yeast, plant, insect cells or various other animal cells besides the above-described *E. coli*. A vector can be introduced into a host cell by a variety of methods known to one skilled in the art. For example, a transformation method using calcium ions (Mandel, M. and Higa, A. Journal of Molecular Biology, 53, 158–162,1970; Hanahan, D. Journal of Molecular Biology, 166, 557–580, 1983) can be used to introduce a vector into *E. coli*. A recombinant protein expressed in the host cells can be purified and recovered from the host cells or the culture supernatant thereof by known methods in the art. When a recombinant protein is expressed as a fusion protein with maltose binding protein or other partners, the recombinant protein can be easily purified via affinity chromatography.

The resulting protein can be used to prepare an antibody that binds to the protein. For example, a polyclonal antibody can be prepared by immunizing immune animals, such as rabbits, with a purified protein of the present invention or its portion, collecting blood after a certain period, and removing clots. A monoclonal antibody can be prepared by fusing myeloma cells with the antibody-forming cells of animals immunized with the above protein or its portion, isolating a monoclonal cell expressing a desired antibody (hybridoma), and recovering the antibody from the cell. The antibody thus obtained can be utilized to purify or detect a protein of the present invention. Accordingly, the present invention includes antibodies that bind to proteins of the invention.

A plant transformant expressing DNAs of the present invention can be created by inserting a DNA encoding a protein of the present invention into an appropriate vector, introducing this vector into a plant cell, and then, regenerating the resulting transformed plant cell.

On the other hand, a plant transformant in which the expression of the DNA of the present invention is suppressed can be created using a DNA that suppresses the expression of a DNA encoding a protein of the present invention: wherein the DNA is inserted into an appropriate vector, the vector is introduced into a plant cell, and then, the resulting transformed plant cell is regenerated. The phrase "suppression of expression of a DNA encoding a protein of the present invention" includes suppression of gene transcription as well as suppression of translation to protein. Furthermore, it also includes the complete inability of expression of DNA as well as reduction of expression.

The expression of a specific endogenous gene in plants can be suppressed by methods utilizing antisense technology conventional to the art. Ecker et al. were the first to demonstrate the antisense effect of an antisense RNA introduced by electroporation into plant cells by using the transient gene expression method (J. R. Ecker and R. W. Davis Proc. Natl. Acad. Sci. USA 83: 5372, 1986). Thereafter, the target gene expression was reportedly reduced in tobacco and petunias by expressing antisense RNAs (A. R. van der Krol et al. Nature 333: 866, 1988). The antisense technique has now been established as a means of suppressing target-gene expression in plants.

Multiple factors cause antisense nucleic acid to suppress the target-gene expression. These include the following: inhibition of transcription initiation by triple strand formation; suppression of transcription by hybrid formation at the site where the RNA polymerase has formed a local open loop structure; transcription inhibition by hybrid formation with the RNA being synthesized; suppression of splicing by hybrid formation at the junction between an intron and an exon; suppression of splicing by hybrid formation at the site of spliceosome formation; suppression of mRNA translocation from the nucleus to the cytoplasm by hybrid formation with mRNA; suppression of splicing by hybrid formation at the capping site or at the poly(A) addition site; suppression of translation initiation by hybrid formation at the binding site for the translation initiation factors; suppression of translation by hybrid formation at the site for ribosome binding near the initiation codon; inhibition of peptide chain elongation by hybrid formation in the translated region or at the polysome binding sites of mRNA; and suppression of gene expression by hybrid formation at the sites of interaction between nucleic acids and proteins. These factors suppress the target gene expression by inhibiting the process of transcription, splicing, or translation (Hirashima and Inoue, "Shin Seikagaku Jikken Koza (New Biochemistry Experimentation Lectures) 2, Kakusan (Nucleic Acids) IV, Idenshi No Fukusei To Hatsugen (Replication and Expression of Genes)," Nihon Seikagakukai Hen (The Japanese Biochemical Society), Tokyo Kagaku Dozin, pp. 319–347, (1993)).

An antisense sequence of the present invention can suppress the target gene expression by any of the above mechanisms. In one embodiment, if an antisense sequence is designed to be complementary to the untranslated region near the 5' end of the gene's mRNA, it will effectively inhibit translation of a gene. It is also possible to use sequences complementary to the coding regions or to the untranslated region on the 3' side. Thus, the antisense DNA used in the present invention includes a DNA having antisense sequences against both the untranslated regions and the translated regions of the gene. The antisense DNA to be used is connected downstream of an appropriate promoter, and, preferably, a sequence containing the transcription termination signal is connected on the 3' side. The DNA thus prepared can be transfected into the desired plant by known methods. The sequence of the antisense DNA is preferably a sequence complementary to the endogenous gene of the plant to be transformed or a part thereof, but it need not be perfectly complementary so long as it can effectively inhibit the gene expression. The transcribed RNA is preferably 90% or more, and most preferably 95% or more complementary to the transcribed products of the target gene. The complementary of sequences can be determined by the above-described search methods. In order to effectively inhibit the expression of the target gene by means of an antisense sequence, the antisense DNA should be at least 15 nucleotides long or more, preferably 100 nucleotides long or more, and still more preferably 500 nucleotides long or more. The antisense DNA to be used is generally shorter than 5 kb, and preferably shorter than 2.5 kb.

DNA encoding ribozymes can also be used to suppress the expression of endogenous genes. A ribozyme means an RNA molecule that has catalytic activities. There are many ribozymes having various activities. Research on the ribozymes as RNA cleaving enzyme has enabled the design of a ribozyme that site-specifically cleaves RNA. While some ribozymes of the group I intron type or the M1RNA contained in RNaseP consist of 400 nucleotides or more, others belonging to the hammerhead type or the hairpin type have an activity domain of about 40 nucleotides (Makoto Koizumi and Eiko Ohtsuka Tanpakushitsu Kakusan Kohso (Nucleic acid, Protein, and Enzyme) 35: 2191, 1990).

The self-cleavage domain of a hammerhead type ribozyme cleaves at the 3' side of C15 of the sequence G13U14C15. Formation of a nucleotide pair between U14 and A at the ninth position is considered important for the ribozyme activity. It has been shown that the cleavage also occurs when the nucleotide at the 15th position is A or U instead of C (M. Koizumi et al. FEBS Lett. 228: 225, 1988). If the substrate binding site of the ribozyme is designed to be complementary to the RNA sequences adjacent to the target site, one can create a restriction-enzyme-like RNA cleaving ribozyme which recognizes the sequence UC, UU, or UA within the target RNA (M. Koizumi et al. FEBS Lett. 239: 285, 1988; Makoto Koizumi and Eiko Ohtsuka Tanpakushitsu Kakusan Kohso (Protein, Nucleic acid, and Enzyme), 35: 2191, 1990; M. Koizumi et al. Nucleic Acids Res. 17: 7059, 1989). For example, in the coding region of the RISBZ gene (SEQ ID NO: 1, 3, 4, or 6), there are pluralities of sites that can be used as the ribozyme target.

The hairpin-type ribozyme is also useful in the present invention. A hairpin-type ribozyme can be found, for example, in the minus strand of the satellite RNA of tobacco ringspot virus (J. M. Buzayan, Nature 323: 349,1986). This ribozyme has also been shown to target-specifically cleave RNA (Y. Kikuchi and N. Sasaki (1992) Nucleic Acids Res. 19: 6751; Yo Kikuchi (1992) Kagaku To Seibutsu (Chemistry and Biology) 30: 112).

The ribozyme designed to cleave the target is fused with a promoter, such as the cauliflower mosaic virus $^{35}$S promoter, and with a transcription termination sequence, so that it will be transcribed in plant cells. If extra sequences have been added to the 5' end or the 3' end of the transcribed RNA, the ribozyme activity can be lost. In this case, one can place an additional trimming ribozyme, which functions in cis to perform the trimming on the 5' or the 3' side of the ribozyme portion, in order to precisely cut the ribozyme portion from the transcribed RNA containing the ribozyme (K. Taira et al. (1990) Protein Eng. 3: 733; A. M. Dzaianott and J. J. Bujarski (1989) Proc. Natl. Acad. Sci. USA 86: 4823; C. A. Grosshands and R. T. Cech (1991) Nucleic Acids Res. 19: 3875; K. Taira et al. (1991) Nucleic Acid Res. 19: 5125). Multiple sites within the target gene can be cleaved by arranging these structural units in tandem to achieve greater effects (N. Yuyama et al., Biochem. Biophys. Res. Commun. 186: 1271 (1992)). By using such ribozymes, it is possible to specifically cleave the transcription products of the target gene in the present invention, thereby suppressing the expression of the gene.

Endogenous gene expression can also be suppressed by co-suppression through the transformation by DNA having a sequence identical or similar to the target gene sequence. "Co-suppression" refers to the phenomenon in which, when a gene having a sequence identical or similar to the target endogenous gene sequence is introduced into plants by transformation, expression of both the introduced exogenous gene and the target endogenous gene becomes suppressed. Although the detailed mechanism of co-suppression is unknown, it is frequently observed in plants (Curr. Biol. 7: R793, 1997, Curr. Biol. 6: 810, 1996). For example, if one wishes to obtain a plant body in which the RISBZ gene is co-suppressed, the plant in question can be transformed via a vector DNA designed so as to express the RISBZ gene or DNA having a similar sequence to select a plant having the RISBZ mutant character, for example, a plant with modified expression level of storage proteins in seeds, among the resultant plants. The gene to be used for co-suppression need not be identical to the target gene, but it should have at least 70% or more sequence identity, preferably 80% or more sequence identity, and more preferably 90% or more (e.g., 95% or more) sequence identity. Sequence identity can be determined by using the above-described search.

In addition, endogenous gene expression in the present invention can also be suppressed by transforming the plant with a gene encoding a protein having the dominant negative phenotype of the expression product of the target gene. "A DNA encoding a protein having the dominant negative phenotype" as used herein means a DNA encoding a protein, which upon expression, can eliminate or reduce the activity of the protein encoded by endogenous gene inherent to the plant. An example thereof is a DNA that codes for a peptide having GCN4 binding ability and having no transcription activating domain of the protein of the present invention (for example, the peptide missing the 1st to 40th amino acids of the amino acid sequence of SEQ ID NO: 2 or a peptide of other proteins corresponding thereto).

The vector used to transform plant cells is not particularly restricted as long as it is capable of expressing an inserted gene in the cells. For example, a vector having a promoter for performing constitutive gene expression in plant cells (e.g., the $^{35}$S promoter of cauliflower mosaic virus), or a vector having a promoter that is inductively activated by an external stimulus can be used. In addition, a promoter that guarantees tissue-specific expression can also be suitably used. Examples of tissue-specific promoters include a promoter of glutelin gene (Takaiwa, F. et al., Plant Mol. Biol. 17: 875–885, 1991) or a promoter of the RISBZ1 of the present invention for the expression in the seeds of rice plants, and a promoter of glycinin gene for the expression in the seeds of leguminous crops such as kidney beans, broad beans and green peas or oil seed crops such as peanuts, sesame seeds, rape seeds, cottonseeds, sunflower seeds and safflower seeds, or a promoter of the major storage protein of each of the above crops such as a promoter of phaseolin gene in the case of kidney beans (Murai, N. et al., Science 222: 476–482, 1993) or a promoter of the gluciferrin gene in the case of rape seed (Rodin, J. et al., Plant Mol. Biol. 20: 559–563, 1992), a promoter of the patatin gene (Rocha-Sosa, M. et al., EMBO J. 8: 23–29, 1989) for the expression in the root tuber of potatoes, a promoter of the sporamin gene for the expression in the root tuber of sweet potatoes (Hattori, T. and Nakamura, K., Plant Mol. Biol. 11: 417–426, 1988), and a promoter of the ribulose-1,5-bisphosphate decarboxylase gene for the expression in the leaves of spinach and other vegetables (Orozco, B. M. and Ogren, W. L., Plant Mol. Biol. 23: 1129–1138, 1993).

The plant cell to which a vector is introduced used herein includes various forms of plant cells, such as cultured cell suspensions, protoplasts, leaf sections, and callus.

A vector can be introduced into plant cells by known methods, such as the polyethylene glycol method, electroporation, *Agrobacterium*-mediated transfer, and particle bombardment. Plants can be regenerated from transformed plant cells by known methods depending on the type of the plant cell (Toki et al., (1995) Plant Physiol. 100:1503–1507). For example, transformation and regeneration methods for rice plants include: (1) introducing genes into protoplasts using polyethylene glycol and regenerating the plant body (suitable for *indica* rice cultivars) (Datta, S. K. (1995) in "Gene Transfer To Plants", Potrykus I and Spangenberg Eds., pp66–74); (2) introducing genes into protoplasts using electric pulse, and regenerating the plant body (suitable for *japonica* rice cultivars)(Toki et al (1992) Plant Physiol. 100, 1503–1507); (3) introducing genes directly into cells by the particle bombardment, and regenerating the plant body (Christou et al. (1991) Bio/Technology, 9: 957–962); (4) introducing genes using *Agrobacterium*, and regenerating the plant body (Hiei et al. (1994) Plant J. 6: 271–282); and so on. These methods are already established in the art and are widely used in the technical field of the present invention. Such methods can be suitably used for the present invention.

Once a transformed plant with the DNA of the present invention integrated into the genome is obtained, it is possible to gain progenies from that plant body by sexual or vegetative propagation. Alternatively, plants can be mass-produced from breeding materials (for example, seeds, fruits, ears, tubers, tubercles, tubs, callus, protoplast, etc.) obtained from the plant, as well as progenies or clones thereof. Plant cells transformed with the DNA of the present invention, plant bodies including these cells, progenies and clones of the plant, as well as breeding materials obtained from the plant, its progenies and clones, are all included in the present invention. The plant body of the present invention is preferably a monocotyledon, more preferably a plant of the Poaceae, and most preferably a rice plant.

In addition, the present invention provides a plant body in which a foreign gene product has been highly expressed using the RISBZ gene of the present invention. The plant body of the present invention has in its genome a DNA construct in which the DNA of the present invention is operably connected downstream of an expression control region, and a DNA construct in which a foreign gene is operably connected downstream of an expression control region having a target sequence.

The DNA of the present invention or a foreign gene being "operably connected" downstream of an expression control region means that the DNA of the present invention or a foreign gene binds to an expression control region so as to induce the expression of the DNA of the present invention or a foreign gene by the binding of a transcription factor to the expression control region.

The target sequence refers to a DNA sequence to which the RISBZ protein of the present invention, which is a transcription factor, binds, and is preferably a DNA sequence that contains the GCN4 motif or G/C box. Examples of the GCN4 motif include the sequences shown below which have been found in various genes:

* GCN4 Motif (name of gene containing GCN4 motif)

```
GCTGAGTCATGA/(GluB-1)      SEQ ID NO: 8
CATGAGTCACTT/(GluA-1)      SEQ ID NO: 9
AGTGAGTCACTT/(GluA-3)      SEQ ID NO: 10
GGTGAGTCATAT/(LMWG)        SEQ ID NO: 11
GGTGAGTCATGT/(Hordein)     SEQ ID NO: 12
GATGAGTCATGC/(Gliadin)     SEQ ID NO: 13
AATGAGTCATCA/(Secalin).    SEQ ID NO: 14
```

Preferable GCN4 motif sequences for use as target sequences include "GCTGAGTCATGA/SEQ ID NO: 8", GATGAGTCATGC/SEQ ID NO: 13" and "AATGAGTCATCA/SEQ ID NO: 14". Specific examples of a G/C box include the sequence, "AGCCACGTCACA/SEQ ID NO: 15". Sequences in which the above GCN4 motif or G/C box is repeated in tandem are also included in the target sequence of the present invention, and a preferable example is a sequence in which the GCN4 motif or G/C box are repeated in tandem four times.

Examples of foreign genes include genes coding for antibodies, enzymes, and physiologically active peptides.

Moreover, the present invention provides a method of producing a plant body in which a foreign gene product is highly expressed using the RISBZ gene of the present invention. Examples of the methods for producing the plant body include a method of crossing "a plant body having a DNA construct in its genome, in which the DNA of the present invention is operably connected downstream of an expression control region," and "a plant body having a DNA construct in its genome, in which a foreign gene is operably connected downstream of an expression control region having the target sequence of the protein of the present invention."

The above-described "DNA construct in which the DNA of the present invention is operably connected downstream of an expression control region," and "the DNA construct in which a foreign gene is operably connected downstream of an expression control region having a target sequence" can be introduced into the plant genome by a conventional method by those skilled in the art, such as a method that uses the above-mentioned *agrobacterium*.

In addition, crossing of plant bodies can be carried out by a conventional method for those skilled in the art. For example, in order to prevent self-propagation, only the pollen is sterilized by demasculating using the tip shearing method on the day of crossing or by demasculating using hot water on the day of crossing to shake pollinate the ear of the pollen mother.

BRIEF DESCRIPTION OF THE DRAWINGS

FIG. 2 compares the amino acid sequences of RISBZ protein and O2-like bZIP protein. Outline letters on a black background shows the amino acids that retained 50% or more. The presumed nuclear migration signal (NLSA: SV40-like motif) (Varagona, M. J. et al., Plant Cell 4: 1213–1227, 1992) and the serine-rich phosphorylation sites are indicated with double lines and broken lines, respectively. The bold lines indicate the basic domain, which has a two-factor nuclear migration signal (NLSB) structure. Downward arrows indicate the leucine repeats. The primer used for the production of the rice bZIP probe was designed based on the amino acid sequences indicated by rightward and leftward arrows. BLZ1 (Vicente-Carbojos, J. et al., Plant J. 13: 629–640, 1998) and BLZ2 (Onate, L. et al., J. Biol. Chem. 274: 9175–9182, 1999) represent O2-like bZIP proteins isolated from barley, O2 (Hartings, H. et al., EMBO J. 8: 2795–2801, 1989) and OHP1 (Pysh, L. D. et al., Plant Cell 5: 227–236, 1993) from maize, SPA from wheat (Albani D. et al., Plant Cell9: 171–184, 1997), O2-sorg from sorghum (Pirovano, L. et al., Plant Mol. Biol. 24: 515–523, 1994), and O2-coix from adlay (Vettore, A. L. et al., Plant Mol. Biol. 36: 249–263, 1998).

FIG. 3 is a continuation of FIG. 2.

FIG. 6 represents the results of histological analysis of the RISBZ1 promoter/GUS reporter gene in a transformed rice plant.

(A) is a schematic drawing of the RISBZ1 promoter/GUS reporter gene. (a) and (b) show the sequence from the $-1674^{th}$ to $+4^{th}$ nucleotides counting from the transcription initiation point of the RISBZ1 gene and the sequence from the $-1674^{th}$ to $+213^{th}$ gene that contains uORF, respectively, both connected to the GUS reporter gene on a binary vector. (c) shows the GluB1 promoter (−245 to +18) sequence binding to the GUS reporter gene on a plasmid vector.

(B) are photographs showing the expression of GUS reporter gene in a seed during the maturation process. After cutting the seed (10 DAF) of a rice plant, into which the reporter gene was introduced, in the longitudinal direction, the cut seed was immersed in X-gluc solution and incubated at 37° C. EN indicates the endosperm, while EM indicates the embryo.

(C) is a graph showing the GUS activity of a seed extract of a transformed rice plant. 15 DAF seeds were used for analysis. The promoter structures of the introduced genes are as shown in (a) and (b) of (A), respectively. Vertical lines indicate the mean value. MU represents 4-methylumbelliferone.

Figure 7:
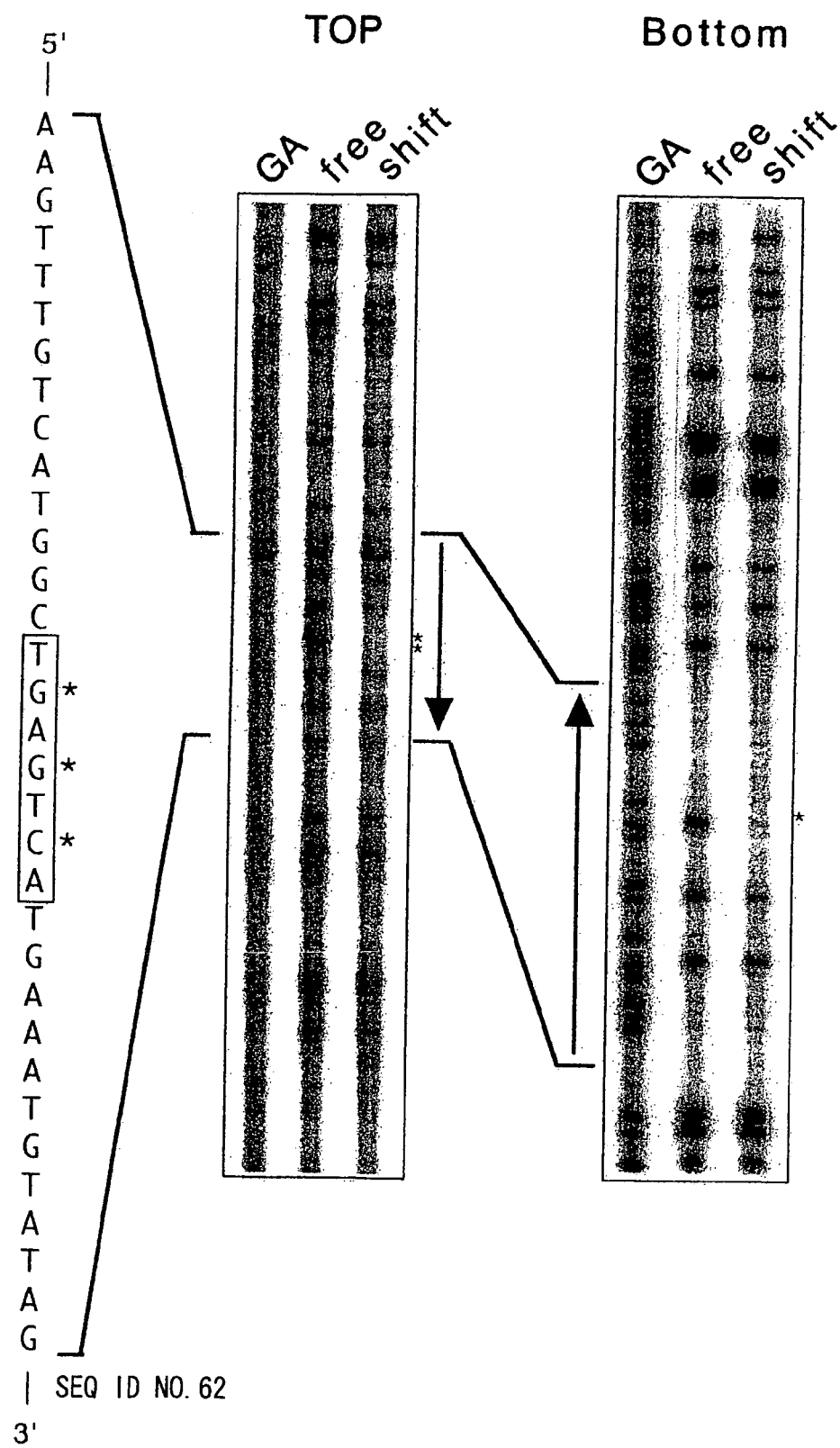

FIG. 7 shows photographs of gel electrophoretic patterns as determined from a methylation interference experiment for identifying the RISBZ1 protein-binding site on the GluB1 promoter. Each of the strands (top and bottom) of the promoter fragment of the GluB1 gene (−245 to +18) was labeled. After partially methylating each strand, they were incubated with GST-RISBZ1 protein, the fragments that did not bind to the protein and the fragment that bound to the protein were each collected and subjected to electrophoresis after chemically cleaved by piperidine. The sites (indicated by asterisks) that were not cleaved by piperidine were only found in the GCN4 motif.

Figure 8:
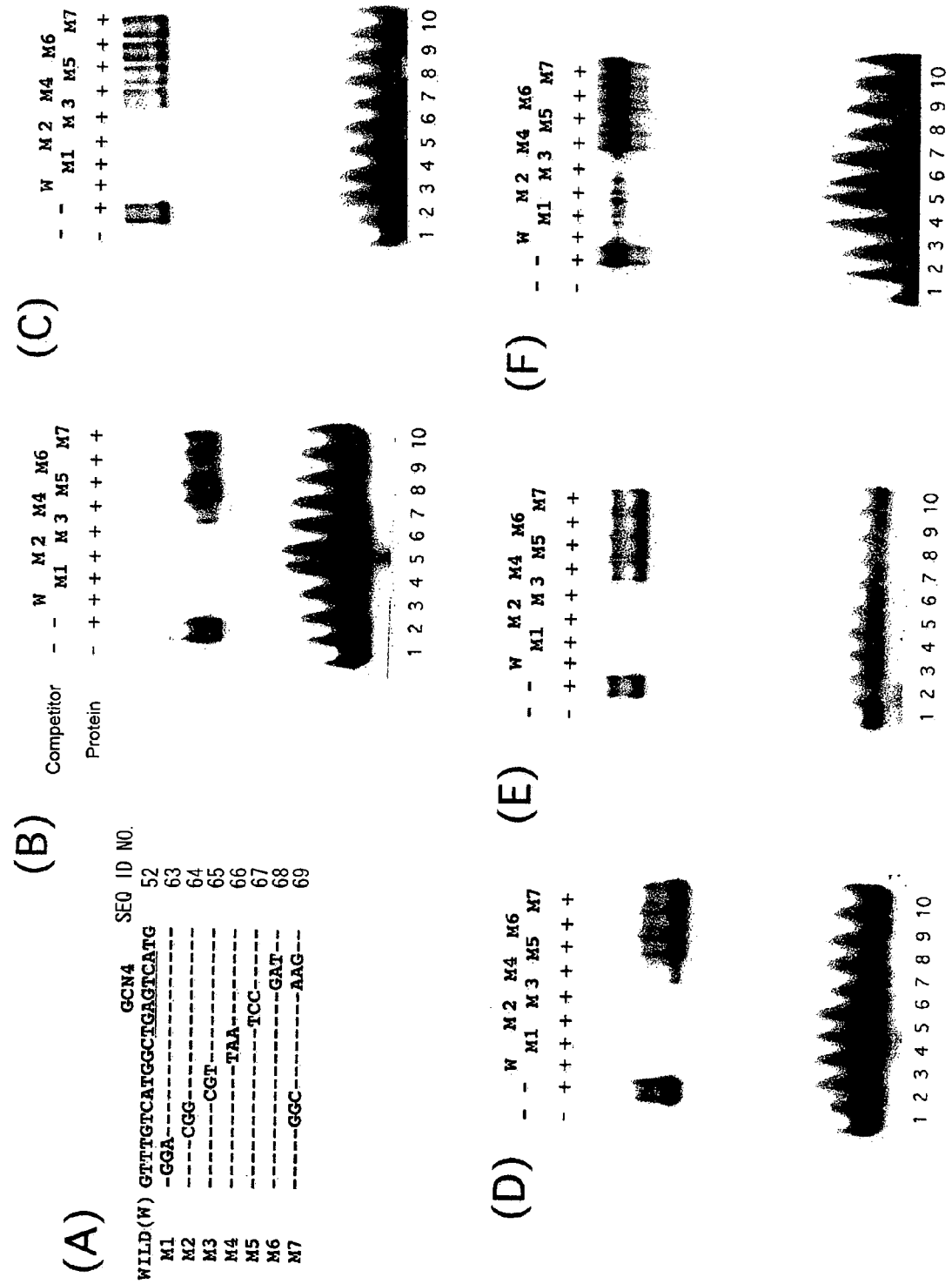

FIG. 8 shows the result of electrophoresis in gel shift analysis to investigate the binding capability of RISBZ1 protein to the GCN4 motif.

(A) shows 21-bp DNA fragments that contain the GCN4 motif of a WILD:GluB-1 promoter sequence (−175 to −155) of an oligonucleotide used as the probe and competitor. M1 to M7 are a series of 21-bp DNA fragments that were mutated every 3 bp. The GCN4 motif is underlined.

(B) through (F) show the results of gel shift analysis of the GST-RISBZ fused protein. A 21-bp DNA fragment (WILD) was added as the probe. (B) is for GST-RISBZ1, (C) for GST-RISBZ2, (D) for GST-RISBZ3, (E) for GST-RISBZ4, and (F) for GST-RISBZ5. The competitor was added to a stoichiometric ratio of 100 times or more against the probe. Lane 1: No protein; Lane 2: No competitor; and Lanes 3 to 10: With Competitor (wild type (W) and M1 to M7).

FIG. 9 represents heterodimer forming ability of RISBZ1 with other RISBZ proteins.

(A) shows the vector structure used as the in vitro transcription/translation reaction template. The vectors contain DNA coding for full-length RISBZ1 protein, short-form RISBZ2 protein (sRISBZ2: 218 to 329), or short-form RISBZ3 protein (sRISBZ3: 126 to 237).

(B) shows photographs of gel electrophoretic patterns representing the results of a DNA binding assay. In lanes 2, 4, 6, and 8, DNA complexes that bound to the full length or short-form protein were detected. In lanes 3 and 7, DNA complexes that bound to the heterodimer of full length RISBZ1 protein and short-form protein were detected.

Figure 10:
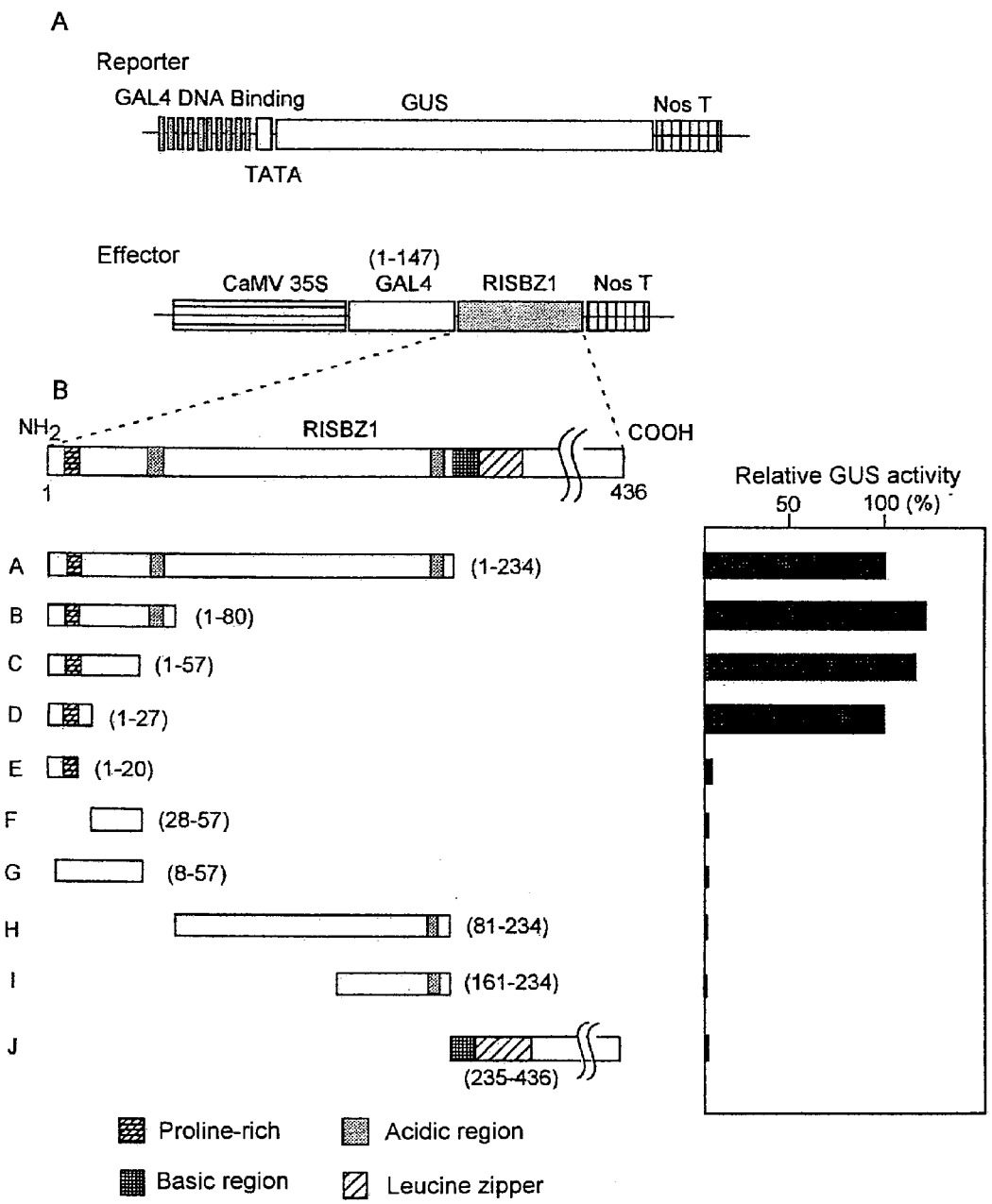

FIG. 10 shows the results of identification of the transcription-activating domain determined by transient analysis.

(A) shows the structure of the reporter and effector plasmid. A GUS gene in which 9 copies of GAL4-DNA binding sites and CaMV35S core promoter sequence are linked was used for the reporter. The effector plasmid contained DNA coding for a protein in which the GAL4 DNA binding domain was linked to the N-terminal side of truncated RISBZ1 protein.

(B) is a graph showing GUS activity when the reporter and effector plasmid were used.

Figure 11:
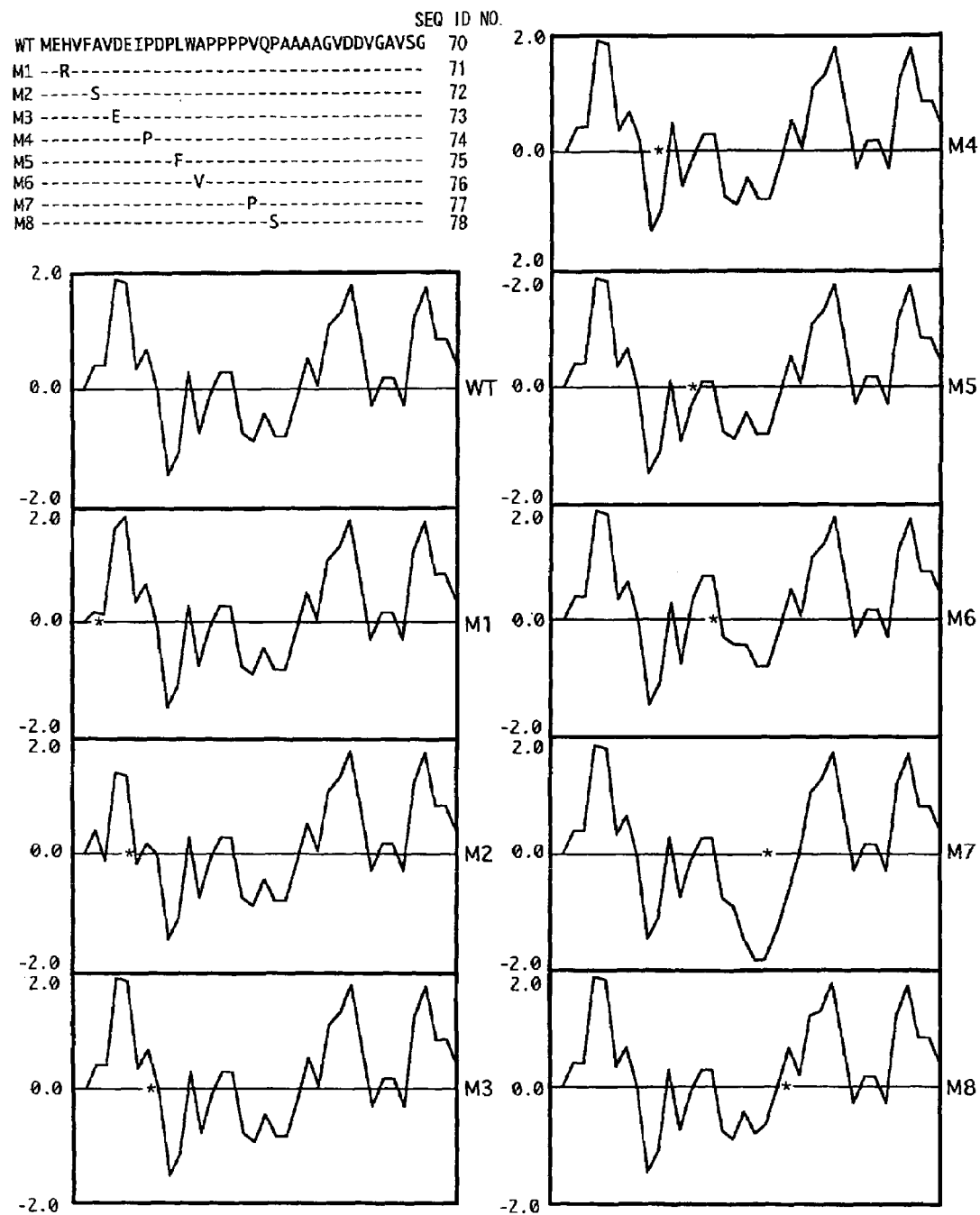

FIG. 11 shows the hydropathy patterns of the N-terminal region of RISBZ1 (WT) and mutant RISBZ1 (M1 to 8) proteins determined by the formula of Kyte and Doolittle (Kyte, J. and Doolittle, R. F. J., Mol. Biol. 157: 105–132, 1982). Positive values indicate hydropathy.

Figure 12:
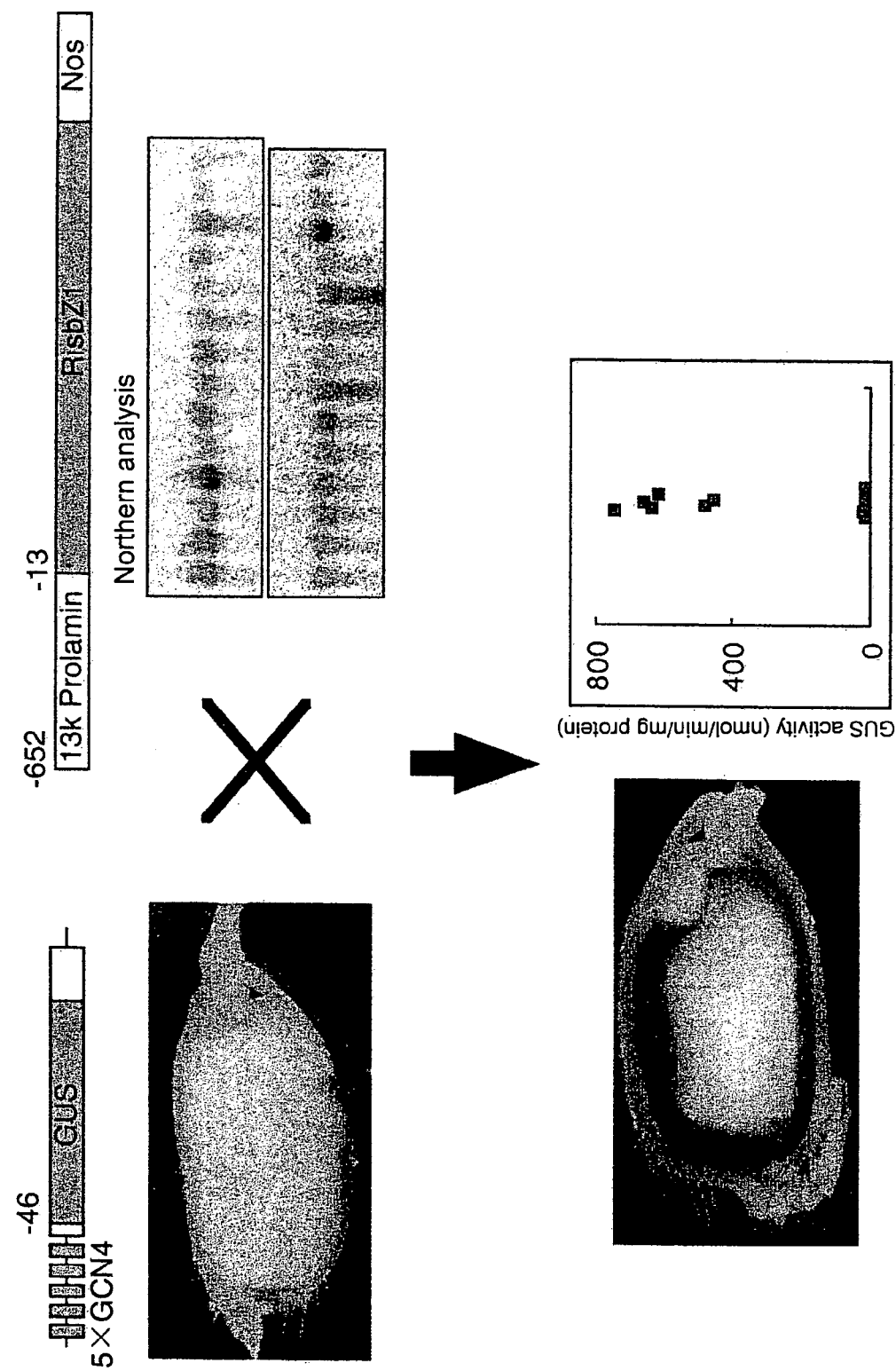

FIG. 12 schematically shows the transcription activity measurement system of RIZBZ1 using GUS activity as the indicator, photographs of Northern blot analysis, and a graph showing GUS activity measurement results. The ordinate of the graph represents GUS activity that is the indicator of the strength of the transcription activity of each transcription factor.

Figure 13:
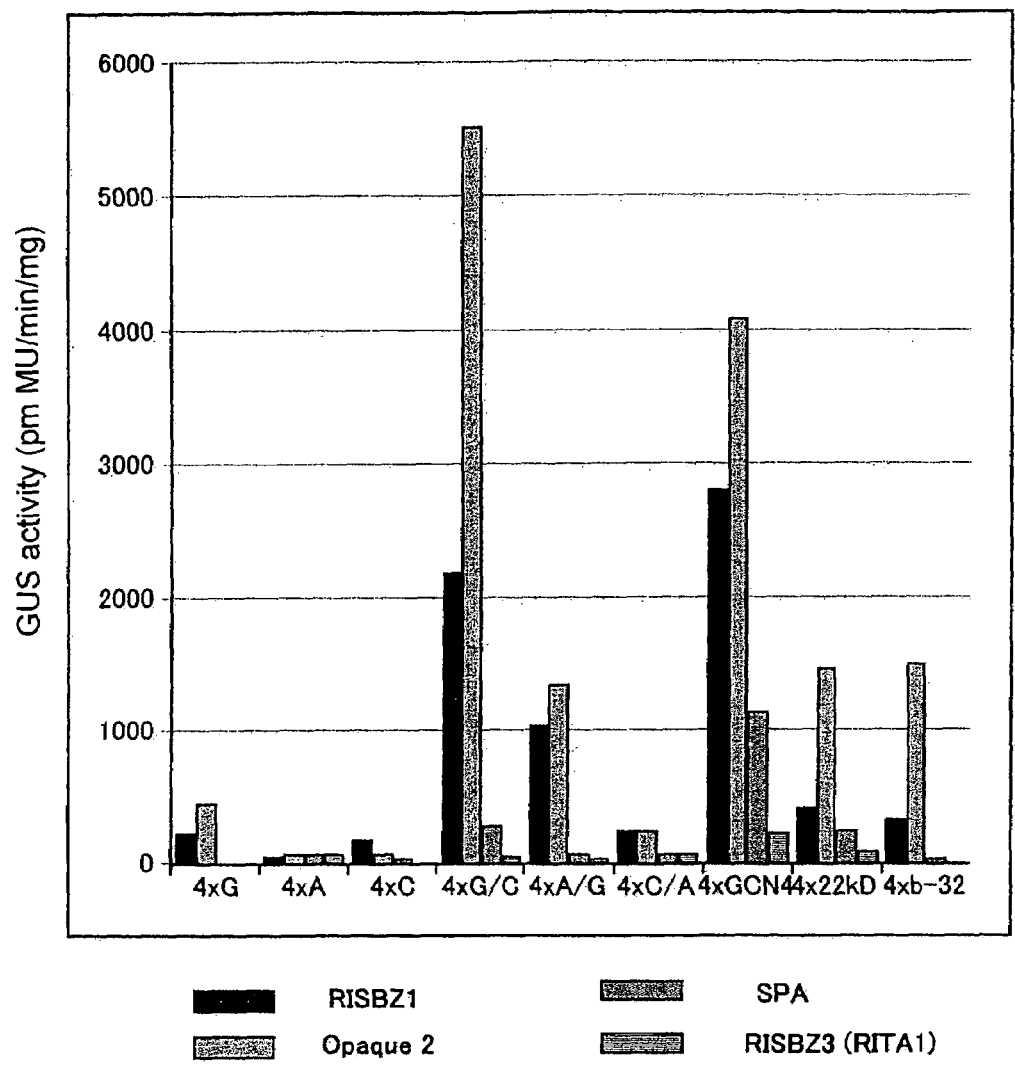

FIG. 13 is a graph showing the recognition sequences of transcription factors RISBZ1, Opaque2, SPA, and RISBZ3 (RITA1). The ordinate of the graph represents GUS activity that is the indicator of the strength of the transcription activity of each transcription factor. The sequences used in the experiment are shown below the graph.

Figure 14:
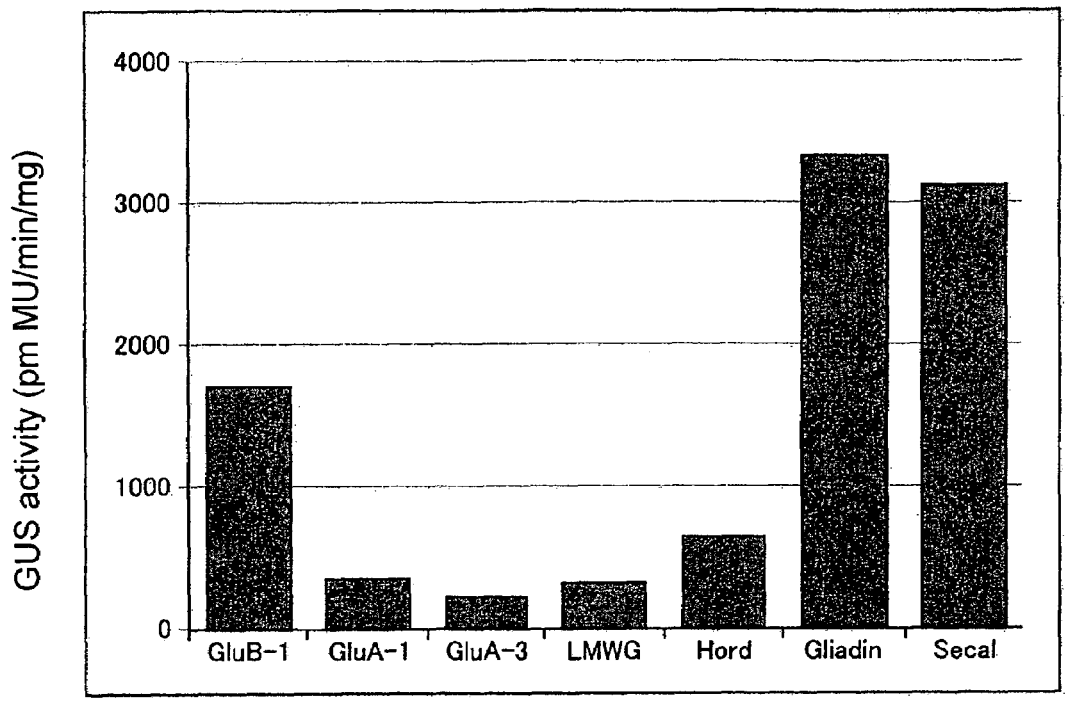

FIG. 14 is a graph showing the transcription activating ability of the RISBZ1 of the present invention relative to GCN4 motifs originating in various genes. The ordinate of the graph represents GUS activity, which is the indicator of the strength of the transcription activity of each transcription factor. The nucleotide sequences of the GCN4 motifs used in the experiment are shown below the graph.

MODE FOR CARRYING OUT THE INVENTION

The present invention will be described in more detail below with reference to Examples, but is not to be construed as being limited thereto.

EXAMPLE 1

Isolation of cDNA Clones Encoding the bZIP Transcription Factor From Seed cDNA Libraries Fourteen-day leaves and roots of rice plant (*Oryza sativa* L. c. v. Mangetumochi) cultivated by hydroponics were frozen in liquid nitrogen and kept at ~80° C. until use. Maturing rice seeds were collected from rice plants cultivated in the fields.

Using oligonucleotide primers designed from highly conserved amino acid sequences (SNRESA and KVKMAED) within the bZIP domain of the Opaque 2 (O2)-like protein, RT-PCR was performed by using poly(A)$^+$ mRNA as a template, which was prepared from the rice seeds. From poly (A) RNA extracted from seeds at 6 to 16 days after flowering (DAF) (Takaiwa F. et al. Mol. Gen. Genet. 208: 15–22, 1987), single-stranded cDNA was synthesized by reverse transcription using oligo(dT)$_{20}$ as a primer and Superscript reverse transcriptase (Gibco BRL, Paisly, UK). Next, cDNA was amplified using a pair of primers (5'-TCC AAC/T A/CGI GAA/G A/TCI GC-3'; SEQ ID NO: 16, and 5'-GTC CTC C/TGC CAT CTT CAC CTT-3'; SEQ ID NO: 17). These primers were designed based on highly conserved amino acid sequences within the bZIP-type transcription factors that were expressed in cereal seeds. After dissolving the single-stranded cDNA in a PCR reaction mixture containing 10 mM Tris-HCl pH 8.3, 1.5 mM MgCl$_2$, 50 mM KCl, 0.01% (w/v) gelatin, 200 μM dNTPs, 1 μM oligonucleotide primers, TaqI polymerase was added to the mixture and the resulting mixture was incubated in a thermal cycler at 94° C. for 5 min. cDNA was then synthesized and amplified by three-cycle PCR (for 1 min at 94° C., for 1 min at 40° C., and then for 2 mins at 72° C.) followed by 30-cycle PCR (for 1 min at 94° C., for 1 min at 55° C., and then for 2 mins at 72° C.). The amplified DNA fragment was cloned into a TA cloning vector (pCR2.1; Invitrogen), and subjected to sequencing by using the ABI PRISM dye terminator sequence system. The reaction products were analyzed by ABI PRISM 310 Genetic Analyzer (Perkin Elmer-Applied Biosystems) to determine the nucleotide sequences of at least 50 clones. The obtained nucleotide sequence data was analysed and searched on databases by using the GENETYX and BLAST algorisms. As a result, five distinct DNA fragments with 213-bp were found. Two of these were identical to the bZIP domain sequences of REB (Izawa T. et al. Plant Cell 6: 1277–1287, 1994) and the RITA1 (Nakase M. et al. Plant Mol. Biol. 33: 513–522, 1997). Using the five DNA fragments with 213-bp as primers, a cDNA library was prepared from RNA of maturing (6-16DAF) seeds (ZAPII; STRATAGENE) This was then screened to obtain their full-length cDNAs corresponding to each of the fragments under high stringent conditions. [α-$^{32}$P]-dCTP was incorporated into the DNA fragments by random priming (Amersham Pharmacia Biotech) and the resulting fragments were used as probes. As a pre-hybridisation solution, a mixture containing 5×SSC, 5× Denhard's solution, 0.1% SDS, 50% formamide, 100 µg/ml salmon sperm DNA was used. After hybridization, filters were washed once at 55° C. with a mixture consisting of 2×SSC and 0.1% SDS, and then twice at 55° C. with a mixture consisting of 0.1×SSC and 0.1% SDS.

Based on the homologies to each nucleotide sequence, the cDNA clones obtained were termed as RISBZ1 (rice seed b-Zipper 1) (SEQ ID NO: 1), RISBZ2, RISBZ3, RISBZ4 (SEQ ID NO: 4), and RISBZ5 (SEQ ID NO: 6). Among them, RISBZ2 and RISBZ3 were identical to REB (Izawa T. et al. Plant Cell 6: 1277–1287, 1994) and RITAL (Nakase M. et al. Plant Mol. Biol. 33: 513–522, 1997), respectively, which have previously been isolated from cDNA libraries of seeds and leaves.

EXAMPLE 2

Identification of RISBZ cDNA

The newly identified RISBZ cDNAs (RISBZ1, RISBZ4, and RISBZ5) were characterized in detail as described below. RISBZ1 cDNA was the longest, which had 1742 bp in length excluding poly(A), and contained a reading frame encoding 436 amino acids that had 46,491 Dal of an estimated molecular weight. RISBZ4 and RISBZ5 have reading frames encoding 278 and 295 amino acids; their estimated molecular weights are 29,383 Dal and 31,925 Dal respectively.

RISBZ1 mRNA has a longer leader sequence (245 bases long) than average leader sequences. Interestingly, a small open reading frame, encoding 31 amino acid residues, was found within the leader sequence in the upstream of the actual initiation codon of the RISBZ1 protein. Similar small upstream open reading frames (UORF) have previously been found in maize Opaque 2 (O2) (Hartings H. et al. EMBO J. 8: 2795–2801, 1989), wheat SPA (Albani D. et al. Plant Cell 9: 171–184, 1997), and barley BLZ1 and BLZ2 (Vincente-Carbojos J. et al. Plant J. 13: 629–640, 1998; Onate L. et al. J. Biol. Chem. 274: 9175–9182, 1999), but these uORFs have little homology with each other. It has previously been reported that uORF of the maize O2 mRNA is involved in translational control. uORF was found only in RISBZ1 mRNA but not in other RISBZ mRNA.

The flanking sequence of the initiation codon is GCAATGG. This sequence coincided with eukaryotic translational initiation sequence, c(a/c) (A/G) (A/C)cAUGGCG, derived from monocotyledonous plants. There were 100 bps between the initiation codon and uORF. The open reading frame encoding RISBZ1 had two identical termination codons (TAG). There were 229 bps between the termination codon and poly (A) sequence. The polyadenylation signal sequence (AATATA) was found in the region at −19 to −24 from the site to which poly(A) was added.

Figure 1:
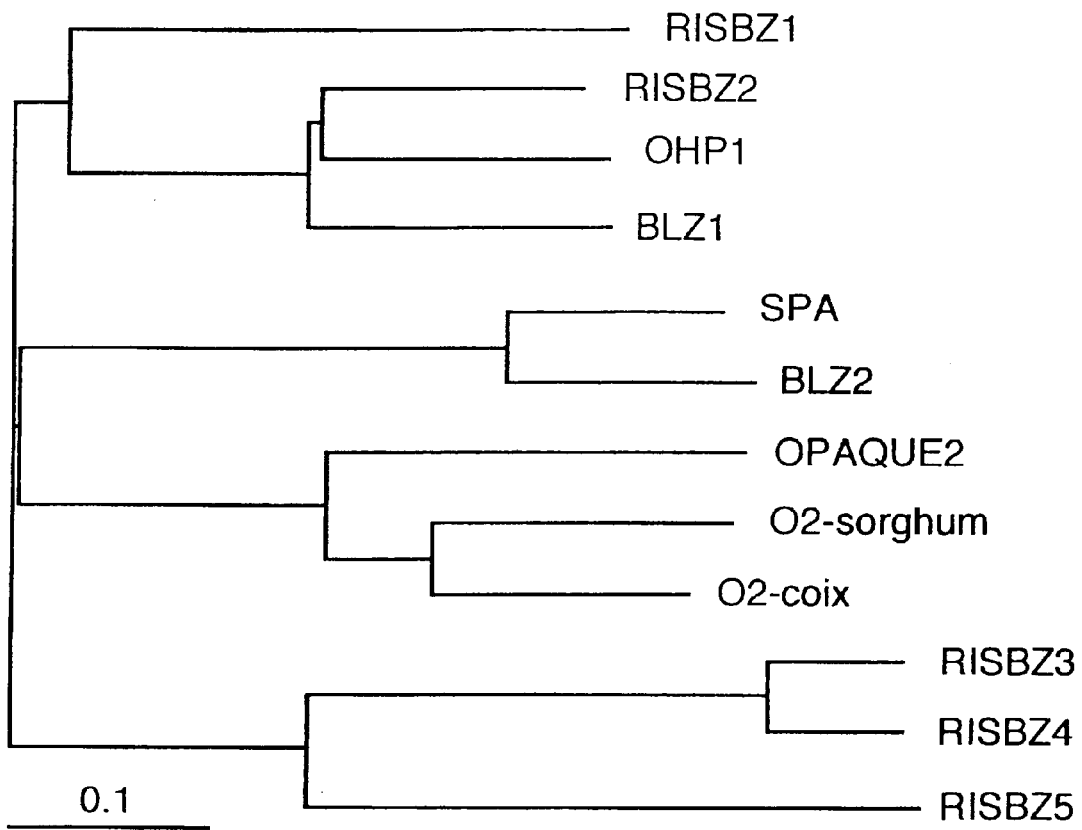
FIG. 1 is a drawing representing a genealogical tree based on the homology of the amino acid sequence of RISBZ protein and O2-like bZIP protein. The entire amino acid sequences of these proteins are compared to understand the similarity and the evolutionary relationship of these proteins.

RISBZ1 is closely related to rice REB (Nakase M. et al. Plant Mol. Biol. 33: 513–522, 1997), maize OHP-1 and OHP-2 (Pysh L. D. et al. Plant Cell 5: 227–236, 1993), and barley BLZ1 (Vincente-Carbojos J. et al. Plant J. 13: 629–640, 1998) (FIG. 1), and showed the homologies of 48.2% (rice REB), 45.7% (barley BLZ1), and 46.6% (maize OHPL), respectively, at the amino acid level. Furthermore, these bZIP domains were highly conserved (73.7% to 76.3%). At the amino acid level, the homologies of RITA1 (RISBZ3) with RISBZ4 and RISBZ5 were 88.8% and 47.6% respectively. By contrast, the homology of RISBZ4 with RISBZ5 was 48.2%. RISBZ3, RISBZ4, and RISBZ5 comprise a unique group among the O2-like transcription factors that were previously reported. Furthermore, the five RISBZ cDNAs isolated from the seed cDNA library could be classified into two groups based upon the amino acid homology (FIG. 1). The RISBZ3, RISBZ4, and RISBZ5 lacked the N- and C-terminal regions present in RISBZ1 and RISBZ2, and their sizes reduced about 100 to 150 amino acid residues compared with those of RISBZ1 and RISBZ2 (FIGS. 2 and 3).

RISBZ1 and RISBZ2 were rich in proline residues at their N-terminal region, which lacked in other RISBZ proteins (FIGS. 2 and 3). RISBZ1 and RISBZ2 were also rich in acidic amino acids at the peripheral region of the $60^{th}$ amino acid residue from their N-termini and at the intermediate region located in the upstream of their bZIP domains. These proline-rich or acidic amino acid-rich regions were found in other O2-like transcription factors.

Since serine-rich sequence (SGSS) was found in the region ranging from $207^{th}$ to $210^{th}$ residues of RISBZ1, the protein was considered to be a target sequence of casein kinase II (Hunter T. and Karin M. Cell 70: 375–387, 1992) (FIGS. 2 and 3) Similar sequence (SSSS) was also found in RISBZ2. However, it was missing in the other RISBZ proteins (FIGS. 2 and 3).

So far, two nuclear transition signals (NLSA: an SV-40-like motif and NLSB: a 2-factor motif) have been identified, which are involved in transport of maize Opaque2 (O2) proteins from cytoplasm into nucleus (Varagona M. J. et al. Plant Cell 4: 1213–1227, 1992). These motifs were searched on RISBZ1 and sequences homologous to NLSA and NLSB were found at the same sites as O2 (101 to 135 and 232 to 264).

EXAMPLE 3

Genomic Structure of the RISBZ1 Gene

Using primers designed from the nucleotide sequence of the RISBZL cDNA, the genomic region encoding promoter and RISBZL protein was isolated. The PCR reaction was performed using rice genomic DNA as a template and two pairs of oligonucleotide primers (RIS1f: 5'-ATGGGT-TGCGTAGCCGTAGCT-3'/SEQ ID NO: 18 and RELr5: 5'-TTGCTTGGCATGAGCATCTGT-3'/SEQ ID NO: 19) and (RELf2: 5'-GAGGATCAGGCCCATAT-3'/SEQ ID NO: 20 and RIS1r: 5'-TCGCTATATTAAGGGAGACCA-3'/SEQ ID NO: 21). DNA fragments were amplified using TAKARALA Taqpolymerase (TAKARA) in a thermal cycler through 30-cycle reactions for 10 sec at 98° C., for 30 sec at 56° C. and for 5 min at 68° C. The promoter region of the RISBZ1 gene was also amplified by thermal asymmetric interlaced (TAIL) PCR, based on the method by Liu et al, in which three oligonucleotides were used as specific primers, tail1: 5'-TGCTCCATTGCGCTCTCGGACGAG-3'/SEQ ID NO: 22, tail2: 5'-ATGAATTCGC-GAGGGGTTTTCGA-3'/SEQ ID NO: 23, and tail3: 5'-GTTTGGGAGAAATTCGATCAAATGC-3'/SEQ ID NO: 24.

Figure 4:
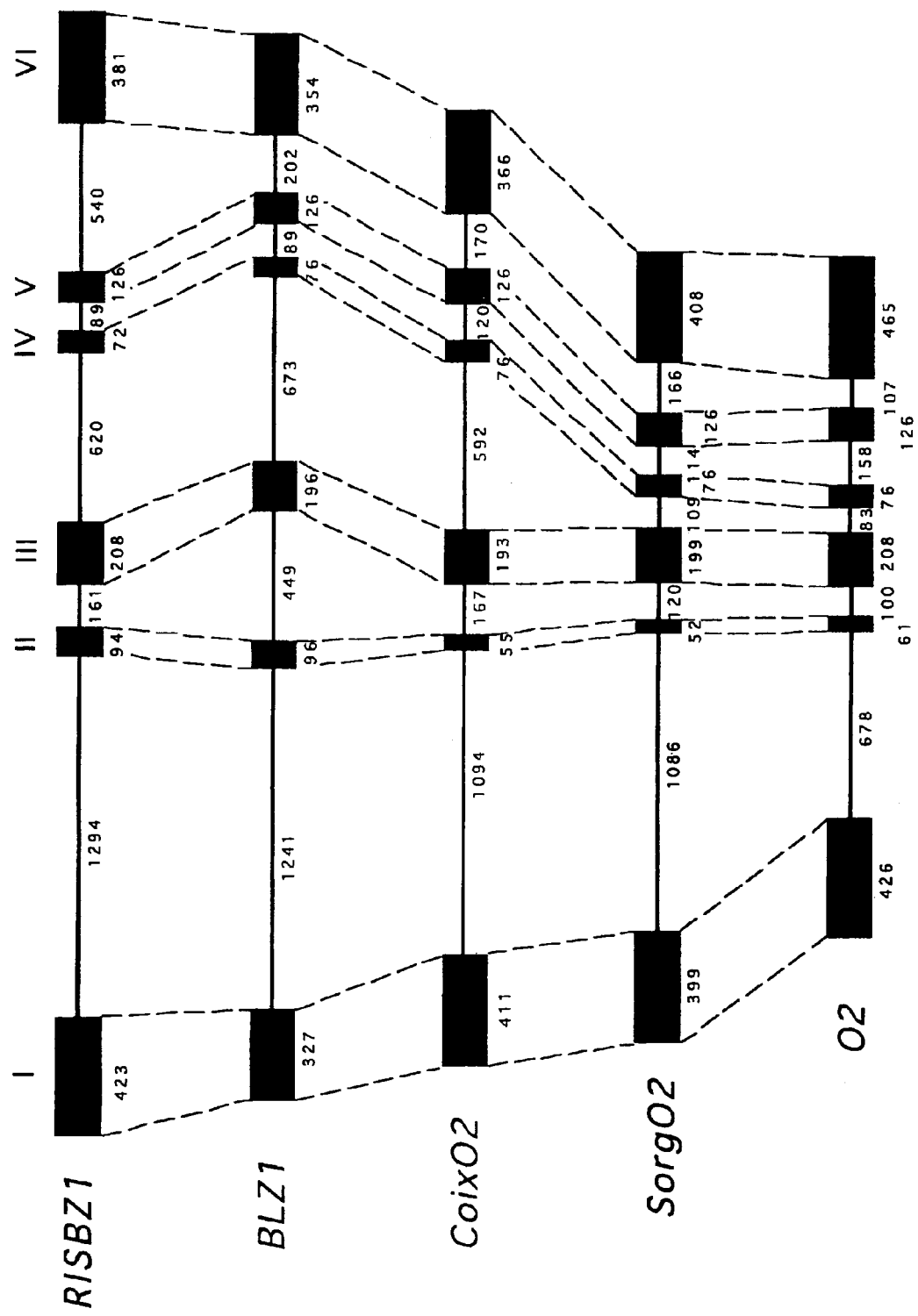
FIG. 4 shows the structure of a gene that codes for O2-like bZIP protein. The structures of the intron/exon region of the BLZ1 gene of barley and the Opaque2 gene of maize (O2) (Hartings, H. et al., EMBO J. 8: 2795–2801, 1989), sorghum (O2-sorg) and adlay (O2-coix) are shown. The thick bars and thin lines represent exons and introns, respectively. The numbers indicate the number of nucleotides of the exons and introns.

The results revealed that the RISBZ1 gene comprises of six exons and five introns (FIG. 4). The constitution of exon/intron in this RISBZ1 gene was identical to that of the maize O2 (Hartings H. et al. EMBO J. 8: 2795–2801, 1989), *Sorghum* O2 (Pirovano L. et al. Plant Mol. Biol. 24: 515–523, 1994), adlay O2 (Vettore A. L. et al. Plant Mol. Biol. 36: 249–263, 1998), and barley BLZ1 (Vicente-Carbojos J. et al. Plant J. 13: 629–640, 1998) genes (FIG. 4).

The transcription initiation site of the RISBZ1 gene was determined by the primer extension analysis according to the method of Sambrook et al. (Sambrook J. et al. Molecular Cloning: A Laboratory Manual, 2nd Ed., pp. 7.79–7.83, Cold Spring Harbor Laboratory Press, Cold Spring Harbor, N.Y.). Specifically, a primer, 5'-ATGGTATGGTGTTC-CTAGCACAGGTGTAGC-3' (SEQ ID NO: 25), was produced by labelling with T4 kinase, the 5' end of the oligonucleotide comprising 30 nucleotides, which was complementary to a sequence immediately downstream of a desired region. Reverse transcription reaction was conducted using this primer and 5 μg of mRNA as a template, and a Superscript reverse transcriptase kit (Gibco BRL, Paisly, UK). This reaction was carried out in a mixture comprising 20 mM Tris-HCl, 50 MM MgCl$_2$, 10 mM DTT, 500 μM dNTP, 100,000 cpm primer, 5 μg mRNA, and 200-unit Superscript reverse transcriptase (Gibco BRL, Paisly, UK), for 50 min at 42° C.

As a result, the transcription initiation site was mapped to the 245-nt upstream region from the translation initiation codon of the RISBZ1 gene. A 'TATA' box was localized at −30 to −35-nt from the transcription initiation site. Three 'ACGT' motifs were found in the 63-, 123-, and 198-bp upstream regions from the transcription initiation site but none of motifs responsible for expression of seed-specific genes, such as, GCN4 and 'AACA' were found. In contrast, a number of the recognition sequences for Dof domain protein, 'AAAG', were found. These motifs may be involved in stage- and/or tissue-specific expression of the RISBZ1 gene. For example, if the 'ACGT' motif is a target sequence of the RISBZ1 protein, the RISBZ1 gene may be autoregulated by itself. However, when the RISBZ1 promoter/GUS reporter gene and the $^{35}$S CaMV promoter/RISBZ1 gene were introduced into protoplast cells, no transcriptional activation of the reporter gene was observed. These data suggest that the RISBZ1 promoter has no target sequence for the RISBZ1 protein; namely, the 'ACGT' motif found in the RISBZ1 promoter is not a target sequence of the protein. Therefore, the RISBZ1 gene is probably not autoregulated. In contrast, upon overexpression of the rice prolamin box binding factor (RPBF) gene (which recognizes the Dof domain) transcription of the RISBZ1 promoter/GUS reporter gene is activated. This suggests that the recognition sequences of the Dof domain proteins are involved in specific expression of the RISBZ1 gene.

EXAMPLE 4

Tissue-Specificity of the RISBZ mRNA

Northern blotting was carried out to analyze the expression of the RIABZ gene. According to the method by Takaiwa et al. (Varagona M. J. et al. Plant Cell 4: 1213–1227, 1992), total RNA was extracted from 5 to 30 DAF seeds, roots, and seedling (5-, 10-, 15-, 20- and 30-DAF), and was transferred to membrane filters after fractionation by agarose gel electrophoresis. As probes, the following DNA fragments ranging from the downstream sequence of the bZIP domain-encoding region to the 3' non-coding region in the RISBZ cDNA were used: RISBZ1, 354-bp ranging from $1388^{th}$ to $1742^{nd}$ nucleotides; RISBZ2, 346-bp ranging from $1351^{st}$ to $1696^{th}$ nucleotides; RISBZ3, 486-bp ranging from $741^{st}$ to $1226^{th}$ nucleotides; and RISBZ5, 621-bp ranging from $742^{nd}$ to $1362^{nd}$ nucleotides.

Hybridization was carried out in a solution containing 5×SSC, 5× Denhard's solution, 0.1% SDS, and 50% formamide, at 45° C. After the hybridization, the membrane filters were washed twice for 30 min with a mixed solution comprising 2×SSC and 0.1% SDS, and then twice for 30 min with a mixture comprising 0.1×SSC and 0.1% SDS.

Figure 5:
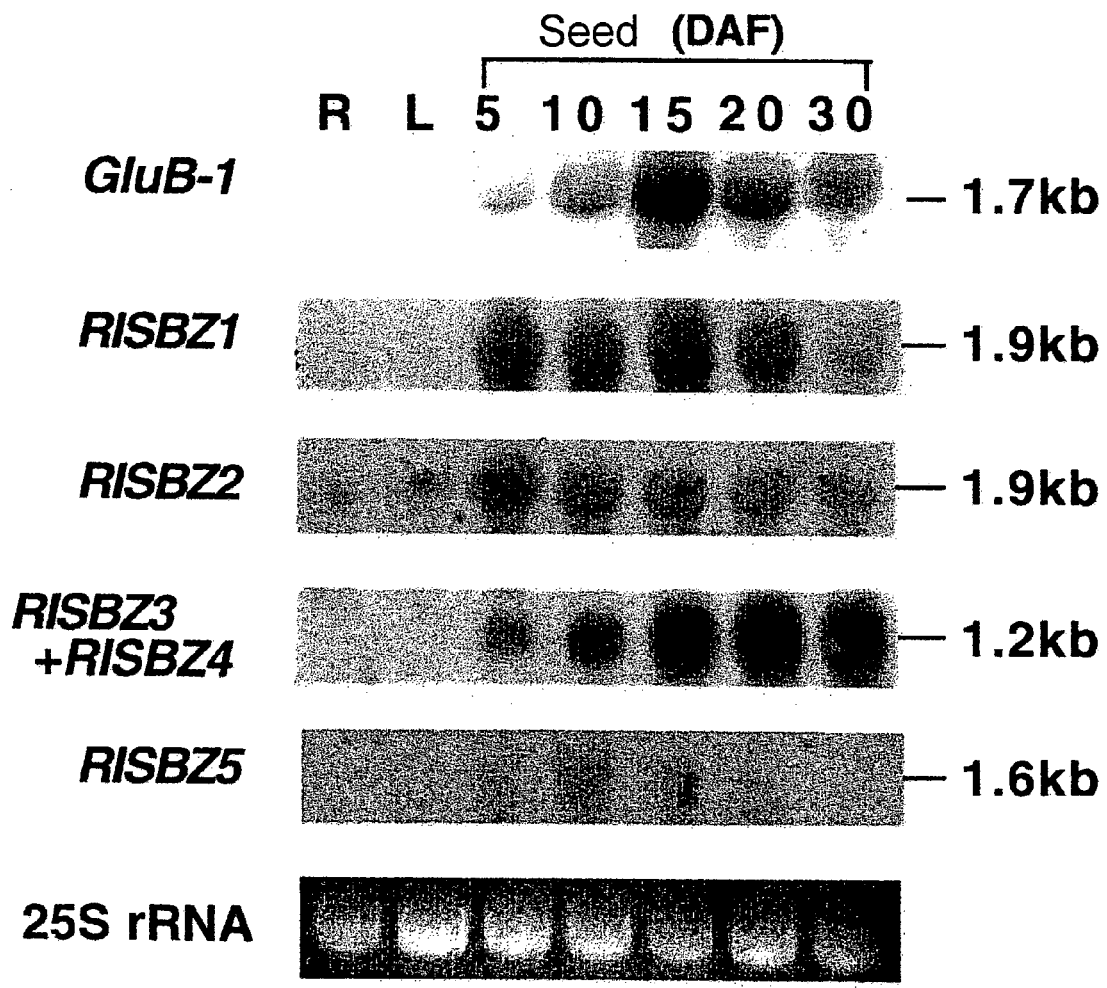
FIG. 5 is a photograph representing the result of a Northern blot showing the transcription patterns of the RISBZ genes. Northern blotting analysis was performed on the whole RNA extracted from the root, seedling, and maturing seeds (5, 10, 15, 20, and 30 DAF) using a unique nucleotide sequence of a region downstream of the bZIP domain for the probe. In order to compare transcription patterns, the analysis was also conducted using the. GluB-1 gene-coding region as the probe. The stained images of 25S rRNA obtained using ethidium bromide are shown as a control.

As shown in FIG. 5, the RISBZ1 gene was expressed only in seeds, not in other tissues analyzed. The largest amount of the RISBZ1 mRNA was accumulated in seeds harvested from 5 DAF to 10 DAF. Such a high accumulation of mRNA was maintained until 15 DAF, and gradually decreased towards maturing. The peak of the RISBZ1 gene expression appeared at an earlier stage than that of the glutelin gene. The glutelin mRNA expression was detected from 5 DAF, had a peak at 15 DAF, and was then gradually decreased (FIG. 5). This result suggests that the RISBZ1 acts as an activator of the glutelin gene. Similar expression patterns have also been reported in the maize O2 (Hartings H. et al. EMBO J. 8: 2795–2801, 1989), wheat SPA (Albani D. et al. Plant Cell 9: 171–184, 1997), and barley BLZ2 genes (Onate L. et al. J. Biol. Chem. 274: 9175–9182, 1999).

The RISBZ2 was expressed in all the tissues analyzed. The RISBZ3 and RISBZ 4 were expressed specifically in seeds at later stages of maturing (FIG. 5). The RISBZ3 and RISBZ 4 mRNA levels gradually increased until 20DAF and then decreased. The expression level of RISBZ5 was extremely low, compared with other RISBZ genes, and its mRNA peak was at 10 DAF.

EXAMPLE 5

Expression of the RISBZ1 Promoter/GUS Reporter Gene Construct in Transformants

To examine an expression pattern of the RISBZ1 gene, the sequence fragment ranging from −1674 to +213 nt numbering from the transcription initiation site, was ligated upstream of GUS gene. This reporter gene was introduced into rice plant by using *Agrobacterium* (FIG. 6A). Transformed rice plant (*Oryza sativa* L. c. v. kitaake) was constructed as follows. Two oligonucleotide primers with the PstI or BamHI restriction site at its 5' end, 5'-AAAACTG-CAGTTTTCTGA-3' (SEQ ID NO: 26) and 5'-AATGGATC-CGCGAGGGGTTTTCGAA-3' (SEQ ID NO: 27), were used to amplify the 5'-end regions (from $-1674^{th}$ to $+4^{th}$ and from $-1674^{th}$ to +213rd) of the RISBZ1 gene by PCR. The PCR reaction was carried out in a reaction mixture (10 mM Tris-HCl pH 8.3, 1.5 mM MgCl$_2$, 50 mM KCl, 0.01% (w/v) gelatine, 200 μM dNTPs, 1 μM primers, 0.5 μg template DNA, and 2.5-unit TaqI polymerase) by 30 cycles of incubation for 1 min at 94° C., for 1 min at 50° C. and for 2 min at 72° C. After digestion with restriction enzymes, PstI and BamHI, the PCR product was cloned into the plasmid vector pBI201, and was cleaved with restriction enzymes, PstI and SacI. The resulting DNA fragment containing the RISBZ1 promoter/GUS gene was inserted between the Sse8387I and SacI sites of the binary vector p8cHm, which contains the CaMV35S promoter/hygromycin phosphotransferase (HPT) gene. Transformation was performed according to the method described in Goto F. et al. Nature Biotech. 17: 282–286.

The reporter plasmid was constructed as follows. 1×21 bp, 3×21 bp, and 5×21 bp of GCN4 motifs/GUS genes, as constructed by Wu et al. (Wu C. Y. et al. Plant J. 14: 673–683, 1998), were used as the reporter. A pair of 48-bp oligonucleotides with overhanged (ACGT) 5' ends, which were complementary to each other, was associated to construct tetramers comprising 12-bp wild-type GCN4 motif (GCTGAGTCATGA/SEQ ID NO: 8) and mutant GCN4 motif (GCTTCCTCATGA/SEQ ID NO: 28). These double-stranded oligonucleotide were inserted into the SalI and StuI sites of the −46CaMV/GUS reporter gene.

Transient assay for rice callus protoplast was carried out according to the method described by Wu et al. The GUS activity was measured according to the method of Jefferson (Jefferson R. A. Plant Mol. Biol. Rep. 5: 387–405, 1987), by measuring fluorescence intensity of 4-methyl-umbelliferone derived from the glucuronide precursor. Using Bio Rad Kit, the concentration of proteins was measured. Bovine serum albumin was used as a standard protein.

As shown in FIG. 6B, high GUS activities was observed in the aleulon and sub aleulon layers of maturing seeds, but not in germs. The GUS activity was not detected in roots, leaves, and stems even by highly sensitive fluorescence measurement. These results indicate that the RISBZ1 gene is expressed exclusively in the aleulon and sub aleulon layers. To examine the role of the 5'-end untranslated region and uORF, the GUS activity was compared with that of a plant, which lacked uORF ranging from $-1674^{th}$ to $+4^{th}$ numbering from the transcription initiation site (FIG. 6A). As a result, no change in the expression site was observed due to the lack of uORF (FIG. 6B), but 5- to 10-fold weaker promoter activities were observed (FIG. 6C). These data suggest that the 5' untranslated region may play a role in upregulation of the translation, in contrast to the results in the maize O2 in which uORF functions as a suppressor of the translation (Lohmer S. et al. Plant Cell 5: 65–73).

EXAMPLE 6

Transcription Activating Ability of Five RISBZ Proteins Through Their Binding to the GCN4 Motif Transcription activating ability of the five RISBZ proteins through their binding to the GCN4 motif was measured by transient assay. The plasmids, into which each RISBZ1 protein-encoding sequences were ligated downstream of CaMV35S promoter as an effector, were prepared. Effector plasmids were prepared as follows. The plasmid that encodes RISBZ1 lacking its N-terminal region was prepared by PCR. In order to amplify cDNA encoding the regions ranging from $41^{st}$, $81^{st}$, $121^{st}$, and $161^{st}$ amino acids numbering from the N-terminus of RISBZ1 to its C-terminus the following primers were designed:

```
Forward primers
RIS1-1:
5'-AACCATGGTGCTGGAGCGGTGCCCGT-3'    (SEQ ID NO: 29)
```

```
RIS1-2:
5'-AACCATGGCGGCGGAGGCGGCGGCG-3'    (SEQ ID NO: 30)

RIS1-3:
5'-CCCCATGGAGTACAACGCGATGC-3'      (SEQ ID NO: 31)

RIS1-4:
5'-AACCATGGTTGGTTCCATCCTGAGT-3'    (SEQ ID NO: 32)

RIS1-5:
5'-AACCATGGCTCATGCCAAGCAAGCT-3'    (SEQ ID NO: 33)

RIS1-6:
5'-AACCATGGATGAAGAAGATAAAGTGAAG-3' (SEQ ID NO: 34)

Reverse primer
BRIS1R:
5'-TAGGATCCGCTCCTACTACTGAAGCT-3'.  (SEQ ID NO: 35)
```

These primers were designed to have an NcoI or BamHI restriction site at their 5' end. Since a translational initiation codon was lost by deletion of its N-terminal region, ATG of the NcoI restriction site was utilized. cDNAs were amplified by PCR comprising incubation for 2 min at 94° C., 30-cycle reaction for 1 min at 94° C., for 1 min at 50° C., and for 2 min at 72° C., followed by incubation for 5 min at 72° C. The PCR products were digested with restriction enzymes, NcoI and BamHI, and then purified through agarose gel electrophoresis. The purified cDNA fragments were finally inserted into the pRT100 vector (Topfer R. et al. Nucl. Acids Res. 15: 5890, 1987).

Plasmids encoding the fusion proteins comprising GAL4 DNA-binding domain (amino acid residues from $1^{st}$ to $147^{th}$) and the RISBZ1 or RISBZ2 gene were also constructed. In order to amplify the cDNA region encoding various N-terminal region of RISBZ1 and RISBZ2 by PCR using Pfu Taq polymerase (STRATAGENE), the following reverse primers, to which a BamHI site, a terminal codon, and an SstI site were added at its 5'-end, were prepared as well as the following forward primers:

```
Forward primers
RISBZ1-F1:    5'-AAGGATCCAATGGAGCACGTGTTCGCC-3'     (SEQ ID NO: 36)

RISBZ1-F2:    5'-AAGGATCCGGCGGCGGAGGCGGCGCG-3'      (SEQ ID NO: 37)

RISBZ1-F3:    5'-GCCGGATCCAGTTGGTTCCATCCTGAG-3'     (SEQ ID NO: 38)

RISBZ1-F4:    5'-AAGGATCCTGATGAAGAAGATAAAGT-3'      (SEQ ID NO: 39)

RISBZ1-F1-2:  5'-AAGGATCCAGGAGTAGATGACGTCGGC-3'     (SEQ ID NO: 40)

RISBZ1-F1-3:  5'-AAGGATCCAGACGAGATCCCCGACCCGCT-3'   (SEQ ID NO: 41)

Reverse primers
RISBZ1-R1:    5'-TAGAGCTCTACGCCGCCGGCATCGGGCT-3'    (SEQ ID NO: 42)

RISBZ1-R2:    5'-TAGAGCTCTAAAGGATCATATTTCCCAT-3'    (SEQ ID NO: 43)

RISBZ1-R1-1:  5'-TAGAGCTCTAGGCGGCCGCCGCCGGCTG-3'    (SEQ ID NO: 44)

RISBZ1-R1-2:  5'-TAGAGCTCTACGGCGGCGGCGGAGCCCA-3'.   (SEQ ID NO: 45)
``` cDNAs encoding various N-terminal regions of RISBZL and RISBZ2 were amplified by PCR comprising incubation for 2 min at 94° C., 30 cycles of reaction for 1 min at 94° C., for 1 min at 50° C., and for 1 min at 72° C., and then incubation for 5 min at 72° C., using the above-described primers. The amplified cDNAs were digested with BamHI and SacI restriction enzymes, and were purified by 2% agarose gel electrophoresis. The purified cDNA fragments were ligated downstream of the GAL4 DNA domain-encoding region in the $^{35}$S-564 vector digested with the same restriction enzymes so that their reading frames were matched. Mutations were also introduced into the N-terminal regions of RISBZ1 by PCR mutagenesis. The cDNA sequences were confirmed, and their partial sequence from $1^{st}$ to $57^{th}$ amino acid residues was amplified by PCR. The products were ligated downstream of the GAL4 DNA domain-encoding region in their reading frames.

In addition, reporter plasmids, into which the GUS gene, and one or three repeat(s) of the 12-bp GCN4 motif or one or five repeat(s) of the 21-bp GCN4 motif were inserted, were constructed. For negative control experiments, a reporter plasmid comprising four repeats of a mutant 12-bp GCN4 motif and the GUS reporter gene was used. The mutant 12-bp GCN4 motif has a mutation in the target sequence that is recognized by the RISBZ1 and O2. These plasmid constructs were introduced alone or in combination with other reporter or effector plasmid into rice protoplast cells prepared from its callus culture, and the GUS activity was assayed. When the reporter plasmid or effector plasmid was introduced alone into the protoplast, the GUS activity was detected at a low level. As shown in Table 1, however, in the presence of $^{35}$S/RISBZ1 or $^{35}$S/O2, which were introduced as effector plasmids, the transcription of the reporter gene was activated. Even in the presence of these effector plasmids, the transcriptional activity of the GUS gene downstream of the mutant 12-bp GCN4 motif was the same level as that of background. These results indicate that the RISBZ1 gene product activates the reporter gene mediated by the GCN4 motif. The transcriptional activity of the reporter gene induced by the RISBZ1 gene product was slightly higher than that induced by the O2 gene product. As shown in Table 2, the activity induced by RISBZ1 was enhanced depending on the copy number of the GCN4 motif. 1 to 12 copies of 21-bp GCN motif were assayed, and the transcriptional activity was enhanced proportionately up to 9 copies. However, even though the other RISBZ genes were expressed under the control of the $^{35}$S CaMV promoter, the transcriptional activity of the reporter gene was less than or equal to 1.4% of that induced by the RISBZ1 or O2 gene product. Thus, it was revealed that only the RISBZ1 protein can activate the transcription through its binding to the GCN4 motif.

TABLE 1

| Effector | GUS activity (pM 4-MU/min/mg protein) |
|---|---|
| 35S/Opaque2 | 2658 ± 318 |
| 35S/RISBZ1 | 2994 ± 157 |
| 35S/RISBZ2 | 44 ± 7 |
| 35S/RISBZ3 | 1.3 ± 1.2 |
| 35S/RISBZ4 | 17.3 ± 0.9 |
| 35S/RISBZ5 | 31 ± 8.8 |

The 4×12-bp GCN4 motifs/GUS reporter gene was introduced into protoplast cells together with the effector plasmid, and the GUS activity was measured. Data were obtained from three independent measurements.

TABLE 2

| | Effector GUS Activity (pM 4-MU/min/mg protein) | | |
|---|---|---|---|
| Reporter | (−) | (+) RISBZ1 | (+) Opaque2 |
| 1 × 12-bp GCN4 | 32 ± 1.5 | 295 ± 4.5 (9.2*) | 182 ± 6 (5.6*) |
| 4 × 12-bp GCN4 | 21 | 604 ± 24.5 (28.7*) | 452 ± 7.5 (21.5*) |
| 1 × 21-bp GCN4 | 30 ± 3 | 1318 ± 55.5 (43.9*) | 1139 ± 22.5 (37.9*) |
| 5 × 21-bp GCN4 | 104 | 13222 ± 1094 (127.1*) | 11932 ± 22.5 (114.7*) |

As a reporter, the 1×12-bp, 4×12-bp, 1×21-bp or 5×21-bp GCN4 motif/GUS gene was used. This table shows the GUS activity induced by the expression of RISBZ1 (+RISBZ1) gene or by Opaque2 (+Opaque2) gene.

EXAMPLE 7

Binding Site of the RISBZ1 Protein

The present inventors have previously discovered that the O2 protein recognizes the GCN4 motif (TGAGTCA) that is present in the promoter region ranging from $-165^{th}$ to $-160^{th}$ of GluB-1, a glutelin gene (Wu C. Y. et al. Plant J. 14: 673–683, 1998). By a methylation interference experiment, the present inventors have also determined the binding site of the RISBZ1 protein in the promoter region of the GluB-1 gene.

Production and purification of the GST-RISBZ1 fusion protein were performed as follows. Five coding regions from RISBZ1 cDNA were amplified by PCR using oligonucleotide primers to which the following appropriate restriction enzyme sites were added at their 5' end; BamHI-blunt ends for RISBZ1, BamHI-XhoI for RISBZ2, BamHI-SalI for RISBZ3, BamHI-SalI for RISBZ4, and BamHI-XhoI for RISBZ5. After digestion with the restriction enzymes, the PCR products were ligated into the cloning sites of the pGEX-4T-3 vector (Amersham Pharmacia Biotech). The GST-RISBZ fusion protein was expressed according to the method of Suzuki et al. (Suzuki A. et al. Plant Cell Physiol. 39: 555–559, 1998). After affinity purification, the GST fusion protein was dialyzed against a binding buffer comprising 20 mM HEPES-KOH pH 7.9, 50 mM KCl, 1 mM EDTA, and 10% glycerol, for four hours, and immediately stored at −80° C.

Methylation interference experiment was performed as described by Weinberger et al. (Weinberger J. et al. Nature 322: 846–849, 1986). The 5'-flanking region (from $-245^{th}$ to +18th nucleotides) of the GluB1 gene was digested with restriction enzymes, SalI and BamHI, and the ends of the fragment was labeled with [α-$^{32}$P] dCTP by a 'fill-in' reaction. The labelled fragment was methylated by treating it with dimethyl sulphate, mixed with GST-RISBZ1, and then incubated. Using non-denaturing acrylamide gel (5%, 0.25×TBE) electrophoresis, the DNA fragment complexed with GST-RISBZ1 and free DNA fragments were separated from each other. These DNA fragments were further purified by DEAE Sepharose column chromatography, were treated with piperidine, and were fractionated by 6% denaturing acrylamide gel electrophoresis.

As shown in FIG. 7, the GST-RISBZ1 fusion protein protected guanine residues that locate in the $-165^{th}$ to $-160^{th}$ region of the GluB-1 promoter. The guanine residues protected were the same residues protected in the O2 promoter (Albani D. et al. Plant Cell 9: 171–184, 1997). A guanine residue present in the 'ACGT' motif (also termed as an A/G hybrid box) at the $-79^{th}$ to $-76^{th}$ residues in the promoter region ranging from $-197^{th}$ to +18th, was not protected.

Furthermore, gel shift assay was conducted as described below to examine whether the RISBZ1 protein can recognize the GCN4 motif.

A pair of oligonucleotides complementary to each other, which was prepared by adding TCGA sequence was added to 21-nt fragment of GluB1 promoter region (from $-175^{th}$ to $-155^{th}$), was labeled at its ends with [α-$^{32}$P] dCTP by 'fill-in' reaction for use as a probe. Seven pairs of complementary oligonucleotides with mutations every three contiguous nucleotides (FIG. 8A) were also synthesized for use as mutant competitor fragments and were annealed. Gel shift analysis using the GST fusion protein was carried out by a method described by Wu et al. (Wu C. Y. et al. Plant J. 14: 673–683, 1998) and by Suzuki et al. (Suzuki A. et al. Plant Cell Physiol. 39: 555–559, 1998). The labeled oligonucleotide probe was mixed with 0.5 µg of the GST-RISBZ fusion protein, and incubated for 20 min at room temperature. In competition experiments, the competitor fragment was added to the mixture at the 100-fold or higher molecular weight ratio. The reacted mixture was analyzed by non-denaturing acrylamide gel (5%, 0.25×TBE) electrophoresis.

The detection of shift bands showed that the GST-RISBZ1 protein was able to bind to the 21-bp DNA fragment containing the GCN4 motif (FIG. 8B). Furthermore, as shown FIG. 8A, the 21-bp DNA fragments with mutation in every three contiguous nucleotides were used as competitors and examined. When the DNA fragments with the mutations in the GCF motif were added as the competitor, the binding of the DNA fragments that were added as probes was hardly or not inhibited at all (FIGS. 8B to F). By contrast, when the DNA fragments with mutations in the franking sequence of the GCN4 motif were added as the competitor, the shift bands disappeared (FIGS. 8B to F). Since the mutation of the GCN4 motif markedly affects the binding of the RISBZ1 protein to the motif, it was revealed that the RISBZ1 protein recognizes the GCN4 motif sequence specifically. The similar experiments carried out using the other RISBZ proteins revealed that all the RISBZ proteins could specifically recognize the GCN4 motif. As shown in FIGS. 8B to F, the affinity of each RISBZ proteins for the GCN4 motif slightly varies. In the cases of RISBZ2 and RISBZ5, when the DNA fragments with mutations in the franking sequence of the GCN motif were used as the competitor, the shift bands were not disappeared completely (FIGS. 8C and F).

From these results, it was revealed that the RISBZ proteins specifically recognize the GCN4 motif with slightly variable affinities.

EXAMPLE 8

Ability of RISBZ1 Protein to Form a Heterodimer

It was considered that the RISBZ1 protein, a bZIP-type transcription factor, binds to the GCN4-like motif upon forming a heterodimer with other RISBZ proteins. Therefore, the ability of RISBZ1 to heterodimerize with RISBZ2 or RISBZ3 was examined. The full-length RISBZ1 protein, and short-form-RISBZ2 protein (sRISBZ2) and short-form RISBZ3 protein (sRISBZ3) were prepared using wheat germ extracts (FIG. 9A), and were used for DNA binding assay. The in vitro translation was carried out as follows. The coding region of RISBZ1 cDNA and the bZIP domain-encoding regions of RISBZ2 cDNA and RISBZ3 cDNA were amplified using the following forward primers with the NcoI site at their 5' ends and reverse primers encoding a terminator codon and the BamHI site;

```
For RISBZ1
R1F:      5'-AAACCATGGAGCACGTGTTCGCCGT-3' and      (SEQ ID NO: 46)
BRIS1r:   5'-TAGGATCCGCTCCTACTACTGAAGCT-3';       (SEQ ID NO: 47)

For sRISBZ2
dR2-1:    5'-AAACCATGGAGGGAGAAGCTGAGACC-3' and    (SEQ ID NO: 48)
R2ra1:    5'-AAAGGATCCTACATATCAGAAGCGGCGGGA-3'; and (SEQ ID NO: 49)

For sRISBZ3,
dR3-1:    5'-AAACCATGGATATAGAGGGCGGTCCA-3' and    (SEQ ID NO: 50)
R3ra1:    5'-AAAGGATCCTACAGCCCGCCCAGGTGGCCG-3'.   (SEQ ID NO: 51)
```

PCR amplification was carried out in a reaction mixture comprising 10 mM Tris-HCl pH 8.3, 1.5 mM MgCl$_2$, 50 mM KCl, 0.01% (w/v) gelatine, 200 µM dNTPs, 1 µM primers, 0.5 mg template DNA, and 2.5-unit TaqI polymerase by 30 cycles of incubation for 1 min at 94° C., for 1 min at 50° C. and for 2 min at 72° C.

The PCR products were digested with restriction enzymes, NcoI and BamHI, and were ligated into the pET8c cloning vector (Novagen) to construct plasmids. Using these plasmids as templates, in vitro transcription/translation (TNT coupled wheat germ extract systems; Promega) was performed for the production of the full-length RISBZ1 protein, and short-form-RISBZ2 (RISBZ2s) and -RISBZ3 (RISBZ3s). For gel shift assay, 4 µl of the wheat germ extract that was used in the above reaction was used.

Gel shift assay was employed to separate homodimers and heterodimers bound to the 21-bp GCN4 motifs. After pre-incubating RISBZ1 with sRISBZ2 and sRISBZ3, the DNA probes comprising the GCN4 motif were added to the incubation mixture. The results indicate that RISBZ homodimers as well as heterodimers can bind to the GCN4 motif. Therefore, it was demonstrated that the RISBZ proteins form heterodimers with the other members of the RISBZ family.

EXAMPLE 9

Involvement of the N-Terminal Region of the RISBZ1 Proteins in the Transcriptional Activation Transient assay was performed to identify the domain of the RISBZ1 protein involved in transcription activation. The GUS gene, to which three copies of the 21-bp GCN4 motif and the core promoter sequence of CaMV35S were connected, was prepared as a reporter. Various domains of the RISBZ1 proteins were expressed using the CaMV35S promoter in order to examine if these domains can activate the reporter gene.

A series of effector plasmids encoding RISBZ1 proteins in which every 40 amino acids from N-terminus to the basic domain were deleted (encoding the amino acids region ranging from $41^{st}$ to $436^{th}$, $81^{st}$ to $_{436}$, $121^{st}$ to $436^{th}$, $161^{st}$ to $436^{th}$, $201^{st}$ to $436^{th}$, or $235^{th}$ to $436^{th}$ in the amino acid sequence set forth in SEQ ID NO: 2), were constructed. When the effector plasmid encoding the full-length RISBZ1 protein and the reporter plasmid (the GUS gene to which four copies of the 12-bp GCN motif and the core promoter sequence of CaMV35S were linked) were introduced into protoplasts, approximately 30-fold higher activity of GUS was detected compared to that of protoplast into which the reporter plasmid alone was introduced. When the transcriptional activity of this reporter gene was set as 100%, the activity of the gene with deletion of the first 40-amino acid was decreased to 20%. Furthermore, the activity of the reporter gene was decreased gradually to 10% by deleting each 40 amino acids. Hence, it was suggested that the N-terminal 40 amino acid residues of RISBZ1 are mainly involved in the transcription activation.

To further analyze the association of the N-terminal 40 amino acids of RISBZ1 with its transcription activating ability, various fusion proteins between the DNA binding domain of the yeast transcriptional activating factor GAL4 and various portions of the RISBZ1 protein were constructed and expressed for the gain-of-function assay. As shown in FIG. 10, a plasmid, in which the coding sequences of fused proteins comprising the GAL4-DNA binding domain and various regions of RISBZ1 were connected downstream of the CaMV35S promoter, was constructed and used as an effector. These effector plasmids were introduced into protoplast together with a reporter construct (the GUS gene, to which nine copies of the GAL4-DNA binding site and CaMV35S core promoter were connected).

The significant difference was not found in transcription activating ability of the fusion protein comprising the GAL4-DNA binding domain and the partial amino acid sequence from 1st to $235^{th}$ amino acids of RISBZ1, compared with that of a series of the fused proteins in which amino acids were deleted towards the $27^{th}$ residue from the C-terminal residue of RISBZ1 (FIG. 10). The transcription activating ability of the fusion protein with the first 20 amino acid residues were dramatically decreased (FIG. 10). A fusion protein with deletion of the N-terminal eight residues of RISBZ1 lost the transcriptional activity. In contrast, fusion proteins comprising the GAL4-DNA binding domain and other region of RISBZ1 (from $27^{th}$ through $57^{th}$, $81^{st}$ through $234^{th}$, $161^{st}$ through $234^{th}$, or $235^{th}$ through $436^{th}$ in SEQ ID NO: 2) had no effect on the transcriptional activity of the reporter gen. These results suggest that the proline-rich domain within the N-terminal 27 amino acid residues of the RISBZ1 protein, rather than the acidic domain, involves in the transcription activation.

EXAMPLE 10

Difference Between RISBZ1 and Other RISBZ Proteins in Transcription Activating Ability Analyzed by Domain Swapping Although all the members of the RISBZ protein family have similar affinity for the GCN4 motif sequence, only the RISBZ1 has the transcription activating ability. To find out the reason of this difference, domain swapping between RISBZ1-, and RISBZ2- or RISBZ3-protein was carried out. The N-terminal region at $1^{st}$ through 299th of RISBZ1, which resides upstream of the bZIP domain, was replaced with the N-terminal region, $1^{st}$ through $229^{th}$ of RISBZ2 or $1^{st}$ through $137^{th}$ of RISBZ3.

Fusion proteins that have the N-terminal region of RISBZ1 together with the DNA binding domain of RISBZ2 or RISBZ3 showed only approximately 15% or 38% of the transcription activating ability, respectively, compared with that of the full-length RISBZ1. In contrast, fusion proteins that have the N-terminal region of RISBZ2 or RISBZ3 together with the RISBZ1 DNA binding domain showed a slightly higher transcription activity than that induced by the RISBZ1 DNA binding domain alone.

These results indicate that the N-terminal region is mainly involved in the transcription activation. The lower level of the RISBZ2 or RISBZ3 transcription activating ability may be due to deletion or mutation of the region corresponding to RISBZ1 transcription activating domain during evolution. Alternatively, the formation process of transcription activating domain may be responsible for that. It is highly possible that the lower activity of RISBZ3 is due to the lack of the proline-rich domain present in RISBZ1. This applies to RISBZ4 and RISBZ5. The results of the gel shift assay probably exclude the possibility that the differences of affinity with GCN4 motif raise the differences of transcription activating ability.

The proline-rich domain of RISBZ1 was also highly conserved in RISBZ2, but the transcription activating ability of RISBZ2 was extremely low compared to that of RISBZ1. When an effector plasmid that encodes a fused protein comprising the N-terminal 27 amino acid residues of RISBZ2 including proline-rich domain and the GAL4-DNA binding domain was introduced together with a reporter plasmid encoding the GCN4 motif connected to the GUS gene into protoplast, no increased activity of GUS was observed.

Since only eight-residue differences among the N-terminal 27 residues were observed between RISBZ1 and RISBZ2, the present inventors have examined which of the residues among the eight are responsible for the difference in transcription activating ability. The eight amino acid residues of RISBZ1, which were different from RISBZ2, were replaced one by one with the residues of RISBZ2, and the resulting chimeric N-terminal sequences comprising 40 amino acids were fused with the GAL4-DNA binding domain to construct effector plasmids encoding the fused proteins. These effector plasmids were introduced into protoplast together with the reporter plasmid in which the GCN4 motif was fused with the GUS gene. Among eight effector plasmids, all the effector constructs, except for those encoding a protein with replacement of the seventh residue counting from the N-terminus of RISBZ1, did not activate the transcription of the reporter gene. It was presumed using the Kyte and Doolittle formula that all these seven substitutions of amino acids, which were lost transcription activating ability, would induce the change of a hydropacy pattern (FIG. 11).

EXAMPLE 11

Use of the Transcription Factor RISBZ1 for Plant Breeding

The present inventors have examined the possibility to use the transcription factor, RISBZ1, which has a transcription activating ability for plant breeding. In order to specifically overexpress the transcription factor in seeds, rice-plants were transformed with a plasmid construct that encodes the RISBZ1 gene under the control of the promoter of the rice prolamin gene, which encodes a seed storage protein, with 13-kDa molecular masses. The DNA fragment ranging from the EcoRI site, located at the $-29^{th}$ position, to the poly (A) addition site of the RISBZ1 gene was linked to the prolamin promoter encompassing from the $-652^{nd}$ through $-13^{th}$ from the translation initiation site ATG of the gene. The construct was inserted into the binary pGTV-Bar vector, and the resulting vector was introduced into rice plants using Agrobacterium. By this approach, 28 independent transformed lines were established. Screening of rice plants that overexpress the RISBZ1 mRNA was carried out by Northern hybridization of RNA extracted from maturing seeds using cDNA of RISBZ1 as a probe (FIG. 12). These lines overexpressing RISBZ1 were crossed with the transformed rice plants, in which a plasmid construct encoding five tandem repeats of the 21-bp GCN4 motif (5'-GTTTGT-CATGGCTGAGTCATG-3'/SEQ ID NO: 52), a target of the RISBZ1 protein, linked to the minimum promoter/GUS reporter had been introduced.

As a result, it was revealed that the expression level of GUS reporter genes were, due to overexpression of RISBZ1 enhanced by 400-times or more (450 to 750 nmol/min/mg protein) than that of controls, 5×GCN4 lines (11 to 14 nmol/min/mg protein) (FIG. 12). These results suggest that the transcription of foreign genes can be highly activated by connecting the foreign genes downstream of the target sequence of the transcription factor RISBZ1 with transcription activating ability and overexpressing RISBZ1.

The RISBZ1 proteins can activate not only the glutelin gene but also other storage protein genes. The $^{35}$S CaMV promoter/RISBZ1 fusion construct together with the glutelin promoter/GUS, glutelin promoter ($-980^{th}$ to ATG)/GUS, or 13-Kd prolamin promoter (from $-652^{nd}$ to $-29$th)/GUS, was introduced into rice protoplast using electroporation, and the transient expressions of them were examined.

The results indicated that the RISBZ1 protein bound to the target sequences containing GCN4 motifs in these promoters and activated the transcription of the foreign genes. It was revealed that the transcriptions were activated 5 to 10-fold in the case of the 13-Kd prolamin promoter and 20 to 30-fold in the case of the globulin promoter, higher than that of the background. Therefore, methylation interference reaction was used to determine how RISBZ1 recognizes the nucleotide sequences of these genes.

The results showed that three GCN4 motifs (TGACACA/SEQ ID NO:86, GATGACTCA/SEQ ID NO:87, and TGACTCAC/SEQ ID NO:88) of the prolamin gene and three motifs different from the GCN4 motif (GGTGACAC SEQ ID NO:89, GTATGTGGC /SEQ ID NO:90, and GATCCATGTCAC/SEQ ID NO:91) of the globulin gene were recognized by the RISBZ1 protein. To determine specific sequences in the promoters that are recognized by the RISBZ1, transient expression of the GUS gene was examined by using a chimeric promoter sequence in which the G, A, C, G/C, MG, or C/A box, GCN4, 22-Kd zein binding site and four repeats of 12-bp sequence including the b-32 binding site were inserted in tandem into the 46 CaMV 35S core promoter/GUS reporter gene. The results indicate that the RISBZ1 protein preferentially recognizes the G/C box and GCN4 motif (FIG. 13).

Furthermore, it was studied to see if the RISBZ1 protein recognized various distinct GCN4 motifs present in the promoter for the storage protein genes. The results indicate that the flanking sequences of the core sequence 'TGAGTCA' of GCN4 motif influence transcription activating ability, and that the GCN4 motifs of the wheat gliadin gene and rye secalin gene have high transcription activating ability (FIG. 14).

INDUSTRIAL APPLICABILITY

The present invention provides novel transcription factors that regulate the expression of rice seed storage proteins, and genes that encode the transcription factors. It is expected that the expression of many seed storage proteins regulated by the RISBZ1 protein of the present invention having transcription activating ability can be enhanced by introducing the gene encoding the RISBZ1 protein into cells to overexpress it. The present invention also provides novel gene expression systems in which a useful foreign gene, encoding such as an antibody and an enzyme, can be highly expressed using the transcription factor of the present invention, by linking the recognition sequence of the transcription factor, the GCN4 motif, in tandem and introducing it into the promoter for a gene encoding a seed storage protein to facilitate its binding to the transcription factor. Thus, expression of the gene encoding storage protein and the useful foreign gene can be greatly enhanced under the control of the modified promoter. This enables abundant accumulation of a seed storage protein in endosperm, and more nutritious seeds (e.g. rice) and production of seeds in which useful proteins are highly accumulated.

SEQUENCE LISTING

```
<160> NUMBER OF SEQ ID NOS: 52

<210> SEQ ID NO 1
<211> LENGTH: 1751
<212> TYPE: DNA
<213> ORGANISM: Oryza sativa
<220> FEATURE:
<221> NAME/KEY: CDS
<222> LOCATION: (211)..(1518)

<400> SEQUENCE: 1
ggcacgagaa aaacccatg ggttgcgtag ccgtagcttt cccaccattt ccttctctcc      60
gaagcctcct cctctccgct tcctcccgcg aaaccaaatt ccaaagcatt tgatcgaatt    120
tctcccaaac ttttccagcg ttttcaattt cgccccgatt tcggttcgaa aaccccctcgc   180
```

```
gaattcattt caaactcgtc cgagagcgca atg gag cac gtg ttc gcc gtc gac      234
                                   Met Glu His Val Phe Ala Val Asp
                                    1               5 gag atc ccc gac ccg ctg tgg gct ccg ccg ccg ccg gtg cag ccg gcg      282
Glu Ile Pro Asp Pro Leu Trp Ala Pro Pro Pro Pro Val Gln Pro Ala
     10              15                  20 gcg gcc gcc gga gta gat gac gtc ggc gcg gtg agc ggc ggc ggg ttg      330
Ala Ala Ala Gly Val Asp Asp Val Gly Ala Val Ser Gly Gly Gly Leu
 25              30                  35                  40 ctg gag cgg tgc ccg tcg ggg tgg aac ctc gag agg ttt ctg gag gag      378
Leu Glu Arg Cys Pro Ser Gly Trp Asn Leu Glu Arg Phe Leu Glu Glu
                 45                  50                  55 ctc gac ggc gtc cct gca ccg gcg gcg agc ccg gac ggc gcg gcg att      426
Leu Asp Gly Val Pro Ala Pro Ala Ala Ser Pro Asp Gly Ala Ala Ile
             60                  65                  70 tac cct agc ccg atg ccg gcg gcg gcg gcg gag gcg gcg gcg cgc tgg      474
Tyr Pro Ser Pro Met Pro Ala Ala Ala Ala Glu Ala Ala Ala Arg Trp
         75                  80                  85 agt agg ggc tac ggc gat cgt gag gcg gtg ggg gtg atg ccc atg ccc      522
Ser Arg Gly Tyr Gly Asp Arg Glu Ala Val Gly Val Met Pro Met Pro
     90                  95                 100 gcg gcc gcg ctt ccg gcg gcg ccg gcg agc gcg gcg atg gac ccc gtg      570
Ala Ala Ala Leu Pro Ala Ala Pro Ala Ser Ala Ala Met Asp Pro Val
105             110                 115                 120 gag tac aac gcg atg ctg aag cgg aag ctg gac gag gac ctc gcc acc      618
Glu Tyr Asn Ala Met Leu Lys Arg Lys Leu Asp Glu Asp Leu Ala Thr
                125                 130                 135 gtc gcc atg tgg agg gcc tct ggt gca ata cat tct gag agt cct cta      666
Val Ala Met Trp Arg Ala Ser Gly Ala Ile His Ser Glu Ser Pro Leu
            140                 145                 150 ggc aat aaa aca tca ctg agt ata gtt ggt tcc atc ctg agt tca cag      714
Gly Asn Lys Thr Ser Leu Ser Ile Val Gly Ser Ile Leu Ser Ser Gln
        155                 160                 165 aag tgc att gaa ggt aac ggg ata cta gtg cag acc aag tta agt cct      762
Lys Cys Ile Glu Gly Asn Gly Ile Leu Val Gln Thr Lys Leu Ser Pro
    170                 175                 180 ggc cca aat gga gga tca ggc cca tat gta aat caa aat aca gat gct      810
Gly Pro Asn Gly Gly Ser Gly Pro Tyr Val Asn Gln Asn Thr Asp Ala
185                 190                 195                 200 cat gcc aag caa gct acg agt ggt tcc tca agg gag cca tca cca tca      858
His Ala Lys Gln Ala Thr Ser Gly Ser Ser Arg Glu Pro Ser Pro Ser
                205                 210                 215 gag gat gat gat atg gaa gga gat gca gag gca atg gga aat atg atc      906
Glu Asp Asp Asp Met Glu Gly Asp Ala Glu Ala Met Gly Asn Met Ile
            220                 225                 230 ctt gat gaa gaa gat aaa gtg aag aaa agg aag gaa tcc aac cgg gag      954
Leu Asp Glu Glu Asp Lys Val Lys Lys Arg Lys Glu Ser Asn Arg Glu
        235                 240                 245 tca gct aga cgc tca aga agc aga aag gca gct cgc cta aaa gac ctg     1002
Ser Ala Arg Arg Ser Arg Ser Arg Lys Ala Ala Arg Leu Lys Asp Leu
    250                 255                 260 gag gag cag gta tca cta tta agg gtt gaa aac tct tct ctg ttg agg     1050
Glu Glu Gln Val Ser Leu Leu Arg Val Glu Asn Ser Ser Leu Leu Arg
265                 270                 275                 280 cgt ctt gct gat gca aat cag aag tac agt gct gct gct att gac aat     1098
Arg Leu Ala Asp Ala Asn Gln Lys Tyr Ser Ala Ala Ala Ile Asp Asn
                285                 290                 295 agg gta cta atg gca gac att gaa gcc cta aga gca aag gtg agg atg     1146
Arg Val Leu Met Ala Asp Ile Glu Ala Leu Arg Ala Lys Val Arg Met
```

-continued

| | | | 300 | | | 305 | | | 310 | | | | |
|---|---|---|---|---|---|---|---|---|---|---|---|---|---|
| gca | gag | gag | agt | gtg | aag | atg | gtt | aca | ggg | gct | aga | caa ctt cac cag | 1194 |
| Ala | Glu | Glu | Ser | Val | Lys | Met | Val | Thr | Gly | Ala | Arg | Gln Leu His Gln | |
| | | | 315 | | | 320 | | | | 325 | | | |
| gcc | att | cct | gac | atg | caa | tct | ccc | ctc | aat | gtc | aac | tct gat gct tct | 1242 |
| Ala | Ile | Pro | Asp | Met | Gln | Ser | Pro | Leu | Asn | Val | Asn | Ser Asp Ala Ser | |
| | 330 | | | | 335 | | | | 340 | | | | |
| gtg | ccg | atc | cag | aac | aac | aac | cca | atg | aac | tac | ttc | tcc aac gct aac | 1290 |
| Val | Pro | Ile | Gln | Asn | Asn | Asn | Pro | Met | Asn | Tyr | Phe | Ser Asn Ala Asn | |
| 345 | | | | 350 | | | | 355 | | | | 360 | |
| aat | gcc | ggt | gtt | aac | agc | ttc | atg | cac | cag | gtt | tct | cca gcg ttc cag | 1338 |
| Asn | Ala | Gly | Val | Asn | Ser | Phe | Met | His | Gln | Val | Ser | Pro Ala Phe Gln | |
| | | | | 365 | | | | 370 | | | | 375 | |
| att | gtg | gat | tct | gtc | gag | aag | att | gac | cca | aca | gat | cca gtg cag ctg | 1386 |
| Ile | Val | Asp | Ser | Val | Glu | Lys | Ile | Asp | Pro | Thr | Asp | Pro Val Gln Leu | |
| | | | 380 | | | | 385 | | | | 390 | | |
| cag | cag | caa | cag | atg | gcg | agc | ttg | cag | cat | ctt | cag | aat aga gct tgt | 1434 |
| Gln | Gln | Gln | Gln | Met | Ala | Ser | Leu | Gln | His | Leu | Gln | Asn Arg Ala Cys | |
| | | 395 | | | | 400 | | | | 405 | | | |
| ggt | ggc | ggc | gca | agt | tcg | aat | gaa | tat | aca | gca | tgg | gga tcg tct ctg | 1482 |
| Gly | Gly | Gly | Ala | Ser | Ser | Asn | Glu | Tyr | Thr | Ala | Trp | Gly Ser Ser Leu | |
| | 410 | | | | 415 | | | | 420 | | | | |
| atg | gat | gca | aat | gag | ctt | gtc | aac | atg | gag | ctt | cag | tagtaggagc | 1528 |
| Met | Asp | Ala | Asn | Glu | Leu | Val | Asn | Met | Glu | Leu | Gln | | |
| 425 | | | | 430 | | | | 435 | | | | | |

| | |
|---|---|
| atatcctaac aacatgatga gagcatttgg aggtgcaaat ttgcaacctg caaatgctgt | 1588 |
| tttgtagtag tagttgttgt cgctgttttt gtctgaaact gtagtttcta tggattttgg | 1648 |
| acttgctgag gaacatctgc ggctgttgtt gtttcaaatt gagaaaatga gggacaatgg | 1708 |
| gacatggtgg tctcccttaa tatagcgaaa aaatggttgg ata | 1751 |

<210> SEQ ID NO 2
<211> LENGTH: 436
<212> TYPE: PRT
<213> ORGANISM: Oryza sativa

<400> SEQUENCE: 2

Met Glu His Val Phe Ala Val Asp Glu Ile Pro Asp Pro Leu Trp Ala
1               5                   10                  15

Pro Pro Pro Val Gln Pro Ala Ala Ala Gly Val Asp Asp Val
            20                  25                  30

Gly Ala Val Ser Gly Gly Leu Leu Glu Arg Cys Pro Ser Gly Trp
        35                  40                  45

Asn Leu Glu Arg Phe Leu Glu Glu Leu Asp Gly Val Pro Ala Pro Ala
    50                  55                  60

Ala Ser Pro Asp Gly Ala Ala Ile Tyr Pro Ser Pro Met Pro Ala Ala
65                  70                  75                  80

Ala Ala Glu Ala Ala Ala Arg Trp Ser Arg Gly Tyr Gly Asp Arg Glu
                85                  90                  95

Ala Val Gly Val Met Pro Met Pro Ala Ala Leu Pro Ala Ala Pro
            100                 105                 110

Ala Ser Ala Ala Met Asp Pro Val Glu Tyr Asn Ala Met Leu Lys Arg
        115                 120                 125

Lys Leu Asp Glu Asp Leu Ala Thr Val Ala Met Trp Arg Ala Ser Gly
    130                 135                 140

Ala Ile His Ser Glu Ser Pro Leu Gly Asn Lys Thr Ser Leu Ser Ile
145                 150                 155                 160

```
Val Gly Ser Ile Leu Ser Ser Gln Lys Cys Ile Glu Gly Asn Gly Ile
            165                 170                 175
Leu Val Gln Thr Lys Leu Ser Pro Gly Pro Asn Gly Gly Ser Gly Pro
        180                 185                 190
Tyr Val Asn Gln Asn Thr Asp Ala His Ala Lys Gln Ala Thr Ser Gly
    195                 200                 205
Ser Ser Arg Glu Pro Ser Pro Ser Glu Asp Asp Met Glu Gly Asp
210                 215                 220
Ala Glu Ala Met Gly Asn Met Ile Leu Asp Glu Glu Asp Lys Val Lys
225                 230                 235                 240
Lys Arg Lys Glu Ser Asn Arg Glu Ser Ala Arg Arg Ser Arg Ser Arg
            245                 250                 255
Lys Ala Ala Arg Leu Lys Asp Leu Glu Gln Val Ser Leu Leu Arg
        260                 265                 270
Val Glu Asn Ser Ser Leu Leu Arg Arg Leu Ala Asp Ala Asn Gln Lys
    275                 280                 285
Tyr Ser Ala Ala Ala Ile Asp Asn Arg Val Leu Met Ala Asp Ile Glu
    290                 295                 300
Ala Leu Arg Ala Lys Val Arg Met Ala Glu Glu Ser Val Lys Met Val
305                 310                 315                 320
Thr Gly Ala Arg Gln Leu His Gln Ala Ile Pro Asp Met Gln Ser Pro
            325                 330                 335
Leu Asn Val Asn Ser Asp Ala Ser Val Pro Ile Gln Asn Asn Pro
        340                 345                 350
Met Asn Tyr Phe Ser Asn Ala Asn Ala Gly Val Asn Ser Phe Met
    355                 360                 365
His Gln Val Ser Pro Ala Phe Gln Ile Val Asp Ser Val Glu Lys Ile
    370                 375                 380
Asp Pro Thr Asp Pro Val Gln Leu Gln Gln Gln Met Ala Ser Leu
385                 390                 395                 400
Gln His Leu Gln Asn Arg Ala Cys Gly Gly Gly Ala Ser Ser Asn Glu
            405                 410                 415
Tyr Thr Ala Trp Gly Ser Ser Leu Met Asp Ala Asn Glu Leu Val Asn
        420                 425                 430
Met Glu Leu Gln
        435

<210> SEQ ID NO 3
<211> LENGTH: 6335
<212> TYPE: DNA
<213> ORGANISM: Oryza sativa

<400> SEQUENCE: 3
tgctccattg cgctctcgga cgagcatata tgtatgacat gtgggcccgg aatgtcagta    60
acagggaatc ctgaaaaaaa tgcagctatg tgataatttt caacgctaat gttgcagttt   120
tctgaaaagt gtcgcaaagg ttgcagcaaa gtgatagttt agtcaataaa actgcagttt   180
tctgaaattt actctagttt ttttacctat ctagttggtt ttatgtgtaa ctaaacctta   240
catcagatca aaacaagttt ataaattcac cacgtatttc cctcagctca catctttctg   300
agaacatgat aaattcatta cattgtgcta caccatatgg ggactttaga acatgttcgt   360
cttctttttt tttctttttt cttttttaca tttaccttc tcagtttaca aatacttgtt   420
agctttgcct ggatatgtaa cccaacacta tgatacaaat tttgtcaatt ctctaaaatt   480
```

-continued

| | |
|---|---|
| tttcaagttt gaaacaaatt aagatgtatg gttgtgggtg aattaatcta cattgatagg | 540 |
| aaatgcgtta aagtacatgc aaagcttatg aaattattgc aagtagtcat catgcctcag | 600 |
| tgagtcagtg tgcatacttg tagtgcataa ccaaattctt tttcatatac tagaaagatt | 660 |
| caaagctgca aatgtgcatg tgaggttgat gaatggaata cacaataata catgacaata | 720 |
| aacacatatt aaagaattta gtgcaaaaaa attgtattgt catggtacac attttaacaa | 780 |
| ttttcttac ttttataca ttgtaaatat taattaatat ctaaaacaaa atataaagta | 840 |
| cgggaataaa atttaattgg ctaatgtgga aatggcatgg agctaaatgt tctatatatg | 900 |
| gtcctaacgt ttaaagataa aatacatatg tgcttgtgtt actaataata tctaaaagac | 960 |
| taagtagtat gtattaaata tgctagagaa cataagaaac ttaaaaactt gacgtggcaa | 1020 |
| aatgggcgct taagcgacac atattgcact ttcagctgat cttattcccc cttttaaatt | 1080 |
| tcatgtcccc attttgatta tcacatggaa tcaaccacat tatacctatg catccttgtg | 1140 |
| atttctgaaa ttaaactcga aagcaaccaa gtaaagagga gggggagaaa aagttagcag | 1200 |
| aaaacatgga tgatacatgt caataagctg ctagcataac cataagtgta gggcacgttt | 1260 |
| cttaggacaa tggtataaag ttacaaactg aaatatcatt gttaggtcag tttgatataa | 1320 |
| tcagtttgga ttactataga cacttgtcat agtaaataga gatggatcat ttcttaagta | 1380 |
| gcatcactac tcttattcac gaatgtcttt gctacccttt ctgttatact tttcctcttt | 1440 |
| ttctgtagaa agccatttgt ccttatatta tcattgtcaa attaaggatg cgtaatctac | 1500 |
| accctcactc aaaactttg ataagataaa acaaataaa tccatgcctt tatagaacct | 1560 |
| tgtcaaaatt atgctacacc tgtgctagga acaccatacc atcgtagctt acttgcacgc | 1620 |
| tttctgttag ccctttttcc taataaaaac gtattcgtcc gtatcgttgt tatcgctttg | 1680 |
| atcgtgtggg tttcactta tatccgttga aacctctgtt aacacgtcca aattatttat | 1740 |
| atcggtatta tcactcaaga tcgtgcgggt tgttttgctt tttacgtttc ttgaagcttc | 1800 |
| taaagagggg acaaacctat ataaatagga gaggagagca ccctctcaac tcagttcaaa | 1860 |
| attgaaaaaa aaagaaaaa aaagagaag aaaaaaaaac ccatgggttg cgtagccgta | 1920 |
| gctttcccac catttccttc tctccgaagc ctcctcctct ccgcttcctc ccgcgaaacc | 1980 |
| aaattccaaa gcatttgatc gaatttctcc caaacttttc cagcgttttc aatttcgccc | 2040 |
| cgatttcggt tcgaaaaccc ctcgcgaatt catttcaaac tcgtccgaga gcgcaatgga | 2100 |
| gcacgtgttc gccgtcgacg agatccccga cccgctgtgg gctccgccgc cgccggtgca | 2160 |
| gccggcggcg gccgccggag tagatgacgt cggcgcggtg agcggcggcg ggttgctgga | 2220 |
| gcggtgcccg tcggggtgga acctcgagag gtttctggag gagctcgacg gcgtccctgc | 2280 |
| accggcggca agcccggacg gcgcggcgat ttaccctagc ccgatgccgg cggcggcggc | 2340 |
| ggaggcggcg gcgcgctgga gtaggggcta cggcgatcgt gaggcggtgg gggtgatgcc | 2400 |
| catgcccgcg gccgcgcttc cggcggcgcc ggcgagcgcg gcgatggacc ccgtggagta | 2460 |
| caacgcgatg ctgaagcgga agctggacga ggacctcgcc accgtcgcca tgtggagggt | 2520 |
| actctctctc atctcgatcg ctgcttgctt tgcttgcttc atggcttgta cagttgtact | 2580 |
| ggtgggttca ccatttgggg tggtggtgat gggatggctg tggcgtaatt aagtgcaatt | 2640 |
| tttagggcat ttcctgtgat taactgtggc tagatggtcg caatttagca tagatgtgac | 2700 |
| atatcctagc tgttactatg aatctggacc ggctctctgt ccagattcat agtactagat | 2760 |
| gtgtcacatc cctctaaatc tcttatatta taaggaggga gtataaatta attttataag | 2820 |
| agcacgcgtt gatgtcgata tccgcatcgt aagcccaggc actactcacg tgtgtgcttt | 2880 |

-continued

```
cttatccata ctttaatatt gtcagagtgg gatgagacaa actttaatat tgtcggggtg    2940
tggtataata tttatattat ttccgtgtat agatttagga gtaatatgga ttaggattgc    3000
atggaggtgc agagacttta tgtgacttct tggagccgtg cattgcttga gtgcaaagtt    3060
aacaatttgg ttacatgttg caaaaatgat gtatagatca taggtcattg cacttatttt    3120
gggtggtcct aggcggtatg attcatgaaa tattttttgg aaattctgta ttttaccata    3180
tttgcattac ttttcttatt attgttgttt gaaggaatta ttaggtcaca taccttgga    3240 agatgaaatt attttagtag aaaaaaagaa actgttatat tggaatctgg taaatttgga    3300
cctagaaatt ctcaccagtc gattgtagat ggggaagcag agctttcttt ttagagattt    3360
gctccgctcc aacaaaaagt acctcgaggt actggtacct catggtacca aatcgtttcc    3420
gatcgttgga tctaacaatg cacatcctgc ctaattagat ccaacgatcg aaaatgattt    3480
ggtaccgtga gtaccggta cctcgaggta ctttttgttg gaccggagaa aatatcttct    3540
ttttatgtta gttttctaag tggggtatat aattttttgca attggatatc atactttgaa    3600
ctcattatgt gggttcagtt tacaaatgac tacagaacat gttgatctga gcttttgcta    3660
gttgatttca gtttacaatg tgaaacggtt ccctatataa gattataatg ccattagaac    3720
taattaacta tgagagtgtg tgtttagctc cgatagttat taagtcccctt tgcattctga    3780 cttcaatttt tggcatgtcc atccatccac aggcctctgg tgcaatacat tctgagagtc    3840
ctctaggcaa taaacatca ctgagtatag ttggttccat cctgagttca cagaagtgca    3900
ttgaaggtat tctattatgc atatgtgctt agttaaatct tctcagtacc tatgagttat    3960
gacttatgag taatctctaa tgttgtaagc aaatctaatt tttgcgtaat gtagttttca    4020
tattatatat atctgattgg attttccccc tatttcgaca cattcaggta acgggatact    4080
agtgcagacc aagttaagtc ctggcccaaa tggaggatca ggcccatatg taaatcaaaa    4140
tacagatgct catgccaagc aagctacgag tggttcctca agggagccat caccatcaga    4200
ggatgatgat atggaaggag atgcagaggc aatgggaaat atgatccttg atgaagaaga    4260
taaagtgaag aaaaggtaat atgtattctt ttgcttgtgt attttttattt ttcaattcaa    4320 cacatacaaa gagtaaacac tgagcattag cattagaaat taggggactt ttacatctat    4380
tgatttcctt ttttcttaga aatagctttt aagtaatatg ctttagatta tcaagataat    4440
ggatccttag tttctttcta ggtgtttcat gtttgtactg gatgtatttg attatataca    4500
acattctcac ttttttctta gaaatgcttg agctaatgct tgctaggtgt ttcaatgctt    4560
tatatacctg actgaatttt ggtaatgctt gttacaagct ggtgcattaa ggataattat    4620
tgtttccgtg caagcagcta ttcatgcaaa aaaggaaaaa tgcaacgtgt atgattagaa    4680
caatttagga ggcatttgct tcttgctttt cataacatgc tgggaatatc atgtcctgtt    4740
gtgtctagtt gctttttcta catatgaaaa attgagttta tctactgtgg tctttttttc    4800
cgcagcagtc agacattcat gtcgcctttt tttgtgtaat aaatacagcc ggatatttga    4860
gatttgagct tgtgttcttg tccaatttca ggaaggaatc caaccgggag tcagctagac    4920
gctcaagaag cagaaaggca gctcgcctaa aagacctgga ggagcaggtt ttgtgtttta    4980
cactattcca tttgactgca caacaaagtt tggaatatg taagtaacaa gtgtaattgt    5040
tgctaaatca ttgcaggtat cactattaag ggttgaaaac tcttctctgt tgaggcgtct    5100
tgctgatgca aatcagaagt acagtgctgc tgctattgac aatagggtac taatggcaga    5160
cattgaagcc ctaagagcaa aggtatgcaa ctgtttaagt gccttttagt cctctgtatg    5220
```

-continued

| | |
|---|---|
| aactgaacct ctctttcaaa taggtatcca attatccatg tgcattgatt ctggtcagta | 5280 |
| ttgtgcatct ttcatggtgt agaaaaccgg aatattctac atatcaaaca tataccaaat | 5340 |
| tttcttggaa tgaaacgaac ttctagcatt tgttcttaaa atttggtaca ggagatattg | 5400 |
| caaatgttgt cctcttgctc cattcgaagg attaagttgt ttgccatcta ttataacctg | 5460 |
| caacaattag actcacttgt tttgtcttga acaaccggg tgtaactact tttctttttc | 5520 |
| ctgcaacgta ccaggtgtaa ataatcgctt gccgaatggt gataaccaat tcacacaatg | 5580 |
| gatcacaatc aattttaaca aagaacctga gctacactac actactgcgg tgtcgtatct | 5640 |
| tatagccata tgcttctaga ccacaactga aaattcatga accatgcgat gtgggttagc | 5700 |
| taacatcttg acatgattgc aggtgaggat ggcagaggag agtgtgaaga tggttacagg | 5760 |
| ggctagacaa cttcaccagg ccattcctga catgcaatct cccctcaatg tcaactctga | 5820 |
| tgcttctgtg ccgatccaga acaacaaccc aatgaactac ttctccaacg ctaacaatgc | 5880 |
| cggtgttaac agcttcatgc accaggtttc tccagcgttc cagattgtgg attctgtcga | 5940 |
| gaagattgac ccaacagatc cagtgcagct gcagcagcaa cagatggcga gcttgcagca | 6000 |
| tcttcagaat agagcttgtg gtggcggcgc aagttcgaat gaatatacag catggggatc | 6060 |
| gtctctgatg gatgcaaatg agcttgtcaa catggagctt cagtagtagg agcatatcct | 6120 |
| aacaacatga tgagagcatt tggaggtgca aatttgcaac ctgcaaatgc tgttttgtag | 6180 |
| tagtagttgt tgtcgctgtt tttgtctgaa actgtagttt ctatggattt tggacttgct | 6240 |
| gaggaacatc tgcggctgtt gttgtttcaa attgagaaaa tgagggacaa tgggacatgg | 6300 |
| tggtctccct taatatagcg aaaaatggtt ggaat | 6335 |

<210> SEQ ID NO 4
<211> LENGTH: 1199
<212> TYPE: DNA
<213> ORGANISM: Oryza sativa
<220> FEATURE:
<221> NAME/KEY: CDS
<222> LOCATION: (171)..(1004)

<400> SEQUENCE: 4

| | |
|---|---|
| ggcacgaggc gatcaacaca aaagcttct ctttcccttc tcctcctcgg tgatctgtct | 60 |
| cgccggggca tctcgaaaag catccgactc cgacgccgcc gcgcgccacc acccggccga | 120 |
| tcgccgacgc cgcagccgct ggaagcagca gggacgacgg agaatcggag atg gac | 176 |
| | Met Asp |
| | 1 |

| | |
|---|---|
| atc gag gcg ttc atc cac ggc gga agc ggg ggc ggc gac gcc gac gcc<br>Ile Glu Ala Phe Ile His Gly Gly Ser Gly Gly Gly Asp Ala Asp Ala<br>     5               10               15 | 224 |
| gac cac ccg ctc ggc atc ttc tcc gcc gcc gac ctc tcc ggc ttc ggc<br>Asp His Pro Leu Gly Ile Phe Ser Ala Ala Asp Leu Ser Gly Phe Gly<br> 20                25               30 | 272 |
| ttc gcg gac tcg agc acc atc aca ggg ggc att ccc aat cac ata tgg<br>Phe Ala Asp Ser Ser Thr Ile Thr Gly Gly Ile Pro Asn His Ile Trp<br>35           40           45          50 | 320 |
| ccc cag tcc cag aac ctg aac gca cgg cat cct gcg gtc tcc acg aca<br>Pro Gln Ser Gln Asn Leu Asn Ala Arg His Pro Ala Val Ser Thr Thr<br>           55           60          65 | 368 |
| att gag tcg cag tca tca atc tgt gca gca gca agt ccc aca tca gct<br>Ile Glu Ser Gln Ser Ser Ile Cys Ala Ala Ala Ser Pro Thr Ser Ala<br>    70              75               80 | 416 |
| acc aat ctg aac atg aag gag agc caa act ctg gga ggc aca agt ggt<br>Thr Asn Leu Asn Met Lys Glu Ser Gln Thr Leu Gly Gly Thr Ser Gly | 464 |

-continued

```
              85                  90                  95
tcg gat tct gaa agt gaa tcg ctg ttg gat ata gag ggt ggt cca tgc     512
Ser Asp Ser Glu Ser Glu Ser Leu Leu Asp Ile Glu Gly Gly Pro Cys
        100                 105                 110 gaa caa agc acg aac ccg ttg gac gtg aag aga gtg aga agg atg gtg     560
Glu Gln Ser Thr Asn Pro Leu Asp Val Lys Arg Val Arg Arg Met Val
115                 120                 125                 130 tcc aat cgg gag tct gct cgg cga tcg agg aag aga aag caa gct cac     608
Ser Asn Arg Glu Ser Ala Arg Arg Ser Arg Lys Arg Lys Gln Ala His
                135                 140                 145 tta gct gat ctc gag tca cag gtt gac cag ctc cgg ggc gaa aac gca     656
Leu Ala Asp Leu Glu Ser Gln Val Asp Gln Leu Arg Gly Glu Asn Ala
            150                 155                 160 tcg ctt ttc aag cag ttg acg gat gcc aac cag caa ttc aca act tct     704
Ser Leu Phe Lys Gln Leu Thr Asp Ala Asn Gln Gln Phe Thr Thr Ser
        165                 170                 175 gtc acg gac aac aga atc ctc aaa tca gac gtt gag gcc ctc cgg gtc     752
Val Thr Asp Asn Arg Ile Leu Lys Ser Asp Val Glu Ala Leu Arg Val
    180                 185                 190 aag gtg aag atg gcg gag gac atg gtg gcg cgg ggg gcg ctg tcg tgc     800
Lys Val Lys Met Ala Glu Asp Met Val Ala Arg Gly Ala Leu Ser Cys
195                 200                 205                 210 ggg ctc ggc cac ctg ggc ggg ctg tcg ccg gcg ctg aac ccc cgg cag     848
Gly Leu Gly His Leu Gly Gly Leu Ser Pro Ala Leu Asn Pro Arg Gln
                215                 220                 225 gcg tgc cgc gtc ccc gac gtg ctc gcc ggc ctg gac tac gcc ggc gac     896
Ala Cys Arg Val Pro Asp Val Leu Ala Gly Leu Asp Tyr Ala Gly Asp
            230                 235                 240 gac ccc ttc acg gcc ggg ctg tcc cag ccg gag cag ttg cag atg ccc     944
Asp Pro Phe Thr Ala Gly Leu Ser Gln Pro Glu Gln Leu Gln Met Pro
        245                 250                 255 ggc ggc gag gtg gtt gac gcc tgg ggc tgg gac aac cac ccc aac ggc     992
Gly Gly Glu Val Val Asp Ala Trp Gly Trp Asp Asn His Pro Asn Gly
    260                 265                 270 ggc atg tcc aag tgaaactact ggtcctactt ctatgtcagc tcagctacgt         1044
Gly Met Ser Lys
275 ttgaaacgtg atgtgtccaa gtgaacggac ttgagttttt cagagtcctc gtgtcgaagt  1104 gtcatgcact cttccctatt cctgtaatag aactgactag ctaagagact gaaagtctga  1164 aactacgaag tataaatgtg gtggaatttg gaact                             1199
```

<210> SEQ ID NO 5
<211> LENGTH: 278
<212> TYPE: PRT
<213> ORGANISM: Oryza sativa

<400> SEQUENCE: 5

Met Asp Ile Glu Ala Phe Ile His Gly Ser Gly Gly Gly Asp Ala
1               5                   10                  15

Asp Ala Asp His Pro Leu Gly Ile Phe Ser Ala Ala Asp Leu Ser Gly
            20                  25                  30

Phe Gly Phe Ala Asp Ser Ser Thr Ile Thr Gly Gly Ile Pro Asn His
        35                  40                  45

Ile Trp Pro Gln Ser Gln Asn Leu Asn Ala Arg His Pro Ala Val Ser
    50                  55                  60

Thr Thr Ile Glu Ser Gln Ser Ser Ile Cys Ala Ala Ala Ser Pro Thr
65                  70                  75                  80

-continued

```
Ser Ala Thr Asn Leu Asn Met Lys Glu Ser Gln Thr Leu Gly Gly Thr
                85                  90                  95

Ser Gly Ser Asp Ser Glu Ser Glu Ser Leu Leu Asp Ile Glu Gly Gly
            100                 105                 110

Pro Cys Glu Gln Ser Thr Asn Pro Leu Asp Val Lys Arg Val Arg Arg
        115                 120                 125

Met Val Ser Asn Arg Glu Ser Ala Arg Arg Ser Arg Lys Arg Lys Gln
    130                 135                 140

Ala His Leu Ala Asp Leu Glu Ser Gln Val Asp Gln Leu Arg Gly Glu
145                 150                 155                 160

Asn Ala Ser Leu Phe Lys Gln Leu Thr Asp Ala Asn Gln Gln Phe Thr
                165                 170                 175

Thr Ser Val Thr Asp Asn Arg Ile Leu Lys Ser Asp Val Glu Ala Leu
            180                 185                 190

Arg Val Lys Val Lys Met Ala Glu Asp Met Val Ala Arg Gly Ala Leu
        195                 200                 205

Ser Cys Gly Leu Gly His Leu Gly Gly Leu Ser Pro Ala Leu Asn Pro
    210                 215                 220

Arg Gln Ala Cys Arg Val Pro Asp Val Leu Ala Gly Leu Asp Tyr Ala
225                 230                 235                 240

Gly Asp Asp Pro Phe Thr Ala Gly Leu Ser Gln Pro Glu Gln Leu Gln
                245                 250                 255

Met Pro Gly Gly Glu Val Val Asp Ala Trp Gly Trp Asp Asn His Pro
            260                 265                 270

Asn Gly Gly Met Ser Lys
        275

<210> SEQ ID NO 6
<211> LENGTH: 1362
<212> TYPE: DNA
<213> ORGANISM: Oryza sativa
<220> FEATURE:
<221> NAME/KEY: CDS
<222> LOCATION: (23)..(907)

<400> SEQUENCE: 6
ggcacgaggt cggaggaagg cg atg atg aag aag tgc ccg tcg gag ctg cag        52
                         Met Met Lys Lys Cys Pro Ser Glu Leu Gln
                           1               5                  10 ctg gag gcg ttc atc cgg gag gag gcc ggc gcc ggc gac cgc aag ccc        100
Leu Glu Ala Phe Ile Arg Glu Glu Ala Gly Ala Gly Asp Arg Lys Pro
             15                  20                  25 ggc gtg tta tct ccc ggc gac ggc gcg cgt aag tcc ggc ctg ttc tct        148
Gly Val Leu Ser Pro Gly Asp Gly Ala Arg Lys Ser Gly Leu Phe Ser
         30                  35                  40 ccc ggc gac ggc gag atg tcc gtg ttg gat cag agt aca ctg gac gga        196
Pro Gly Asp Gly Glu Met Ser Val Leu Asp Gln Ser Thr Leu Asp Gly
     45                  50                  55 agc ggc ggc ggc cac cag ctg tgg tgg ccg gag agc gtc cgt acg ccg        244
Ser Gly Gly Gly His Gln Leu Trp Trp Pro Glu Ser Val Arg Thr Pro
 60                  65                  70 ccg cgc gcc gcc gcc gcc ttc tcg gcc acg gcc gac gag cgg acg ccg        292
Pro Arg Ala Ala Ala Ala Phe Ser Ala Thr Ala Asp Glu Arg Thr Pro
75                  80                  85                  90 gcg tcc atc tcc gat gac ccc aaa cca acc acc tca gcg aac cac gcg        340
Ala Ser Ile Ser Asp Asp Pro Lys Pro Thr Thr Ser Ala Asn His Ala
                 95                 100                 105 cct gaa agc gac tcg gac tcc gat tgc gat tcg ctg tta gaa gca gag        388
```

```
Pro Glu Ser Asp Ser Asp Ser Asp Cys Asp Ser Leu Leu Glu Ala Glu
            110                 115                 120 agg agt cca cgc ctg cgt ggc acg aaa tcc aca gaa aca aag cga ata        436
Arg Ser Pro Arg Leu Arg Gly Thr Lys Ser Thr Glu Thr Lys Arg Ile
        125                 130                 135 aga agg atg gtg tcc aac agg gag tcc gct cga cga tcc agg agg aga        484
Arg Arg Met Val Ser Asn Arg Glu Ser Ala Arg Arg Ser Arg Arg Arg
    140                 145                 150 aag cag gca cag tta tct gaa ctc gaa tca cag gtc gag caa ctc aaa        532
Lys Gln Ala Gln Leu Ser Glu Leu Glu Ser Gln Val Glu Gln Leu Lys
155                 160                 165                 170 ggc gaa aac tca tcc ctc ttc aag cag ctc aca gag tcc agc cag cag        580
Gly Glu Asn Ser Ser Leu Phe Lys Gln Leu Thr Glu Ser Ser Gln Gln
                175                 180                 185 ttc aat aca gcg gtc acg gac aac agg atc ctc aaa tcg gat gta gag        628
Phe Asn Thr Ala Val Thr Asp Asn Arg Ile Leu Lys Ser Asp Val Glu
            190                 195                 200 gcc tta aga gtc aag gtc aag atg gct gaa gac atg gtc gcg agg gcc        676
Ala Leu Arg Val Lys Val Lys Met Ala Glu Asp Met Val Ala Arg Ala
        205                 210                 215 gcg atg tcg tgt ggc ctg ggc cag ctc ggg ctg gcg cca ttg ctc agc        724
Ala Met Ser Cys Gly Leu Gly Gln Leu Gly Leu Ala Pro Leu Leu Ser
    220                 225                 230 tcc agg aag atg tgc caa gct ttg gat atg ctc agt tta cca cgg aac        772
Ser Arg Lys Met Cys Gln Ala Leu Asp Met Leu Ser Leu Pro Arg Asn
235                 240                 245                 250 gat gcc tgt ggt ttc aaa ggc ttg aac ctg ggt cga cag gtt cag aac        820
Asp Ala Cys Gly Phe Lys Gly Leu Asn Leu Gly Arg Gln Val Gln Asn
                255                 260                 265 tca ccg gtt caa agc gct gca agc cta gag agc ctg gac aac cgg ata        868
Ser Pro Val Gln Ser Ala Ala Ser Leu Glu Ser Leu Asp Asn Arg Ile
            270                 275                 280 tcc agc gag gtg acc agc tgc tcg gct gat gtg tgg cct taagacactt        917
Ser Ser Glu Val Thr Ser Cys Ser Ala Asp Val Trp Pro
        285                 290                 295 catccgtgtt cgagagagct tgagattcta agaagcagcc ggtgagaatc tgaaaaggct    977
agttgttcag tttcctattt ttagtttatg tttgaattct ctggctacta atgctcaaaa   1037
tctgggagag aatctaaatc gtttgggaca gataaaaaat tatgcgagaa ggtgtagctg   1097
acagaaacct tcccaaacaa atctccatca gaacctatat gtaaagtaat acggtatcct   1157
ctgttactag gtgcatgtgc ataactgaca agctgctaag tactaggtac tacagtctga   1217
ggcaagtatt tctggtgttt tggtgctgaa gaactatgtt ttagtgcgtt tgatctgcgg   1277
caatcaaggc catctgatcg aaatttgatt ggtataaatc tgatcgaaat ttgattggta   1337
taagtataat agtttgattt tgatc                                         1362

<210> SEQ ID NO 7
<211> LENGTH: 295
<212> TYPE: PRT
<213> ORGANISM: Oryza sativa

<400> SEQUENCE: 7

Met Met Lys Lys Cys Pro Ser Glu Leu Gln Leu Glu Ala Phe Ile Arg
1               5                   10                  15

Glu Glu Ala Gly Ala Gly Asp Arg Lys Pro Gly Val Leu Ser Pro Gly
            20                  25                  30

Asp Gly Ala Arg Lys Ser Gly Leu Phe Ser Pro Gly Asp Gly Glu Met
        35                  40                  45
```

```
Ser Val Leu Asp Gln Ser Thr Leu Asp Gly Ser Gly Gly His Gln
 50                  55                 60

Leu Trp Trp Pro Glu Ser Val Arg Thr Pro Arg Ala Ala Ala Ala
 65                  70                  75                  80

Phe Ser Ala Thr Ala Asp Glu Arg Thr Pro Ala Ser Ile Ser Asp Asp
                 85                  90                  95

Pro Lys Pro Thr Thr Ser Ala Asn His Ala Pro Glu Ser Asp Ser Asp
                100                 105                 110

Ser Asp Cys Asp Ser Leu Leu Glu Ala Glu Arg Ser Pro Arg Leu Arg
            115                 120                 125

Gly Thr Lys Ser Thr Glu Thr Lys Arg Ile Arg Met Val Ser Asn
130                 135                 140

Arg Glu Ser Ala Arg Arg Ser Arg Arg Arg Lys Gln Ala Gln Leu Ser
145                 150                 155                 160

Glu Leu Glu Ser Gln Val Glu Gln Leu Lys Gly Glu Asn Ser Ser Leu
                165                 170                 175

Phe Lys Gln Leu Thr Glu Ser Ser Gln Gln Phe Asn Thr Ala Val Thr
                180                 185                 190

Asp Asn Arg Ile Leu Lys Ser Asp Val Glu Ala Leu Arg Val Lys Val
            195                 200                 205

Lys Met Ala Glu Asp Met Val Ala Arg Ala Met Ser Cys Gly Leu
210                 215                 220

Gly Gln Leu Gly Leu Ala Pro Leu Leu Ser Ser Arg Lys Met Cys Gln
225                 230                 235                 240

Ala Leu Asp Met Leu Ser Leu Pro Arg Asn Asp Ala Cys Gly Phe Lys
                245                 250                 255

Gly Leu Asn Leu Gly Arg Gln Val Gln Asn Ser Pro Val Gln Ser Ala
                260                 265                 270

Ala Ser Leu Glu Ser Leu Asp Asn Arg Ile Ser Ser Glu Val Thr Ser
            275                 280                 285

Cys Ser Ala Asp Val Trp Pro
290                 295

<210> SEQ ID NO 8
<211> LENGTH: 12
<212> TYPE: DNA
<213> ORGANISM: Oryza sativa

<400> SEQUENCE: 8
gctgagtcat ga                                                         12

<210> SEQ ID NO 9
<211> LENGTH: 12
<212> TYPE: DNA
<213> ORGANISM: Oryza sativa

<400> SEQUENCE: 9
catgagtcac tt                                                         12

<210> SEQ ID NO 10
<211> LENGTH: 12
<212> TYPE: DNA
<213> ORGANISM: Oryza sativa

<400> SEQUENCE: 10
agtgagtcac tt                                                         12
```

```
<210> SEQ ID NO 11
<211> LENGTH: 12
<212> TYPE: DNA
<213> ORGANISM: Oryza sativa

<400> SEQUENCE: 11
ggtgagtcat at                                                         12

<210> SEQ ID NO 12
<211> LENGTH: 12
<212> TYPE: DNA
<213> ORGANISM: Oryza sativa

<400> SEQUENCE: 12
ggtgagtcat gt                                                         12

<210> SEQ ID NO 13
<211> LENGTH: 12
<212> TYPE: DNA
<213> ORGANISM: Oryza sativa

<400> SEQUENCE: 13
gatgagtcat gc                                                         12

<210> SEQ ID NO 14
<211> LENGTH: 12
<212> TYPE: DNA
<213> ORGANISM: Oryza sativa

<400> SEQUENCE: 14
aatgagtcat ca                                                         12

<210> SEQ ID NO 15
<211> LENGTH: 12
<212> TYPE: DNA
<213> ORGANISM: Oryza sativa

<400> SEQUENCE: 15
agccacgtca ca                                                         12

<210> SEQ ID NO 16
<211> LENGTH: 17
<212> TYPE: DNA
<213> ORGANISM: Artificial Sequence
<220> FEATURE:
<223> OTHER INFORMATION: Description of Artificial Sequence:
      Artificially Synthesized Primer Sequence
<220> FEATURE:
<221> NAME/KEY: misc_feature
<222> LOCATION: (9)
<223> OTHER INFORMATION: This nucleotide residue is an inosine.
<220> FEATURE:
<221> NAME/KEY: misc_feature
<222> LOCATION: (15)
<223> OTHER INFORMATION: This nucleotide residue is an inosine.

<400> SEQUENCE: 16
tccaaymgng arwcngc                                                    17

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence:
      Artificially Synthesized Primer Sequence
```

```
<400> SEQUENCE: 17
gtcctcygcc atcttcacct t                                             21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 18
atgggttgcg tagccgtagc t                                             21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 19
ttgcttggca tgagcatctg t                                             21

<210> SEQ ID NO 20
<211> LENGTH: 17
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 20
gaggatcagg cccatat                                                  17

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 21
tcgctatatt aagggagacc a                                             21

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 22
tgctccattg cgctctcgga cgag                                          24

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence:
      Artificially Synthesized Primer Sequence
```

```
<400> SEQUENCE: 23
atgaattcgc gagggqtttt cga                                              23

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 24
gtttgggaga aattcgatca aatgc                                            25

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 25
atggtatggt gttcctagca caggtgtagc                                       30

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 26
aaaactgcag ttttctga                                                    18

<210> SEQ ID NO 27
<211> LENGTH: 25
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 27
aatggatccg cgagggqttt tcgaa                                            25

<210> SEQ ID NO 28
<211> LENGTH: 12
<212> TYPE: DNA
<213> ORGANISM: Oryza sativa

<400> SEQUENCE: 28
gcttcctcat ga                                                          12

<210> SEQ ID NO 29
<211> LENGTH: 26
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 29
aaccatggtg ctggagcggt gcccgt                                           26
```

```
<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 30
aaccatggcg gcggaggcgg cggcg                                        25

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 31
ccccatggag tacaacgcga tgc                                          23

<210> SEQ ID NO 32
<211> LENGTH: 25
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 32
aaccatggtt ggttccatcc tgagt                                        25

<210> SEQ ID NO 33
<211> LENGTH: 25
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 33
aaccatggct catgccaagc aagct                                        25

<210> SEQ ID NO 34
<211> LENGTH: 28
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 34
aaccatggat gaagaagata aagtgaag                                     28

<210> SEQ ID NO 35
<211> LENGTH: 26
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 35
taggatccgc tcctactact gaagct                                       26
```

```
<210> SEQ ID NO 36
<211> LENGTH: 27
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 36
aaggatccaa tggagcacgt gttcgcc                                27

<210> SEQ ID NO 37
<211> LENGTH: 26
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 37
aaggatccgg cggcggaggc ggcgcg                                 26

<210> SEQ ID NO 38
<211> LENGTH: 27
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 38
gccggatcca gttggttcca tcctgag                                27

<210> SEQ ID NO 39
<211> LENGTH: 26
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 39
aaggatcctg atgaagaaga taaagt                                 26

<210> SEQ ID NO 40
<211> LENGTH: 27
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 40
aaggatccag gagtagatga cgtcggc                                27

<210> SEQ ID NO 41
<211> LENGTH: 29
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 41
aaggatccag acgagatccc cgacccgct                              29

<210> SEQ ID NO 42
```

```
<211> LENGTH: 28
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 42
tagagctcta cgccgccggc atcgggct                                       28

<210> SEQ ID NO 43
<211> LENGTH: 28
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 43
tagagctcta aaggatcata tttcccat                                       28

<210> SEQ ID NO 44
<211> LENGTH: 28
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 44
tagagctcta ggcggccgcc gccggctg                                       28

<210> SEQ ID NO 45
<211> LENGTH: 28
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 45
tagagctcta cggcggcggc ggagccca                                       28

<210> SEQ ID NO 46
<211> LENGTH: 25
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 46
aaaccatgga gcacgtgttc gccgt                                          25

<210> SEQ ID NO 47
<211> LENGTH: 26
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 47
taggatccgc tcctactact gaagct                                         26

<210> SEQ ID NO 48
<211> LENGTH: 26
```

```
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 48
aaaccatgga gggagaagct gagacc                                      26

<210> SEQ ID NO 49
<211> LENGTH: 30
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 49
aaaggatcct acatatcaga agcggcggga                                  30

<210> SEQ ID NO 50
<211> LENGTH: 26
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 50
aaaccatgga tatagagggc ggtcca                                      26

<210> SEQ ID NO 51
<211> LENGTH: 30
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 51
aaaggatcct acagcccgcc caggtggccg                                  30

<210> SEQ ID NO 52
<211> LENGTH: 21
<212> TYPE: DNA
<213> ORGANISM: Oryza sativa

<400> SEQUENCE: 52
gtttgtcatg gctgagtcat g                                           21
```

The invention claimed is:

1. An isolated nucleic acid molecule comprising:
a) the coding region of SEQ ID NO:1, or SEQ ID NO:3; or
b) a DNA encoding SEQ ID NO:2.

2. The nucleic acid molecule of claim 1, which encodes a protein that binds to the GCN4 motif or activates expression of a rice seed storage protein.

3. The nucleic acid molecule of claim 1, which is derived from a rice plant.

4. A vector comprising the nucleic acid molecule of claim 1.

5. An isolated nucleic acid molecule encoding an antisense RNA complementary to the full-length transcription product of a nucleic acid sequence, and wherein said nucleic acid sequence comprises:
a) the coding region of SEQ ID NO:1, or SEQ ID NO:3; or
b) a DNA encoding SEQ ID NO:2.

6. A method of producing a protein, comprising the steps of culturing a transformed cell, and collecting the protein expressed from said transformed cell or from the supernatant of said transformed cell, and wherein said protein comprises:
a) the amino acid sequence encoded by SEQ ID NO:1, or SEQ ID NO:3; or b) the amino acid sequence of SEQ ID NO:2.

7. A transformed cell comprising a nucleic acid sequence comprising:
   a) the coding region of SEQ ID NO:1, or SEQ ID NO:3; or
   b) a DNA encoding SEQ ID NO:2.

8. The transformed cell of claim 7, which is a plant cell.

9. A plant which is derived from the transformed cell of claim 8, wherein said plant comprises said nucleic acid sequence.

10. A plant derived from a progeny of, or a clone of the plant of claim 9, wherein said derived plant comprises said nucleic acid sequence.

11. A reproductive material of the plant of claim 9, wherein said reproductive material comprises said nucleic acid sequence.

12. A reproductive material of the plant of claim 10, wherein said reproductive material comprises said nucleic acid sequence.

13. A plant which comprises
   a) a first nucleic acid construct comprising;
      i) a first expression control region, and
      ii) a first nucleic acid sequence downstream of said first expression control region, wherein said first nucleic acid sequence comprises:
         A) the coding region of SEQ ID NO:1, or SEQ ID NO:3; or
         B) a DNA encoding SEQ ID NO:2; and
   b) a second nucleic acid construct comprising;
      i) a second expression control region having the target sequence of a protein encoded by said first nucleic acid sequence, and
      ii) a foreign nucleic acid sequence downstream of said second expression control region.

14. The plant of claim 13, wherein said target sequence comprises the GCN4 motif.

15. The plant of claim 14, wherein said GCN4 motif comprises the sequence as set forth in SEQ ID NO:8, SEQ ID NO:13, or SEQ ID NO:14.

16. The plant of claim 13, wherein said target sequence comprises a G/C box.

17. A method of producing the plant of claim 13, wherein said method comprises a step of crossing a first plant with a second plant, wherein said first plant comprises:
   a) a first nucleic acid construct comprising;
      i) a first expression control region, and
      ii) a first nucleic acid sequence downstream of said first expression control region, wherein said first nucleic acid sequence comprises:
         A) the coding region of a DNA as set forth in SEQ ID NO:1, or SEQ ID NO:3; or
         B) a DNA encoding SEQ ID NO:2; and
   wherein said second plant comprises:
   b) a second nucleic acid construct comprising;
      i) a second expression control region having the target sequence of a protein encoded by said first nucleic acid sequence, and
      ii) a foreign nucleic acid sequence downstream of said second expression control region.

18. An isolated nucleic acid encoding a protein having a sequence at least 95% identical to SEQ ID NO:2, wherein said protein binds to the GCN4 motif and activates expression of a rice seed storage protein.

* * * * *

UNITED STATES PATENT AND TRADEMARK OFFICE
CERTIFICATE OF CORRECTION

PATENT NO.        : 7,214,851 B2
APPLICATION NO. : 10/149553
DATED             : May 8, 2007
INVENTOR(S)       : Fumio Takaiwa It is certified that error appears in the above-identified patent and that said Letters Patent is hereby corrected as shown below:

Sequence Listing

Delete the sequence listing in its entirety, and substitute the attached sequence listing therefor Signed and Sealed this Twenty-fourth Day of June, 2008

JON W. DUDAS
*Director of the United States Patent and Trademark Office*

SEQUENCE LISTING

<110> Takaiwa, Fumio
      Onodera, Yasuyuki

<120> bZip Transcription Factor that Controls Expression of the Storage
      Protein in the Rice Plant

<130> SHIMIZU-07053

<140> 10/149,553
<141> 2002-12-19

<160> 91

<170> PatentIn version 3.3

<210> 1
<211> 1751
<212> DNA
<213> Oryza sativa

<220>
<221> CDS
<222> (211)..(1518)

<400> 1
ggcacgagaa aaaacccatg ggttgcgtag ccgtagcttt cccaccattt ccttctctcc      60
gaagcctcct cctctccgct tcctcccgcg aaaccaaatt ccaaagcatt tgatcgaatt     120
tctcccaaac ttttccagcg ttttcaattt cgccccgatt tcggttcgaa accccctcgc     180
gaattcattt caaactcgtc cgagagcgca atg gag cac gtg ttc gcc gtc gac     234
                                  Met Glu His Val Phe Ala Val Asp
                                   1               5 gag atc ccc gac ccg ctg tgg gct ccg ccg ccg gtg cag ccg gcg              282
Glu Ile Pro Asp Pro Leu Trp Ala Pro Pro Pro Val Gln Pro Ala
     10              15                  20 gcg gcc gcc gga gta gat gac gtc ggc gcg gtg agc ggc ggc ggg ttg         330
Ala Ala Ala Gly Val Asp Asp Val Gly Ala Val Ser Gly Gly Gly Leu
25                  30                  35                  40 ctg gag cgg tgc ccg tcg ggg tgg aac ctc gag agg ttt ctg gag gag         378
Leu Glu Arg Cys Pro Ser Gly Trp Asn Leu Glu Arg Phe Leu Glu Glu
                 45                  50                  55 ctc gac ggc gtc cct gca ccg gcg gcg agc ccg gac ggc gcg gcg att         426
Leu Asp Gly Val Pro Ala Pro Ala Ala Ser Pro Asp Gly Ala Ala Ile
             60                  65                  70 tac cct agc ccg atg ccg gcg gcg gcg gcg gag gcg gcg gcg cgc tgg         474
Tyr Pro Ser Pro Met Pro Ala Ala Ala Ala Glu Ala Ala Ala Arg Trp
         75                  80                  85

```
agt agg ggc tac ggc gat cgt gag gcg gtg ggg gtg atg ccc atg ccc     522
Ser Arg Gly Tyr Gly Asp Arg Glu Ala Val Gly Val Met Pro Met Pro
    90                  95                 100 gcg gcc gcg ctt ccg gcg gcg ccg gcg agc gcg gcg atg gac ccc gtg     570
Ala Ala Ala Leu Pro Ala Ala Pro Ala Ser Ala Ala Met Asp Pro Val
105                 110                 115                 120 gag tac aac gcg atg ctg aag cgg aag ctg gac gag gac ctc gcc acc     618
Glu Tyr Asn Ala Met Leu Lys Arg Lys Leu Asp Glu Asp Leu Ala Thr
                125                 130                 135 gtc gcc atg tgg agg gcc tct ggt gca ata cat tct gag agt cct cta     666
Val Ala Met Trp Arg Ala Ser Gly Ala Ile His Ser Glu Ser Pro Leu
            140                 145                 150 ggc aat aaa aca tca ctg agt ata gtt ggt tcc atc ctg agt tca cag     714
Gly Asn Lys Thr Ser Leu Ser Ile Val Gly Ser Ile Leu Ser Ser Gln
        155                 160                 165 aag tgc att gaa ggt aac ggg ata cta gtg cag acc aag tta agt cct     762
Lys Cys Ile Glu Gly Asn Gly Ile Leu Val Gln Thr Lys Leu Ser Pro
    170                 175                 180 ggc cca aat gga gga tca ggc cca tat gta aat caa aat aca gat gct     810
Gly Pro Asn Gly Gly Ser Gly Pro Tyr Val Asn Gln Asn Thr Asp Ala
185                 190                 195                 200 cat gcc aag caa gct acg agt ggt tcc tca agg gag cca tca cca tca     858
His Ala Lys Gln Ala Thr Ser Gly Ser Ser Arg Glu Pro Ser Pro Ser
                205                 210                 215 gag gat gat gat atg gaa gga gat gca gag gca atg gga aat atg atc     906
Glu Asp Asp Asp Met Glu Gly Asp Ala Glu Ala Met Gly Asn Met Ile
            220                 225                 230 ctt gat gaa gaa gat aaa gtg aag aaa agg aag gaa tcc aac cgg gag     954
Leu Asp Glu Glu Asp Lys Val Lys Lys Arg Lys Glu Ser Asn Arg Glu
        235                 240                 245 tca gct aga cgc tca aga agc aga aag gca gct cgc cta aaa gac ctg    1002
Ser Ala Arg Arg Ser Arg Ser Arg Lys Ala Ala Arg Leu Lys Asp Leu
    250                 255                 260 gag gag cag gta tca cta tta agg gtt gaa aac tct tct ctg ttg agg    1050
Glu Glu Gln Val Ser Leu Leu Arg Val Glu Asn Ser Ser Leu Leu Arg
265                 270                 275                 280 cgt ctt gct gat gca aat cag aag tac agt gct gct gct att gac aat    1098
Arg Leu Ala Asp Ala Asn Gln Lys Tyr Ser Ala Ala Ala Ile Asp Asn
                285                 290                 295 agg gta cta atg gca gac att gaa gcc cta aga gca aag gtg agg atg    1146
Arg Val Leu Met Ala Asp Ile Glu Ala Leu Arg Ala Lys Val Arg Met
            300                 305                 310
```

```
gca gag gag agt gtg aag atg gtt aca ggg gct aga caa ctt cac cag    1194
Ala Glu Glu Ser Val Lys Met Val Thr Gly Ala Arg Gln Leu His Gln
        315                 320                 325 gcc att cct gac atg caa tct ccc ctc aat gtc aac tct gat gct tct    1242
Ala Ile Pro Asp Met Gln Ser Pro Leu Asn Val Asn Ser Asp Ala Ser
    330                 335                 340 gtg ccg atc cag aac aac aac cca atg aac tac ttc tcc aac gct aac    1290
Val Pro Ile Gln Asn Asn Asn Pro Met Asn Tyr Phe Ser Asn Ala Asn
345                 350                 355                 360 aat gcc ggt gtt aac agc ttc atg cac cag gtt tct cca gcg ttc cag    1338
Asn Ala Gly Val Asn Ser Phe Met His Gln Val Ser Pro Ala Phe Gln
            365                 370                 375 att gtg gat tct gtc gag aag att gac cca aca gat cca gtg cag ctg    1386
Ile Val Asp Ser Val Glu Lys Ile Asp Pro Thr Asp Pro Val Gln Leu
        380                 385                 390 cag cag caa cag atg gcg agc ttg cag cat ctt cag aat aga gct tgt    1434
Gln Gln Gln Gln Met Ala Ser Leu Gln His Leu Gln Asn Arg Ala Cys
    395                 400                 405 ggt ggc ggc gca agt tcg aat gaa tat aca gca tgg gga tcg tct ctg    1482
Gly Gly Gly Ala Ser Ser Asn Glu Tyr Thr Ala Trp Gly Ser Ser Leu
410                 415                 420 atg gat gca aat gag ctt gtc aac atg gag ctt cag tagtaggagc         1528
Met Asp Ala Asn Glu Leu Val Asn Met Glu Leu Gln
425                 430                 435 atatcctaac aacatgatga gagcatttgg aggtgcaaat ttgcaacctg caaatgctgt   1588
tttgtagtag tagttgttgt cgctgttttt gtctgaaact gtagtttcta tggattttgg   1648
acttgctgag gaacatctgc ggctgttgtt gtttcaaatt gagaaaatga gggacaatgg   1708
gacatggtgg tctcccttaa tatagcgaaa aaatggttgg ata                    1751

<210>  2
<211>  436
<212>  PRT
<213>  Oryza sativa

<400>  2

Met Glu His Val Phe Ala Val Asp Glu Ile Pro Asp Pro Leu Trp Ala
1               5                   10                  15

Pro Pro Pro Pro Val Gln Pro Ala Ala Ala Gly Val Asp Asp Val
            20                  25                  30
```

```
Gly Ala Val Ser Gly Gly Gly Leu Leu Glu Arg Cys Pro Ser Gly Trp
            35                  40                  45

Asn Leu Glu Arg Phe Leu Glu Glu Leu Asp Gly Val Pro Ala Pro Ala
        50                  55                  60

Ala Ser Pro Asp Gly Ala Ala Ile Tyr Pro Ser Pro Met Pro Ala Ala
 65                  70                  75                  80

Ala Ala Glu Ala Ala Ala Arg Trp Ser Arg Gly Tyr Gly Asp Arg Glu
                85                  90                  95

Ala Val Gly Val Met Pro Met Pro Ala Ala Leu Pro Ala Ala Pro
                100                 105                 110

Ala Ser Ala Ala Met Asp Pro Val Glu Tyr Asn Ala Met Leu Lys Arg
            115                 120                 125

Lys Leu Asp Glu Asp Leu Ala Thr Val Ala Met Trp Arg Ala Ser Gly
        130                 135                 140

Ala Ile His Ser Glu Ser Pro Leu Gly Asn Lys Thr Ser Leu Ser Ile
145                 150                 155                 160

Val Gly Ser Ile Leu Ser Ser Gln Lys Cys Ile Glu Gly Asn Gly Ile
                165                 170                 175

Leu Val Gln Thr Lys Leu Ser Pro Gly Pro Asn Gly Gly Ser Gly Pro
                180                 185                 190

Tyr Val Asn Gln Asn Thr Asp Ala His Ala Lys Gln Ala Thr Ser Gly
            195                 200                 205

Ser Ser Arg Glu Pro Ser Pro Ser Glu Asp Asp Met Glu Gly Asp
        210                 215                 220

Ala Glu Ala Met Gly Asn Met Ile Leu Asp Glu Glu Asp Lys Val Lys
225                 230                 235                 240

Lys Arg Lys Glu Ser Asn Arg Glu Ser Ala Arg Arg Ser Arg Ser Arg
                245                 250                 255

Lys Ala Ala Arg Leu Lys Asp Leu Glu Glu Gln Val Ser Leu Leu Arg
            260                 265                 270
```

```
Val Glu Asn Ser Ser Leu Leu Arg Arg Leu Ala Asp Ala Asn Gln Lys
        275                 280                 285

Tyr Ser Ala Ala Ala Ile Asp Asn Arg Val Leu Met Ala Asp Ile Glu
        290                 295                 300

Ala Leu Arg Ala Lys Val Arg Met Ala Glu Ser Val Lys Met Val
305                 310                 315                 320

Thr Gly Ala Arg Gln Leu His Gln Ala Ile Pro Asp Met Gln Ser Pro
                325                 330                 335

Leu Asn Val Asn Ser Asp Ala Ser Val Pro Ile Gln Asn Asn Asn Pro
            340                 345                 350

Met Asn Tyr Phe Ser Asn Ala Asn Asn Ala Gly Val Asn Ser Phe Met
                355                 360                 365

His Gln Val Ser Pro Ala Phe Gln Ile Val Asp Ser Val Glu Lys Ile
        370                 375                 380

Asp Pro Thr Asp Pro Val Gln Leu Gln Gln Gln Met Ala Ser Leu
385                 390                 395                 400

Gln His Leu Gln Asn Arg Ala Cys Gly Gly Gly Ala Ser Ser Asn Glu
                405                 410                 415

Tyr Thr Ala Trp Gly Ser Ser Leu Met Asp Ala Asn Glu Leu Val Asn
                420                 425                 430

Met Glu Leu Gln
        435

<210>  3
<211>  6335
<212>  DNA
<213>  Oryza sativa

<400>  3
tgctccattg cgctctcgga cgagcatata tgtatgacat gtgggcccgg aatgtcagta      60
acagggaatc ctgaaaaaaa tgcagctatg tgataatttt caacgctaat gttgcagttt     120
tctgaaaagt gtcgcaaagg ttgcagcaaa gtgatagttt agtcaataaa actgcagttt     180
tctgaaattt actctagttt ttttacctat ctagttggtt ttatgtgtaa ctaaacctta     240
```

```
catcagatca aaacaagttt ataaattcac cacgtatttc cctcagctca catctttctg     300
agaacatgat aaattcatta cattgtgcta caccatatgg ggactttaga acatgttcgt     360
cttcttttt  tttctttttt cttttttaca ttttaccttc tcagtttaca aatacttgtt     420
agctttgcct ggatatgtaa cccaacacta tgatacaaat tttgtcaatt ctctaaaatt     480
tttcaagttt gaaacaaatt aagatgtatg gttgtgggtg aattaatcta cattgatagg     540
aaatgcgtta aagtacatgc aaagcttatg aaattattgc aagtagtcat catgcctcag     600
tgagtcagtg tgcatacttg tagtgcataa ccaaattctt tttcatatac tagaaagatt     660
caaagctgca aatgtgcatg tgaggttgat gaatggaata cacaataata catgacaata     720
aacacatatt aaagaattta gtgcaaaaaa attgtattgt catggtacac attttaacaa     780
ttttctttac tttttataca ttgtaaatat taattaatat ctaaaacaaa atataaagta     840
cgggaataaa atttaattgg ctaatgtgga aatggcatgg agctaaatgt tctatatatg     900
gtcctaacgt ttaaagataa aatacatatg tgcttgtgtt actaataata tctaaaagac     960
taagtagtat gtattaaata tgctagagaa cataagaaac ttaaaaactt gacgtggcaa    1020
aatgggcgct taagcgacac atattgcact ttcagctgat cttattcccc cttttaaatt    1080
tcatgtcccc attttgatta tcacatggaa tcaaccacat tatacctatg catccttgtg    1140
atttctgaaa ttaaactcga aagcaaccaa gtaaagagga gggggagaaa aagttagcag    1200
aaaacatgga tgatacatgt caataagctg ctagcataac cataagtgta gggcacgttt    1260
cttaggacaa tggtataaag ttacaaactg aaatatcatt gttaggtcag tttgatataa    1320
tcagtttgga ttactataga cacttgtcat agtaaataga gatggatcat ttcttaagta    1380
gcatcactac tcttattcac gaatgtcttt gctaccctt  ctgttatact ttcctcttt    1440
ttctgtagaa agccatttgt ccttatatta tcattgtcaa attaaggatg cgtaatctac    1500
accctcactc aaaaactttg ataagataaa aacaaataaa tccatgcctt tatagaacct    1560
tgtcaaaatt atgctacacc tgtgctagga acaccatacc atcgtagctt acttgcacgc    1620
tttctgttag ccctttttcc taataaaaac gtattcgtcc gtatcgttgt tatcgctttg    1680
atcgtgtggg tttcactta  tatccgttga aacctctgtt aacacgtcca aattatttat    1740
atcggtatta tcactcaaga tcgtgcgggt tgttttgctt tttacgtttc ttgaagcttc    1800
taaagagggg acaaacctat ataaatagga gaggagagca ccctctcaac tcagttcaaa    1860
attgaaaaaa aaagaaaaa  aaaagagaag aaaaaaaaac ccatgggttg cgtagccgta    1920
gctttcccac catttccttc tctccgaagc ctcctcctct ccgcttcctc ccgcgaaacc    1980
```

```
aaattccaaa gcatttgatc gaatttctcc caaactttc cagcgttttc aatttcgccc    2040
cgatttcggt tcgaaaaccc ctcgcgaatt catttcaaac tcgtccgaga gcgcaatgga    2100
gcacgtgttc gccgtcgacg agatccccga cccgctgtgg gctccgccgc cgccggtgca    2160
gccggcggcg gccgccggag tagatgacgt cggcgcggtg agcggcggcg ggttgctgga    2220
gcggtgcccg tcggggtgga acctcgagag gtttctggag gagctcgacg gcgtccctgc    2280
accggcggcg agcccggacg gcgcggcgat ttaccctagc ccgatgccgg cggcggcggc    2340
ggaggcggcg gcgcgctgga gtaggggcta cggcgatcgt gaggcggtgg gggtgatgcc    2400
catgcccgcg gccgcgcttc cggcggcgcc ggcgagcgcg gcgatggacc ccgtggagta    2460
caacgcgatg ctgaagcgga agctggacga ggacctcgcc accgtcgcca tgtggagggt    2520
actctctctc atctcgatcg ctgcttgctt tgcttgcttc atggcttgta cagttgtact    2580
ggtgggttca ccatttgggg tggtggtgat gggatggctg tggcgtaatt aagtgcaatt    2640
tttagggcat ttcctgtgat taactgtggc tagatggtcg caatttagca tagatgtgac    2700
atatcctagc tgttactatg aatctggacc ggctctctgt ccagattcat agtactagat    2760
gtgtcacatc cctctaaatc tcttatatta taaggaggga gtataaatta attttataag    2820
agcacgcgtt gatgtcgata tccgcatcgt aagcccaggc actactcacg tgtgtgcttt    2880
cttatccata ctttaatatt gtcagagtgg gatgagacaa actttaatat tgtcggggtg    2940
tggtataata tttatattat ttccgtgtat agatttagga gtaatatgga ttaggattgc    3000
atggaggtgc agagacttta tgtgacttct tggagccgtg cattgcttga gtgcaaagtt    3060
aacaatttgg ttacatgttg caaaaatgat gtatagatca taggtcattg cacttatttt    3120
gggtggtcct aggcggtatg attcatggaa tattttttgg aaattctgta ttttaccata    3180
tttgcattac ttttcttatt attgttgttt gaaggaatta ttaggtcaca taccctttgga   3240
agatgaaatt attttagtag aaaaaaagaa actgttatat tggaatctgg taaatttgga    3300
cctagaaatt ctcaccagtc gattgtagat ggggaagcag agctttcttt ttagagattt    3360
gctccgctcc aacaaaaagt acctcgaggt actggtacct catggtacca aatcgtttcc    3420
gatcgttgga tctaacaatg cacatcctgc ctaattagat ccaacgatcg aaaatgattt    3480
ggtaccgtga ggtaccggta cctcgaggta cttttgttg gaccggagaa aatatcttct     3540
tttatgtta gttttctaag tggggtatat aattttgca attggatatc atactttgaa     3600
ctcattatgt gggttcagtt tacaaatgac tacagaacat gttgatctga gcttttgcta    3660
gttgatttca gtttacaatg tgaaacggtt ccctatataa gattataatg ccattagaac    3720
```

```
taattaacta tgagagtgtg tgtttagctc cgatagttat taagtccctt tgcattctga      3780
cttcaatttt tggcatgtcc atccatccac aggcctctgg tgcaatacat tctgagagtc      3840
ctctaggcaa taaaacatca ctgagtatag ttggttccat cctgagttca cagaagtgca      3900
ttgaaggtat tctattatgc atatgtgctt agttaaatct tctcagtacc tatgagttat      3960
gacttatgag taatctctaa tgttgtaagc aaatctaatt tttgcgtaat gtagttttca      4020
tattatatat atctgattgg attttccccc tatttcgaca cattcaggta acgggatact      4080
agtgcagacc aagttaagtc ctggcccaaa tggaggatca ggcccatatg taaatcaaaa      4140
tacagatgct catgccaagc aagctacgag tggttcctca agggagccat caccatcaga      4200
ggatgatgat atggaaggag atgcagaggc aatgggaaat atgatccttg atgaagaaga      4260
taaagtgaag aaaaggtaat atgtattctt ttgcttgtgt atttttattt ttcaattcaa      4320
cacatacaaa gagtaaacac tgagcattag cattagaaat tagggacttt tacatctat       4380
tgatttcctt ttttcttaga aatagctttt aagtaatatg ctttagatta tcaagataat      4440
ggatccttag tttctttcta ggtgtttcat gtttgtactg gatgtatttg attatataca      4500
acattctcac ttttttctta gaaatgcttg agctaatgct tgctaggtgt ttcaatgctt      4560
tatatacctg actgaatttt ggtaatgctt gttacaagct ggtgcattaa ggataattat      4620
tgtttccgtg caagcagcta ttcatgcaaa aaaggaaaaa tgcaacgtgt atgattagaa      4680
caatttagga ggcatttgct tcttgctttt cataacatgc tgggaatatc atgtcctgtt      4740
gtgtctagtt gcttttttcta catatgaaaa attgagttta tctactgtgg tcttttttttc    4800
cgcagcagtc agacattcat gtcgcctttt tttgtgtaat aaatacagcc ggatatttga      4860
gatttgagct tgtgttcttg tccaatttca ggaaggaatc caaccgggag tcagctagac      4920
gctcaagaag cagaaaggca gctcgcctaa aagacctgga ggagcaggtt ttgtgtttta      4980
cactattcca tttgactgca caacaaagtt ttggaatatg taagtaacaa gtgtaattgt      5040
tgctaaatca ttgcaggtat cactattaag ggttgaaaac tcttctctgt tgaggcgtct      5100
tgctgatgca aatcagaagt acagtgctgc tgctattgac aatagggtac taatggcaga      5160
cattgaagcc ctaagagcaa aggtatgcaa ctgtttaagt gccttttagt cctctgtatg      5220
aactgaacct ctctttcaaa taggtatcca attatccatg tgcattgatt ctggtcagta      5280
ttgtgcatct ttcatggtgt agaaaaccgg aatattctac atatcaaaca tataccaaat      5340
tttcttggaa tgaaacgaac ttctagcatt tgttcttaaa atttggtaca ggagatattg      5400
caaatgttgt cctcttgctc cattcgaagg attaagttgt ttgccatcta ttataacctg      5460
```

```
caacaattag actcacttgt tttgtcttga acaaccggg tgtaactact tttctttttc    5520
ctgcaacgta ccaggtgtaa ataatcgctt gccgaatggt gataaccaat tcacacaatg    5580
gatcacaatc aattttaaca aagaacctga gctacactac actactgcgg tgtcgtatct    5640
tatagccata tgcttctaga ccacaactga aaattcatga accatgcgat gtgggttagc    5700
taacatcttg acatgattgc aggtgaggat ggcagaggag agtgtgaaga tggttacagg    5760
ggctagacaa cttcaccagg ccattcctga catgcaatct cccctcaatg tcaactctga    5820
tgcttctgtg ccgatccaga acaacaaccc aatgaactac ttctccaacg ctaacaatgc    5880
cggtgttaac agcttcatgc accaggtttc tccagcgttc cagattgtgg attctgtcga    5940
gaagattgac ccaacagatc cagtgcagct gcagcagcaa cagatggcga gcttgcagca    6000
tcttcagaat agagcttgtg gtggcggcgc aagttcgaat gaatatacag catggggatc    6060
gtctctgatg gatgcaaatg agcttgtcaa catggagctt cagtagtagg agcatatcct    6120
aacaacatga tgagagcatt tggaggtgca aatttgcaac ctgcaaatgc tgttttgtag    6180
tagtagttgt tgtcgctgtt tttgtctgaa actgtagttt ctatggattt tggacttgct    6240
gaggaacatc tgcggctgtt gttgtttcaa attgagaaaa tgagggacaa tgggacatgg    6300
tggtctccct taatatagcg aaaaatggtt ggaat                                 6335

<210>   4
<211>   1199
<212>   DNA
<213>   Oryza sativa

<220>
<221>   CDS
<222>   (171)..(1004)

<400>   4
ggcacgaggc gatcaacaca aaagcttct ctttcccttc tcctcctcgg tgatctgtct         60
cgccggggca tctcgaaaag catccgactc cgacgccgcc gcgcgccacc acccggccga      120
tcgccgacgc cgcagccgct ggaagcagca gggacgacgg agaatcggag atg gac         176
                                                        Met Asp
                                                        1 atc gag gcg ttc atc cac ggc gga agc ggg ggc ggc gac gcc gac gcc        224
Ile Glu Ala Phe Ile His Gly Gly Ser Gly Gly Gly Asp Ala Asp Ala
        5                   10                  15 gac cac ccg ctc ggc atc ttc tcc gcc gcc gac ctc tcc ggc ttc ggc        272
Asp His Pro Leu Gly Ile Phe Ser Ala Ala Asp Leu Ser Gly Phe Gly
    20                  25                  30
```

```
ttc gcg gac tcg agc acc atc aca ggg ggc att ccc aat cac ata tgg       320
Phe Ala Asp Ser Ser Thr Ile Thr Gly Gly Ile Pro Asn His Ile Trp
 35              40                  45                  50 ccc cag tcc cag aac ctg aac gca cgg cat cct gcg gtc tcc acg aca       368
Pro Gln Ser Gln Asn Leu Asn Ala Arg His Pro Ala Val Ser Thr Thr
                 55                  60                  65 att gag tcg cag tca tca atc tgt gca gca gca agt ccc aca tca gct       416
Ile Glu Ser Gln Ser Ser Ile Cys Ala Ala Ala Ser Pro Thr Ser Ala
                 70                  75                  80 acc aat ctg aac atg aag gag agc caa act ctg gga ggc aca agt ggt       464
Thr Asn Leu Asn Met Lys Glu Ser Gln Thr Leu Gly Gly Thr Ser Gly
     85                  90                  95 tcg gat tct gaa agt gaa tcg ctg ttg gat ata gag ggt ggt cca tgc       512
Ser Asp Ser Glu Ser Glu Ser Leu Leu Asp Ile Glu Gly Gly Pro Cys
    100                 105                 110 gaa caa agc acg aac ccg ttg gac gtg aag aga gtg aga agg atg gtg       560
Glu Gln Ser Thr Asn Pro Leu Asp Val Lys Arg Val Arg Arg Met Val
115                 120                 125                 130 tcc aat cgg gag tct gct cgg cga tcg agg aag aga aag caa gct cac       608
Ser Asn Arg Glu Ser Ala Arg Arg Ser Arg Lys Arg Lys Gln Ala His
                135                 140                 145 tta gct gat ctc gag tca cag gtt gac cag ctc cgg ggc gaa aac gca       656
Leu Ala Asp Leu Glu Ser Gln Val Asp Gln Leu Arg Gly Glu Asn Ala
                150                 155                 160 tcg ctt ttc aag cag ttg acg gat gcc aac cag caa ttc aca act tct       704
Ser Leu Phe Lys Gln Leu Thr Asp Ala Asn Gln Gln Phe Thr Thr Ser
    165                 170                 175 gtc acg gac aac aga atc ctc aaa tca gac gtt gag gcc ctc cgg gtc       752
Val Thr Asp Asn Arg Ile Leu Lys Ser Asp Val Glu Ala Leu Arg Val
    180                 185                 190 aag gtg aag atg gcg gag gac atg gtg gcg cgg ggg gcg ctg tcg tgc       800
Lys Val Lys Met Ala Glu Asp Met Val Ala Arg Gly Ala Leu Ser Cys
195                 200                 205                 210 ggg ctc ggc cac ctg ggc ggg ctg tcg ccg gcg ctg aac ccc cgg cag       848
Gly Leu Gly His Leu Gly Gly Leu Ser Pro Ala Leu Asn Pro Arg Gln
                215                 220                 225 gcg tgc cgc gtc ccc gac gtg ctc gcc ggc ctg gac tac gcc ggc gac       896
Ala Cys Arg Val Pro Asp Val Leu Ala Gly Leu Asp Tyr Ala Gly Asp
                230                 235                 240 gac ccc ttc acg gcc ggg ctg tcc cag ccg gag cag ttg cag atg ccc       944
Asp Pro Phe Thr Ala Gly Leu Ser Gln Pro Glu Gln Leu Gln Met Pro
    245                 250                 255
```

```
ggc ggc gag gtg gtt gac gcc tgg ggc tgg gac aac cac ccc aac ggc    992
Gly Gly Glu Val Val Asp Ala Trp Gly Trp Asp Asn His Pro Asn Gly
    260                 265                 270 ggc atg tcc aag tgaaactact ggtcctactt ctatgtcagc tcagctacgt        1044
Gly Met Ser Lys
275 ttgaaacgtg atgtgtccaa gtgaacggac ttgagttttt cagagtcctc gtgtcgaagt  1104 gtcatgcact cttccctatt cctgtaatag aactgactag ctaagagact gaaagtctga  1164 aactacgaag tataaatgtg gtggaatttg gaact                             1199

<210>  5
<211>  278
<212>  PRT
<213>  Oryza sativa

<400>  5

Met Asp Ile Glu Ala Phe Ile His Gly Gly Ser Gly Gly Gly Asp Ala
1               5                   10                  15

Asp Ala Asp His Pro Leu Gly Ile Phe Ser Ala Ala Asp Leu Ser Gly
            20                  25                  30

Phe Gly Phe Ala Asp Ser Ser Thr Ile Thr Gly Gly Ile Pro Asn His
        35                  40                  45

Ile Trp Pro Gln Ser Gln Asn Leu Asn Ala Arg His Pro Ala Val Ser
    50                  55                  60

Thr Thr Ile Glu Ser Gln Ser Ser Ile Cys Ala Ala Ser Pro Thr
65                  70                  75                  80

Ser Ala Thr Asn Leu Asn Met Lys Glu Ser Gln Thr Leu Gly Gly Thr
                85                  90                  95

Ser Gly Ser Asp Ser Glu Ser Glu Ser Leu Leu Asp Ile Glu Gly Gly
            100                 105                 110

Pro Cys Glu Gln Ser Thr Asn Pro Leu Asp Val Lys Arg Val Arg Arg
        115                 120                 125

Met Val Ser Asn Arg Glu Ser Ala Arg Arg Ser Lys Arg Lys Gln
    130                 135                 140
```

```
     Ala His Leu Ala Asp Leu Glu Ser Gln Val Asp Gln Leu Arg Gly Glu
     145                 150                 155                 160

Asn Ala Ser Leu Phe Lys Gln Leu Thr Ala Asn Gln Gln Phe Thr
                     165                 170                 175

Thr Ser Val Thr Asp Asn Arg Ile Leu Lys Ser Asp Val Glu Ala Leu
                     180                 185                 190

Arg Val Lys Val Lys Met Ala Glu Asp Met Val Ala Arg Gly Ala Leu
                     195                 200                 205

Ser Cys Gly Leu Gly His Leu Gly Gly Leu Ser Pro Ala Leu Asn Pro
     210                 215                 220

Arg Gln Ala Cys Arg Val Pro Asp Val Leu Ala Gly Leu Asp Tyr Ala
     225                 230                 235                 240

Gly Asp Asp Pro Phe Thr Ala Gly Leu Ser Gln Pro Glu Gln Leu Gln
                     245                 250                 255

Met Pro Gly Gly Glu Val Val Asp Ala Trp Gly Trp Asp Asn His Pro
                     260                 265                 270

Asn Gly Gly Met Ser Lys
                     275

<210>  6
<211>  1362
<212>  DNA
<213>  Oryza sativa

<220>
<221>  CDS
<222>  (23)..(907)

<400>  6
ggcacgaggt cggaggaagg cg atg atg aag aag tgc ccg tcg gag ctg cag     52
                         Met Met Lys Lys Cys Pro Ser Glu Leu Gln
                          1               5                  10 ctg gag gcg ttc atc cgg gag gag gcc ggc gcc ggc gac cgc aag ccc    100
Leu Glu Ala Phe Ile Arg Glu Glu Ala Gly Ala Gly Asp Arg Lys Pro
            15                  20                  25 ggc gtg tta tct ccc ggc gac ggc gcg cgt aag tcc ggc ctg ttc tct    148
Gly Val Leu Ser Pro Gly Asp Gly Ala Arg Lys Ser Gly Leu Phe Ser
        30                  35                  40
```

```
ccc ggc gac ggc gag atg tcc gtg ttg gat cag agt aca ctg gac gga    196
Pro Gly Asp Gly Glu Met Ser Val Leu Asp Gln Ser Thr Leu Asp Gly
         45                  50                  55 agc ggc ggc ggc cac cag ctg tgg tgg ccg gag agc gtc cgt acg ccg    244
Ser Gly Gly Gly His Gln Leu Trp Trp Pro Glu Ser Val Arg Thr Pro
    60                  65                  70 ccg cgc gcc gcc gcc gcc ttc tcg gcc acg gcc gac gag cgg acg ccg    292
Pro Arg Ala Ala Ala Ala Phe Ser Ala Thr Ala Asp Glu Arg Thr Pro
75                  80                  85                  90 gcg tcc atc tcc gat gac ccc aaa cca acc acc tca gcg aac cac gcg    340
Ala Ser Ile Ser Asp Asp Pro Lys Pro Thr Thr Ser Ala Asn His Ala
                 95                 100                 105 cct gaa agc gac tcg gac tcc gat tgc gat tcg ctg tta gaa gca gag    388
Pro Glu Ser Asp Ser Asp Ser Asp Cys Asp Ser Leu Leu Glu Ala Glu
            110                 115                 120 agg agt cca cgc ctg cgt ggc acg aaa tcc aca gaa aca aag cga ata    436
Arg Ser Pro Arg Leu Arg Gly Thr Lys Ser Thr Glu Thr Lys Arg Ile
        125                 130                 135 aga agg atg gtg tcc aac agg gag tcc gct cga cga tcc agg agg aga    484
Arg Arg Met Val Ser Asn Arg Glu Ser Ala Arg Arg Ser Arg Arg Arg
    140                 145                 150 aag cag gca cag tta tct gaa ctc gaa tca cag gtc gag caa ctc aaa    532
Lys Gln Ala Gln Leu Ser Glu Leu Glu Ser Gln Val Glu Gln Leu Lys
155                 160                 165                 170 ggc gaa aac tca tcc ctc ttc aag cag ctc aca gag tcc agc cag cag    580
Gly Glu Asn Ser Ser Leu Phe Lys Gln Leu Thr Glu Ser Ser Gln Gln
                175                 180                 185 ttc aat aca gcg gtc acg gac aac agg atc ctc aaa tcg gat gta gag    628
Phe Asn Thr Ala Val Thr Asp Asn Arg Ile Leu Lys Ser Asp Val Glu
            190                 195                 200 gcc tta aga gtc aag gtc aag atg gct gaa gac atg gtc gcg agg gcc    676
Ala Leu Arg Val Lys Val Lys Met Ala Glu Asp Met Val Ala Arg Ala
        205                 210                 215 gcg atg tcg tgt ggc ctg ggc cag ctc ggg ctg gcg cca ttg ctc agc    724
Ala Met Ser Cys Gly Leu Gly Gln Leu Gly Leu Ala Pro Leu Leu Ser
    220                 225                 230 tcc agg aag atg tgc caa gct ttg gat atg ctc agt tta cca cgg aac    772
Ser Arg Lys Met Cys Gln Ala Leu Asp Met Leu Ser Leu Pro Arg Asn
235                 240                 245                 250 gat gcc tgt ggt ttc aaa ggc ttg aac ctg ggt cga cag gtt cag aac    820
Asp Ala Cys Gly Phe Lys Gly Leu Asn Leu Gly Arg Gln Val Gln Asn
                255                 260                 265
```

```
tca ccg gtt caa agc gct gca agc cta gag agc ctg gac aac cgg ata    868
Ser Pro Val Gln Ser Ala Ala Ser Leu Glu Ser Leu Asp Asn Arg Ile
        270                 275                 280 tcc agc gag gtg acc agc tgc tcg gct gat gtg tgg cct taagacactt    917
Ser Ser Glu Val Thr Ser Cys Ser Ala Asp Val Trp Pro
        285                 290                 295 catccgtgtt cgagagagct tgagattcta agaagcagcc ggtgagaatc tgaaaaggct    977
agttgttcag tttcctattt ttagtttatg tttgaattct ctggctacta atgctcaaaa    1037
tctgggagag aatctaaatc gtttgggaca gataaaaaat tatgcgagaa ggtgtagctg    1097
acagaaacct tcccaaacaa atctccatca gaacctatat gtaaagtaat acggtatcct    1157
ctgttactag gtgcatgtgc ataactgaca agctgctaag tactaggtac tacagtctga    1217
ggcaagtatt tctggtgttt tggtgctgaa gaactatgtt ttagtgcgtt tgatctgcgg    1277
caatcaaggc catctgatcg aaatttgatt ggtataaatc tgatcgaaat ttgattggta    1337
taagtataat agtttgatti tgatc                                         1362
```

<210> 7
<211> 295
<212> PRT
<213> Oryza sativa

<400> 7

Met Met Lys Lys Cys Pro Ser Glu Leu Gln Leu Glu Ala Phe Ile Arg
1               5                   10                  15

Glu Glu Ala Gly Ala Gly Asp Arg Lys Pro Gly Val Leu Ser Pro Gly
            20                  25                  30

Asp Gly Ala Arg Lys Ser Gly Leu Phe Ser Pro Gly Asp Gly Glu Met
        35                  40                  45

Ser Val Leu Asp Gln Ser Thr Leu Asp Gly Ser Gly Gly His Gln
    50                  55                  60

Leu Trp Trp Pro Glu Ser Val Arg Thr Pro Pro Arg Ala Ala Ala Ala
65                  70                  75                  80

```
Phe Ser Ala Thr Ala Asp Glu Arg Thr Pro Ala Ser Ile Ser Asp Asp
                85                  90                  95

Pro Lys Pro Thr Thr Ser Ala Asn His Ala Pro Glu Ser Asp Ser Asp
            100                 105                 110

Ser Asp Cys Asp Ser Leu Leu Glu Ala Glu Arg Ser Pro Arg Leu Arg
        115                 120                 125

Gly Thr Lys Ser Thr Glu Thr Lys Arg Ile Arg Arg Met Val Ser Asn
    130                 135                 140

Arg Glu Ser Ala Arg Arg Ser Arg Arg Arg Lys Gln Ala Gln Leu Ser
145                 150                 155                 160

Glu Leu Glu Ser Gln Val Glu Gln Leu Lys Gly Glu Asn Ser Ser Leu
                165                 170                 175

Phe Lys Gln Leu Thr Glu Ser Ser Gln Phe Asn Thr Ala Val Thr
            180                 185                 190

Asp Asn Arg Ile Leu Lys Ser Asp Val Glu Ala Leu Arg Val Lys Val
        195                 200                 205

Lys Met Ala Glu Asp Met Val Ala Arg Ala Ala Met Ser Cys Gly Leu
    210                 215                 220

Gly Gln Leu Gly Leu Ala Pro Leu Leu Ser Ser Arg Lys Met Cys Gln
225                 230                 235                 240

Ala Leu Asp Met Leu Ser Leu Pro Arg Asn Asp Ala Cys Gly Phe Lys
                245                 250                 255

Gly Leu Asn Leu Gly Arg Gln Val Gln Asn Ser Pro Val Gln Ser Ala
            260                 265                 270

Ala Ser Leu Glu Ser Leu Asp Asn Arg Ile Ser Ser Glu Val Thr Ser
        275                 280                 285

Cys Ser Ala Asp Val Trp Pro
290                 295
```

```
<210>  8
<211>  12
<212>  DNA
<213>  Oryza sativa

<400>  8
gctgagtcat ga                                                          12

<210>  9
<211>  12
<212>  DNA
<213>  Oryza sativa

<400>  9
catgagtcac tt                                                          12

<210>  10
<211>  12
<212>  DNA
<213>  Oryza sativa

<400>  10
agtgagtcac tt                                                          12

<210>  11
<211>  12
<212>  DNA
<213>  Oryza sativa

<400>  11
ggtgagtcat at                                                          12

<210>  12
<211>  12
<212>  DNA
<213>  Oryza sativa

<400>  12
ggtgagtcat gt                                                          12

<210>  13
<211>  12
<212>  DNA
<213>  Oryza sativa

<400>  13
gatgagtcat gc                                                          12
```

```
<210>  14
<211>  12
<212>  DNA
<213>  Oryza sativa

<400>  14
aatgagtcat ca                                                        12

<210>  15
<211>  12
<212>  DNA
<213>  Oryza sativa

<400>  15
agccacgtca ca                                                        12

<210>  16
<211>  17
<212>  DNA
<213>  Artificial Sequence

<220>
<223>  Synthetic

<220>
<221>  modified_base
<222>  (9)..(9)
<223>  I

<220>
<221>  misc_feature
<222>  (9)..(9)
<223>  n is a, c, g, or t

<220>
<221>  modified_base
<222>  (15)..(15)
<223>  I

<220>
<221>  misc_feature
<222>  (15)..(15)
<223>  n is a, c, g, or t

<400>  16
tccaaymgng arwcngc                                                   17
```

```
<210>  17
<211>  21
<212>  DNA
<213>  Artificial Sequence

<220>
<223>  Synthetic

<400>  17
gtcctcygcc atcttcacct t                                              21

<210>  18
<211>  21
<212>  DNA
<213>  Artificial Sequence

<220>
<223>  Synthetic

<400>  18
atgggttgcg tagccgtagc t                                              21

<210>  19
<211>  21
<212>  DNA
<213>  Artificial Sequence

<220>
<223>  Synthetic

<400>  19
ttgcttggca tgagcatctg t                                              21

<210>  20
<211>  17
<212>  DNA
<213>  Artificial Sequence

<220>
<223>  Synthetic

<400>  20
gaggatcagg cccatat                                                   17
```

```
<210>  21
<211>  21
<212>  DNA
<213>  Artificial Sequence

<220>
<223>  Synthetic

<400>  21
tcgctatatt aagggagacc a                                              21

<210>  22
<211>  24
<212>  DNA
<213>  Artificial Sequence

<220>
<223>  Synthetic

<400>  22
tgctccattg cgctctcgga cgag                                           24

<210>  23
<211>  23
<212>  DNA
<213>  Artificial Sequence

<220>
<223>  Synthetic

<400>  23
atgaattcgc gagggttttt cga                                            23

<210>  24
<211>  25
<212>  DNA
<213>  Artificial Sequence

<220>
<223>  Synthetic

<400>  24
gtttgggaga aattcgatca aatgc                                          25
```

<210> 25
<211> 30
<212> DNA
<213> Artificial Sequence

<220>
<223> Synthetic

<400> 25
atggtatggt gttcctagca caggtgtagc                                30

<210> 26
<211> 18
<212> DNA
<213> Artificial Sequence

<220>
<223> Synthetic

<400> 26
aaaactgcag ttttctga                                             18

<210> 27
<211> 25
<212> DNA
<213> Artificial Sequence

<220>
<223> Synthetic

<400> 27
aatggatccg cgaggggttt tcgaa                                     25

<210> 28
<211> 12
<212> DNA
<213> Oryza sativa

<400> 28
gcttcctcat ga                                                   12

<210> 29
<211> 26
<212> DNA
<213> Artificial Sequence

<220>
<223> Synthetic

<400> 29
aaccatggtg ctggagcggt gcccgt                                    26

```
<210>  30
<211>  25
<212>  DNA
<213>  Artificial Sequence

<220>
<223>  Synthetic

<400>  30
aaccatggcg gcggaggcgg cggcg                                    25

<210>  31
<211>  23
<212>  DNA
<213>  Artificial Sequence

<220>
<223>  Synthetic

<400>  31
ccccatggag tacaacgcga tgc                                      23

<210>  32
<211>  25
<212>  DNA
<213>  Artificial Sequence

<220>
<223>  Synthetic

<400>  32
aaccatggtt ggttccatcc tgagt                                    25

<210>  33
<211>  25
<212>  DNA
<213>  Artificial Sequence

<220>
<223>  Synthetic

<400>  33
aaccatggct catgccaagc aagct                                    25

<210>  34
<211>  28
<212>  DNA
<213>  Artificial Sequence

<220>
<223>  Synthetic

<400>  34
aaccatggat gaagaagata aagtgaag                                 28
```

```
<210> 35
<211> 26
<212> DNA
<213> Artificial Sequence

<220>
<223> Synthetic

<400> 35
taggatccgc tcctactact gaagct                                              26

<210> 36
<211> 27
<212> DNA
<213> Artificial Sequence

<220>
<223> Synthetic

<400> 36
aaggatccaa tggagcacgt gttcgcc                                             27

<210> 37
<211> 26
<212> DNA
<213> Artificial Sequence

<220>
<223> Synthetic

<400> 37
aaggatccgg cggcggaggc ggcgcg                                              26

<210> 38
<211> 27
<212> DNA
<213> Artificial Sequence

<220>
<223> Synthetic

<400> 38
gccggatcca gttggttcca tcctgag                                             27
```

```
<210>  39
<211>  26
<212>  DNA
<213>  Artificial Sequence

<220>
<223>  Synthetic

<400>  39
aaggatcctg atgaagaaga taaagt                                      26

<210>  40
<211>  27
<212>  DNA
<213>  Artificial Sequence

<220>
<223>  Synthetic

<400>  40
aaggatccag gagtagatga cgtcggc                                     27

<210>  41
<211>  29
<212>  DNA
<213>  Artificial Sequence

<220>
<223>  Synthetic

<400>  41
aaggatccag acgagatccc cgacccgct                                   29

<210>  42
<211>  28
<212>  DNA
<213>  Artificial Sequence

<220>
<223>  Synthetic

<400>  42
tagagctcta cgccgccggc atcgggct                                    28
```

```
<210>  43
<211>  28
<212>  DNA
<213>  Artificial Sequence

<220>
<223>  Synthetic

<400>  43
tagagctcta aaggatcata tttcccat                                28

<210>  44
<211>  28
<212>  DNA
<213>  Artificial Sequence

<220>
<223>  Synthetic

<400>  44
tagagctcta ggcggccgcc gccggctg                                28

<210>  45
<211>  28
<212>  DNA
<213>  Artificial Sequence

<220>
<223>  Synthetic

<400>  45
tagagctcta cggcggcggc ggagccca                                28

<210>  46
<211>  25
<212>  DNA
<213>  Artificial Sequence

<220>
<223>  Synthetic

<400>  46
aaaccatgga gcacgtgttc gccgt                                   25
```

```
<210>  47
<211>  26
<212>  DNA
<213>  Artificial Sequence

<220>
<223>  Synthetic

<400>  47
taggatccgc tcctactact gaagct                                      26

<210>  48
<211>  26
<212>  DNA
<213>  Artificial Sequence

<220>
<223>  Synthetic

<400>  48
aaaccatgga gggagaagct gagacc                                      26

<210>  49
<211>  30
<212>  DNA
<213>  Artificial Sequence

<220>
<223>  Synthetic

<400>  49
aaaggatcct acatatcaga agcggcggga                                  30

<210>  50
<211>  26
<212>  DNA
<213>  Artificial Sequence

<220>
<223>  Synthetic

<400>  50
aaaccatgga tatagagggc ggtcca                                      26
```

```
<210>  51
<211>  30
<212>  DNA
<213>  Artificial Sequence

<220>
<223>  Synthetic

<400>  51
aaaggatcct acagcccgcc caggtggccg                                              30

<210>  52
<211>  21
<212>  DNA
<213>  Oryza sativa

<400>  52
gtttgtcatg gctgagtcat g                                                       21

<210>  53
<211>  425
<212>  PRT
<213>  Oryza sativa

<400>  53
```

Met Glu Arg Val Phe Ser Val Glu Glu Ile Ser Asp Pro Phe Trp Val
1               5                   10                  15

Pro Pro Pro Pro Pro Gln Ser Ala Ala Ala Gln Gln Gln Gly Gly
            20                  25                  30

Gly Gly Val Ala Ser Gly Gly Gly Gly Val Ala Gly Gly Gly Gly
        35                  40                  45

Gly Gly Asn Ala Met Asn Arg Cys Pro Ser Glu Trp Tyr Phe Gln Lys
    50                  55                  60

Phe Leu Glu Glu Ala Val Leu Asp Ser Pro Val Pro Asn Pro Ser Pro
65                  70                  75                  80

Arg Ala Glu Ala Gly Gly Ile Arg Gly Ala Gly Gly Val Val Pro Val
                85                  90                  95

Asp Val Lys Gln Pro Gln Leu Ser Ala Ala Ala Ala Ala Ala Thr
            100                 105                 110

```
Thr Ser Ala Val Val Asp Pro Val Glu Tyr Asn Ala Met Leu Lys Gln
    115             120             125

Lys Leu Glu Lys Asp Leu Ala Ala Val Ala Met Trp Arg Ala Ser Gly
    130             135             140

Thr Val Pro Pro Glu Arg Pro Gly Ala Gly Ser Ser Leu Leu Asn Ala
145             150             155             160

Asp Val Ser His Ile Gly Ala Pro Ile Ser Ile Gly Gly Asn Ala Thr
            165             170             175

Pro Val Gln Asn Met Leu Ser Gly Pro Ser Gly Gly Ser Gly Ser Gln
            180             185             190

Leu Val Gln Asn Val Asp Val Leu Val Lys Gln Ala Thr Ser Ser Ser
        195             200             205

Ser Arg Glu Gln Ser Asp Asp Asp Met Glu Gly Glu Ala Glu Thr
    210             215             220

Thr Gly Thr Ala Arg Pro Ala Asp Gln Arg Leu Gln Arg Arg Lys Gln
225             230             235             240

Ser Asn Arg Glu Ser Ala Arg Arg Ser Arg Ser Arg Lys Ala Ala His
            245             250             255

Leu Asn Glu Leu Glu Ala Gln Val Ser Gln Leu Arg Val Glu Asn Ser
        260             265             270

Ser Leu Leu Arg Arg Leu Ala Asp Val Asn Gln Lys Tyr Asn Asp Ala
        275             280             285

Ala Val Asp Asn Arg Val Leu Lys Ala Asp Val Glu Thr Leu Arg Ala
        290             295             300

Lys Val Lys Met Ala Glu Asp Ser Val Lys Arg Val Thr Gly Met Asn
305             310             315             320

Ala Leu Phe Pro Ala Ala Ser Asp Met Ser Ser Leu Ser Met Pro Phe
                325             330             335
```

```
Asn Ser Ser Pro Ser Glu Ala Thr Ser Asp Ala Ala Val Pro Ile Gln
            340                 345                 350

Asp Asp Pro Asn Asn Tyr Phe Ala Thr Asn Asn Asp Ile Gly Gly Asn
            355                 360                 365

Asn Asn Tyr Met Pro Asp Ile Pro Ser Ser Ala Gln Glu Asp Glu Asp
            370                 375                 380

Phe Val Asn Gly Ala Leu Ala Ala Gly Lys Ile Gly Arg Thr Ala Ser
385                 390                 395                 400

Leu Gln Arg Val Ala Ser Leu Glu His Leu Gln Lys Arg Met Cys Gly
                405                 410                 415

Gly Pro Ala Ser Ser Gly Ser Thr Ser
            420                 425

<210>  54
<211>  405
<212>  PRT
<213>  Zea mays

<400>  54

Met Glu Arg Val Phe Ser Val Glu Glu Ile Pro Asn Pro Tyr Trp Val
1               5                   10                  15

Pro Pro His Pro Gln Ser Ala Ala Gly Ala Val Ala Ala Pro Ala
                20                  25                  30

Gly Glu Ala Ala Gly Leu Met Asn Arg Cys Pro Ser Glu Trp Tyr Phe
            35                  40                  45

Gln Lys Phe Leu Glu Glu Ala Val Leu Asp Ser Pro Val Pro Val Ala
        50                  55                  60

Gly Val Ser Arg Gly Ser Val Gly Ala Gly Val Glu Ala Ala Glu Arg
65                  70                  75                  80

Lys Thr Pro Gly Thr Ala Ala Ala Ala Ala Ser Ser Ser Val Val
                85                  90                  95

Asp Pro Val Glu Tyr Asn Ala Ile Val Lys Gln Lys Leu Glu Lys Asp
                100                 105                 110
```

```
Leu Ala Ala Val Ala Leu Trp Arg Ala Ser Gly Ala Ala Pro Pro Asp
            115                 120                 125

Asn Ser Pro Ala Gly Ser Ser Leu Pro Ser Val Asp Val Pro His Ala
    130                 135                 140

Gly Pro Leu Lys Pro Met Gly Gly Thr Gly Ser Leu Val Gln Asn Lys
145                 150                 155                 160

Leu Ala Gly Ala Pro Gly Gly Gly Ser Ser Pro His Val Val Gln Asn
                165                 170                 175

Ala Asp Ile Pro Val Lys Gln Thr Thr Ser Ser Ser Ser Arg Glu Gln
            180                 185                 190

Ser Asp Asp Asp Asp Met Glu Gly Asp Ala Glu Thr Thr Gly Asn Gly
        195                 200                 205

Asn Pro Val Gln Gln Arg Leu Gln Arg Arg Lys Gln Ser Asn Arg Glu
    210                 215                 220

Ser Ala Arg Arg Ser Arg Ser Arg Lys Ala Ala His Leu Asn Glu Leu
225                 230                 235                 240

Glu Ala Gln Val Ala Gln Leu Arg Val Glu Asn Ser Ser Leu Leu Arg
                245                 250                 255

Arg Leu Ala Asp Val Asn Gln Lys Phe Asn Glu Ala Ala Val Asp Asn
            260                 265                 270

Arg Val Leu Lys Ala Asp Val Glu Thr Leu Arg Ala Lys Val Lys Met
        275                 280                 285

Ala Glu Asp Ser Val Lys Arg Val Thr Gly Met Asn Thr Leu Phe Pro
    290                 295                 300

Ala Val Ser Asp Met Ser Ser Leu Ser Met Pro Phe Asn Gly Ser Pro
305                 310                 315                 320

Ser Asp Ser Ala Ser Asp Ala Ala Val Pro Ile Gln Asp Asp Leu Asn
                325                 330                 335

Ser Tyr Phe Ala Asn Pro Ser Glu Ile Gly Gly Ser Asn Gly Tyr Met
            340                 345                 350
```

```
    Pro Asp Ile Ala Ser Ser Ala Gln Glu Asp Asp Phe Val Asn Gly
            355                 360                 365

Ala Gln Val Ala Gly Lys Met Gly Ser Thr Asp Ser Leu Gln Arg Val
        370                 375                 380

Ala Ser Leu Glu His Leu Gln Lys Arg Met Cys Gly Gly Pro Ala Ser
    385                 390                 395                 400

Ser Gly Ser Thr Ser
                    405

<210>   55
<211>   391
<212>   PRT
<213>   Hordeum vulgare

<400>   55

Met Glu Arg Val Phe Ser Val Glu Glu Ile Pro Asp Pro Phe Trp Gly
1               5                   10                  15

Gln Pro Ser Pro Arg Gln Arg Gly Arg Arg Pro Pro Glu Gly Ala Met
            20                  25                  30

Asn Arg Cys Pro Ser Glu Trp Tyr Phe Gln Lys Phe Leu Glu Glu Ala
        35                  40                  45

Val Leu Asp Ser Pro Ala Ala Asp Pro Ser Pro Met Ser Gly Ala Ser
    50                  55                  60

Gly Arg Gly Gln Ala Ala Cys Arg Pro Arg Gly Val Ala Gly Thr Ala
65                  70                  75                  80

Thr Gly Pro Ala Val Asp Pro Val Glu Tyr Asn Ala Met Leu Lys Gln
                85                  90                  95

Lys Leu Glu Lys Asp Leu Ala Ala Val Ala Met Trp Arg Ala Ser Gly
            100                 105                 110

Ala Met Pro Pro Glu Arg Phe Ala Ala Ser Pro Ser Cys Pro Asn Ala
        115                 120                 125

Asp Gly Gln His Ile Gly Thr Ile Asn Pro Ile Gly Gly Asn Val Val
    130                 135                 140
```

```
Pro Leu Gln Asn Lys Leu Ala Gly Gly Ala Ser Gly Val Ser Gly Pro
145                 150                 155                 160

His Leu Val Gln Asn Ala Asp Ala Leu Val Lys Gln Ala Ala Ser Ser
                165                 170                 175

Ser Ser Arg Glu Gln Ser Glu Asp Asp Met Glu Gly Glu Asp Glu
            180                 185                 190

Ile Thr Gly Asn Gly Val Pro Thr Asp Gln Arg Leu Arg Arg Arg Lys
            195                 200                 205

Gln Ser Asn Arg Glu Ser Ala Arg Arg Ser Arg Ser Arg Lys Ala Ala
            210                 215                 220

His Leu Asn Glu Leu Glu Ala Gln Val Ser Gln Leu Arg Val Glu Asn
225                 230                 235                 240

Ser Ser Leu Leu Arg Arg Leu Ala Asp Val Asn Gln Lys Tyr Asn Gly
                245                 250                 255

Ala Ala Val Asp Asn Arg Val Leu Lys Ala Asp Val Glu Thr Leu Arg
                260                 265                 270

Ala Lys Val Lys Met Ala Glu Asp Ser Val Lys Arg Val Thr Gly Met
            275                 280                 285

Ser Ala Leu Phe Pro Ala Gly Ser Asp Met Ser Ser Leu Ser Met Pro
    290                 295                 300

Phe Thr Gly Ser Pro Ser Glu Ala Thr Ser Asp Ala Ala Phe Pro Asp
305                 310                 315                 320

Asp Leu Ser Ala Tyr Phe Ser Thr Ser Glu Ala Gly Gly Asn Asn Gly
                325                 330                 335

Tyr Met Pro Glu Met Ala Ser Ser Ala Gln Glu Asp Asp Asn Phe Leu
            340                 345                 350

Asn Glu Thr Met Asp Thr Ser Lys Met Gly Arg Pro Asp Ser Leu His
            355                 360                 365
```

```
Arg Val Ala Ser Leu Glu His Leu Gln Lys Arg Met Cys Gly Gly Pro
    370                 375                 380

Ala Ser Ser Gly Ser Thr Ser
385                 390

<210>  56
<211>  409
<212>  PRT
<213>  Triticum aestivum

<400>  56

Met Glu Pro Val Phe Phe Ser Leu Glu Glu Ala Met Pro Glu Pro Asp
1               5                   10                  15

Ser Asn Pro Cys Arg Thr Ser Ser Pro Leu Glu Ala His Met Leu
            20                  25                  30

Val Ala Gly Leu Gly Gly Val Gly Ala Gly Glu Val Val Gly Gly Cys
            35                  40                  45

Ala Thr Asn Glu Cys Ala Thr Glu Trp Cys Phe Gln Lys Phe Val Asp
    50                  55                  60

Glu Pro Trp Leu Leu Asn Val Pro Thr Ala Pro Val Ala Asn Pro Glu
65                  70                  75                  80

Ala Ser Thr Leu Tyr Pro Asn Pro Thr Ala Glu Gly Ser Arg Lys Arg
                85                  90                  95

Pro Tyr Asp Val His Glu Met Val Gly Pro Glu Glu Val Ile Pro Thr
            100                 105                 110

Pro Pro Ala Ala Ser Pro Val Val Asp Pro Val Ala Tyr Asn Ala Met
            115                 120                 125

Leu Arg Arg Lys Leu Asp Ala His Leu Ala Ala Val Ala Met Leu Arg
    130                 135                 140

Thr Thr Arg Gly Ile Cys Pro Gln Ser Ser His Asp Asn Gly Ala Ser
145                 150                 155                 160

Gln Asn Ser Asp Ser Ile Gln Gly Ser Glu Asn His Thr Gly Asp Val
                165                 170                 175
```

```
Ser Leu His Gln Leu Ser Ser Ser Leu Glu Pro Ser Pro Ser Asp
            180             185             190
Gly Asp Met Glu Gly Glu Ala Gln Thr Ile Gly Thr Met His Ile Ser
            195             200             205
Ala Glu Lys Ala Asn Lys Arg Lys Glu Ser Asn Arg Asp Ser Ala Arg
210             215             220
Arg Ser Arg Ser Arg Lys Ala Ala His Ala Lys Glu Leu Glu Glu Gln
225             230             235             240
Val Ser Leu Leu Arg Val Ala Asn Asn Ser Leu Met Arg His Leu Ala
            245             250             255
Asp Val Ser His Arg Tyr Val Asn Ile Ser Ile Asp Asn Arg Val Leu
            260             265             270
Lys Ala Asn Val Glu Thr Leu Glu Ala Lys Val Lys Met Ala Glu Glu
            275             280             285
Thr Met Lys Arg Val Thr Cys Thr Asn Asn Phe Pro Gln Ala Met Ser
            290             295             300
Ser Ile Ser Ser Leu Gly Ile Pro Phe Ser Gly Ser Pro Leu Asn Gly
305             310             315             320
Ile Cys Asp Asn Pro Leu Pro Thr Gln Asn Thr Ser Leu Asn Tyr Leu
            325             330             335
Pro Pro Thr Thr Thr Asn Phe Asp Val Asn Asn Tyr Ile Pro Glu
            340             345             350
Pro Ala Leu Ala Phe Gln Ile Gln Asp Gln Ile Pro Ser Leu His Met
            355             360             365
Gln Pro Met Ser Cys Leu Asp His His Pro Gln Arg Met His Ile Gly
            370             375             380
```

```
Ile Pro Thr Ser Ala Pro Thr Pro Gln Arg Glu Ser Thr Thr Leu Asp
385                 390                 395                 400

Ser Thr Glu Ile Val Asn Met Val Met
                405
```

<210> 57
<211> 409
<212> PRT
<213> Hordeum vulgare

<400> 57

```
Met Glu Pro Val Phe Ser Leu Leu Glu Glu Ala Met Pro Glu Pro Asp
1               5                   10                  15

Ser Asn Pro Gly Arg Thr Ser Pro Pro Gln Leu Gln Ala His Val Leu
                20                  25                  30

Ala Gly Gly Val Arg Gly Ala Gly Gly Val Gly Val Gly Glu Ile Val
            35                  40                  45

Gly Asp Gly Ala Thr Glu Leu Cys Phe Asp Lys Ser Met Glu Glu Pro
50                  55                  60

Ser Leu Leu Asn Val Pro Thr Glu Pro Val Ala Asn Pro Asp Ala Ser
65                  70                  75                  80

Thr Leu His Pro Asn Pro Thr Ala Glu Val Ser Arg Lys Arg Arg Tyr
                85                  90                  95

Asp Val His Glu Glu Glu Val Val Gly Val Ile Pro Thr Pro Pro
            100                 105                 110

Ala Ala Gly Ala Val Leu Asp Pro Val Gly Tyr Asn Ala Met Leu Arg
            115                 120                 125

Arg Lys Leu Asp Ala His Leu Ala Ala Val Ala Met Trp Arg Thr Thr
        130                 135                 140

Arg Gly Ile Cys Arg Gln Ser Ser His Asp Arg Ala Ser Gln Asn
145                 150                 155                 160

Pro Asp Ser Ile Gln Gly Ser Glu Asn His Thr Gly Asp Ala Ser Val
                165                 170                 175
```

```
Gln Gln Leu Ser Ser Ser Ser Trp Glu Pro Ser Pro Ser Asp Asp Asp
            180                 185                 190

Met Glu Gly Glu Ala Gln Thr Ile Gly Thr Met Asn Ile Ser Ala Glu
            195                 200                 205

Lys Val Asn Lys Arg Lys Glu Ser Asn Arg Asp Ser Ala Arg Arg Ser
    210                 215                 220

Arg Ser Arg Lys Ala Ala His Thr Lys Glu Leu Glu Glu Gln Val Ser
225                 230                 235                 240

Leu Leu Arg Val Ala Asn Asn Ser Leu Met Arg His Leu Ala Asp Val
                245                 250                 255

Ser His Arg Tyr Val Asn Thr Ala Ile Asp Asn Arg Val Leu Lys Ala
                260                 265                 270

Asn Val Glu Thr Leu Glu Ala Lys Val Lys Met Ala Glu Glu Thr Met
            275                 280                 285

Lys Arg Ile Thr Ser Thr Asn Asn Phe Pro Gln Ala Ile Ser Gly Met
290                 295                 300

Ser Ser Leu Arg Thr His Phe Ser Gly Ser Gln Leu Asp Gly Ile Phe
305                 310                 315                 320

Asp Thr Thr Leu Pro Thr Gln Asn Met Ser Leu Asn His Phe Ser Thr
                325                 330                 335

Thr Ala Thr Asn Phe Asp Val Ser Ser Asn Tyr Ile Pro Glu Leu Ala
            340                 345                 350

Pro Ala Tyr Gln Ile His Asp Gln Ile Ser Ser Leu His Thr Gln Pro
            355                 360                 365

Met Pro Cys Leu Asp His His Pro Arg Arg Met Pro Phe Gly Ile Pro
370                 375                 380
```

```
Ser Thr Leu Val Pro Thr Pro Gln Arg Glu Ser Thr Thr Leu Asp Ser
385                 390                 395                 400

Asn Glu Ile Gly Asn Met Val Met Gln
                405
```

<210> 58
<211> 419
<212> PRT
<213> Sorghum bicolor

<400> 58

```
Met Glu Pro Val Phe Ser Met Glu Glu Ile Leu Gly Pro Phe Trp Asp
1               5                   10                  15

Leu Pro Ser Pro Pro Pro Glu Gln Gln Pro Leu Val Ile Gly Thr
                20                  25                  30

Ser Ser Val Val Ile Asp Gly Val Val Thr His Gly Gly Asn Gly Glu
            35                  40                  45

Gly Ser Asn Met Met Asp Gln Ile Gln Asn Thr Thr Glu Trp Thr Phe
    50                  55                  60

Glu Arg Leu Leu Glu Glu Leu Leu Thr Asp Thr Thr Pro Val Ala
65                  70                  75                  80

Asn Ser Ser Cys Pro Ala Leu Asn Val Asp Pro Val Val Glu Val Asp
                85                  90                  95

Gln Gly Ala Met Ala Pro Glu Ala Val Ser Ala Val Gly Asp Pro Met
                100                 105                 110

Glu Tyr Asn Ala Ile Leu Lys Arg Asn Val Glu Glu Asp Leu Met Ala
            115                 120                 125

Phe Lys Met Trp Arg Ala Ser Thr Ser Gly Val Asn Ser Glu Gly Ser
            130                 135                 140

Asn Asn Glu Asn Gly Gly Val Ser Ser Ser Lys Asn Leu Val Gln Thr
145                 150                 155                 160

Lys Leu Asn Gly Glu Asp Leu Ile Asn Asn His Ala Gln Asn Ala Asp
                165                 170                 175
```

```
Leu His Val Arg Leu Thr Thr Ser Ser Ser Arg Asp Pro Ser Pro
            180                 185                 190

Ser Asp Glu Asp Met Asp Gly Glu Val Glu Ile Leu Gly Phe Lys Met
        195                 200                 205

Pro Thr Glu Glu Arg Val Arg Lys Arg Lys Glu Ser Asn Arg Glu Ser
    210                 215                 220

Ala Arg Arg Ser Arg Tyr Arg Lys Ala Ala His Leu Lys Asp Leu Glu
225                 230                 235                 240

Asp Gln Val Asp Lys Leu Lys Ala Glu Asn Ser Cys Leu Leu Arg Arg
            245                 250                 255

Leu Ala Ala Leu Asn Gln Lys Tyr Asn His Ala Thr Val Asp Asn Arg
            260                 265                 270

Val Leu Lys Ala Asp Met Glu Thr Leu Arg Ala Lys Val Lys Met Gly
        275                 280                 285

Glu Asp Ser Leu Lys Arg Ile Ile Glu Met Thr Ser Leu Thr Ser Ile
    290                 295                 300

Pro Ile Pro Glu Leu Pro Ser Ser Ser Asp Val Pro Val His Ile Gln
305                 310                 315                 320

Asp Asn Ile Val Asn Tyr Phe Thr Thr Pro Ala Gly Asp Ala Leu
            325                 330                 335

Ala Asp Asn Ser Phe Met Pro Met Pro Asp Pro Leu Pro Leu Gln Leu
            340                 345                 350

Gln Ala Glu Glu Pro Thr Ile Asn Gly Ala Leu Asn Ala Thr Glu Met
        355                 360                 365

Asn Gln Ile Ala Thr His Cys Ala Ala Gly Ser Gln Pro Ser Met Gln
        370                 375                 380

Leu Ile Gln Glu Thr Met Gly Ala Met Met Pro Thr Ser Ser Gly Ser
385                 390                 395                 400
```

Thr Leu Gln Glu Ser Glu Leu Leu Gly Pro Asn Glu Thr Ile Asn Met
            405                 410                 415

His Met Tyr

<210> 59
<211> 408
<212> PRT
<213> Coix lacryma-jobi

<400> 59

Met Glu His Val Ile Ser Met Glu Glu Ile Leu Gly Pro Phe Trp Asp
1               5                   10                  15

Leu Pro Pro Ser Pro Pro Leu Pro Leu Pro Glu Gln Gln Pro Leu
            20                  25                  30

Val Thr Asp Thr Gly Ser Val Val Ile Asp Gly Val Thr Gln Gly
            35                  40                  45

Gly Gly Asp Gly Glu Gly Gly Asp Met Met Gly Gln Asn Thr Thr Glu
    50                  55                  60

Trp Thr Phe Glu Arg Leu Leu Glu Glu Ile Leu Ile Asn Lys Thr
65                  70                  75                  80

Thr Leu Val Thr Asn Ser Ser Cys Ser Thr Leu Asn Ile Asp Pro Val
                85                  90                  95

Val Glu Val Asp Gln Gly Thr Met Ala Ser Gly Ala Val Ser Ala Val
                100                 105                 110

Gly Asp Pro Met Glu Tyr Asn Ala Ile Leu Lys Arg Lys Leu Glu Val
            115                 120                 125

Asp Leu Val Ala Phe Lys Met Trp Arg Ala Ser Ser Val Val Asn Ser
130                 135                 140

Glu Arg Ser Gln Asp Ser Asn Asn His Asn Gly Gly Ser Lys Asn Val
145                 150                 155                 160

Val Gln Asn Lys Leu Asn Gly Glu Asp Pro Ile Asn Asn His Ala Gln
                165                 170                 175

```
Asn Val Asp Leu Arg Val Arg Leu Ala Thr Ser Ser Ser Ser Arg Asp
            180                 185                 190

Pro Ser Pro Ser Asp Glu Asp Met Asp Gly Glu Val Glu Ile Leu Gly
            195                 200                 205

Phe Lys Met Pro Thr Glu Glu Arg Val Arg Lys Arg Lys Glu Ser Asn
210                 215                 220

Arg Glu Ser Ala Arg Arg Ser Arg Tyr Arg Lys Ala Ala His Leu Lys
225                 230                 235                 240

Glu Leu Glu Asp Gln Val Glu Gln Leu Lys Ala Glu Asn Ser Cys Leu
            245                 250                 255

Leu Arg Arg Leu Ala Ala Leu Asn Gln Lys Tyr Asn Glu Ala Asn Val
            260                 265                 270

Asp Asn Arg Val Leu Arg Ala Asp Met Glu Thr Leu Arg Ala Lys Val
            275                 280                 285

Lys Met Gly Glu Asp Ser Leu Lys Arg Val Met Glu Met Ser Ser Leu
290                 295                 300

Pro Pro Ser Met Pro Ile Pro Ala Leu Pro Ser Ser Asp Ala Ser
305                 310                 315                 320

Val Pro Ile Gln Asp Asp Ile Ile Asn Tyr Phe Ser Thr Thr Pro Ala
            325                 330                 335

Ala Asp Glu Asp Ala Pro Val Asp Asn Asn Ser Phe Ile Ile Met Pro
            340                 345                 350

Met Ala Asp Pro Leu Gln Leu Val Gln Ala Glu Asp Gln Pro Thr Met
            355                 360                 365

Gly Ala Met Glu Leu Ile Gln Lys Thr Met Gly Ala Met Pro Thr Ser
370                 375                 380
```

```
Pro Gly Ser Ala Leu Gln Glu Ser Gln Leu Leu Gly Leu Gly Pro Asp
385                 390                 395                 400

Glu Thr Ile Asn Met Asp Met Tyr
                405
```

<210> 60
<211> 437
<212> PRT
<213> Zea mays

<400> 60

```
Met Glu His Val Ile Ser Met Glu Glu Ile Leu Gly Pro Phe Trp Glu
1               5                   10                  15

Leu Leu Pro Pro Pro Ala Pro Glu Pro Glu Arg Glu Gln Pro Pro Val
                20                  25                  30

Thr Gly Ile Val Val Gly Ser Val Ile Asp Val Ala Ala Ala Gly His
            35                  40                  45

Gly Asp Gly Asp Met Met Asp Gln Gln His Ala Thr Glu Trp Thr Phe
    50                  55                  60

Glu Arg Leu Leu Glu Glu Glu Ala Leu Thr Thr Ser Thr Pro Pro Pro
65                  70                  75                  80

Val Val Val Val Pro Asn Ser Cys Cys Ser Gly Ala Leu Asn Ala Asp
                    85                  90                  95

Arg Pro Pro Val Met Glu Glu Ala Val Thr Met Ala Pro Ala Ala Val
                100                 105                 110

Ser Ser Ala Val Val Gly Asp Pro Met Glu Tyr Asn Ala Ile Leu Arg
            115                 120                 125

Arg Lys Leu Glu Glu Asp Leu Glu Ala Phe Lys Met Trp Arg Ala Ala
        130                 135                 140

Ser Ser Val Val Thr Ser Asp Gln Arg Ser Gln Gly Ser Asn Asn His
145                 150                 155                 160

Thr Gly Gly Ser Ser Ile Arg Asn Asn Pro Val Gln Asn Lys Leu Met
                165                 170                 175
```

Asn Gly Glu Asp Pro Ile Asn Asn His Ala Gln Thr Ala Gly Leu
            180                 185                 190

Gly Val Arg Leu Ala Thr Ser Ser Ser Arg Asp Pro Ser Pro Ser
        195                 200                 205

Asp Glu Asp Met Asp Gly Glu Val Glu Ile Leu Gly Phe Lys Met Pro
210                 215                 220

Thr Glu Glu Arg Val Arg Lys Arg Lys Glu Ser Asn Arg Glu Ser Ala
225                 230                 235                 240

Arg Arg Ser Arg Tyr Arg Lys Ala Ala His Leu Lys Glu Leu Glu Asp
                245                 250                 255

Gln Val Ala Gln Leu Lys Ala Glu Asn Ser Cys Leu Leu Arg Arg Ile
            260                 265                 270

Ala Ala Leu Asn Gln Lys Tyr Asn Asp Ala Asn Val Asp Asn Arg Val
        275                 280                 285

Leu Arg Ala Asp Met Glu Thr Leu Arg Ala Lys Val Lys Met Gly Glu
290                 295                 300

Asp Ser Leu Lys Arg Val Ile Glu Met Ser Ser Ser Val Pro Ser Ser
305                 310                 315                 320

Met Pro Ile Ser Ala Pro Thr Pro Ser Ser Asp Ala Pro Val Pro Pro
            325                 330                 335

Pro Pro Ile Arg Asp Ser Ile Val Gly Tyr Phe Ser Ala Thr Ala Ala
        340                 345                 350

Asp Asp Asp Ala Ser Val Gly Asn Gly Phe Leu Arg Leu Gln Ala His
        355                 360                 365

Gln Glu Pro Ala Ser Met Val Val Gly Gly Thr Leu Ser Ala Thr Glu
370                 375                 380

```
Met Asn Arg Val Ala Ala Thr His Cys Ala Gly Ala Met Glu His
385                 390                 395                 400

Ile Gln Thr Ala Met Gly Ser Met Pro Pro Thr Ser Ala Ser Gly Ser
                405                 410                 415

Thr Pro Pro Pro Gln Asp Tyr Glu Leu Leu Gly Pro Asn Gly Ala Ile
            420                 425                 430

His Met Asp Met Tyr
            435

<210> 61
<211> 298
<212> PRT
<213> Oryza sativa

<400> 61

Met Lys Lys Cys Pro Ser Glu Leu Asn Phe Glu Ala Phe Phe His Gly
1               5                   10                  15

Glu Arg Gly Glu Asp Asp Ala Asp Ala Ala Asp Gln Lys Pro Gly
            20                  25                  30

Gly Gly Pro His Pro Pro Pro Phe Ala Met Phe Ser Ala Ala Asp Leu
            35                  40                  45

Ser Ser Phe Gly Phe Ala Asp Ser Val Thr Ser Thr Ile Thr Gly Val
        50                  55                  60

Ile Pro Asn His Ile Trp Pro Gln Ser Gln Ser Leu Asn Ala Arg His
65                  70                  75                  80

Pro Ala Val Tyr Thr Ile Glu Ser Gln Ser Ser Ile Cys Ala Ala Ala
                85                  90                  95

Ser Pro Thr Ser Ala Thr Thr Leu Asn Met Lys Glu Ser Gln Thr Leu
            100                 105                 110

Gly Gly Thr Ser Gly Ser Asp Ser Asp Ser Glu Ser Leu Leu Asp Ile
            115                 120                 125

Glu Gly Gly Pro Cys Glu Gln Ser Thr Asn Pro Leu Asp Val Lys Arg
        130                 135                 140
```

```
Met Arg Arg Met Val Ser Asn Arg Glu Ser Ala Arg Arg Ser Arg Lys
145                 150                 155                 160

Arg Lys Gln Ala His Leu Ala Asp Leu Glu Thr Gln Val Asp Gln Leu
                165                 170                 175

Arg Gly Glu Asn Ala Ser Leu Phe Lys Gln Leu Thr Asp Ala Asn Gln
                180                 185                 190

Gln Phe Thr Thr Ala Val Thr Asp Asn Arg Ile Leu Lys Ser Asp Val
        195                 200                 205

Glu Ala Leu Arg Val Lys Val Lys Met Ala Glu Asp Met Val Ala Arg
    210                 215                 220

Gly Ala Leu Ser Cys Gly Leu Gly His Leu Gly Gly Leu Ser Pro Ala
225                 230                 235                 240

Leu Asn Pro Arg Gln Gly Ala Cys Arg Val Pro Asp Val Leu Thr Gly
                245                 250                 255

Leu Asp Tyr Ala Gly Asp Pro Phe Thr Gly Leu Ser Pro Pro Glu
            260                 265                 270

Gln Val Gln Met Pro Gly Gly Glu Val Gly Asp Ala Trp Gly Trp
        275                 280                 285

Asp Asn His Ser Asn Gly Ala Met Ser Lys
    290                 295

<210>  62
<211>  33
<212>  DNA
<213>  Oryza sativa

<400>  62
aagtttgtca tggctgagtc atgaaatgta tag                                    33

<210>  63
<211>  21
<212>  DNA
<213>  Oryza sativa

<400>  63
gggagtcatg gctgagtcat g                                                 21
```

```
<210>  64
<211>  21
<212>  DNA
<213>  Oryza sativa

<400>  64
gtttcggatg gctgagtcat g                                              21

<210>  65
<211>  21
<212>  DNA
<213>  Oryza sativa

<400>  65
gtttgtccgt gctgagtcat g                                              21

<210>  66
<211>  21
<212>  DNA
<213>  Oryza sativa

<400>  66
gtttgtcatg taagagtcat g                                              21

<210>  67
<211>  21
<212>  DNA
<213>  Oryza sativa

<400>  67
gtttgtcatg gcttcctcat g                                              21

<210>  68
<211>  21
<212>  DNA
<213>  Oryza sativa

<400>  68
gtttgtcatg gctgaggatt g                                              21

<210>  69
<211>  21
<212>  DNA
<213>  Oryza sativa

<400>  69
gtttgggctg gctgagaagt g                                              21

<210>  70
<211>  37
<212>  PRT
<213>  Oryza sativa
```

<400> 70

Met Glu His Val Phe Ala Val Asp Glu Ile Pro Asp Pro Leu Trp Ala
1               5                   10                  15

Pro Pro Pro Pro Val Gln Pro Ala Ala Ala Gly Val Asp Asp Val
            20                  25                  30

Gly Ala Val Ser Gly
        35

<210> 71
<211> 37
<212> PRT
<213> Oryza sativa

<400> 71

Met Glu Arg Val Phe Ala Val Asp Glu Ile Pro Asp Pro Leu Trp Ala
1               5                   10                  15

Pro Pro Pro Pro Val Gln Pro Ala Ala Ala Gly Val Asp Asp Val
            20                  25                  30

Gly Ala Val Ser Gly
        35

<210> 72
<211> 37
<212> PRT
<213> Oryza sativa

<400> 72

Met Glu His Val Phe Ser Val Asp Glu Ile Pro Asp Pro Leu Trp Ala
1               5                   10                  15

Pro Pro Pro Pro Val Gln Pro Ala Ala Ala Gly Val Asp Asp Val
            20                  25                  30

Gly Ala Val Ser Gly
        35

<210> 73
<211> 37
<212> PRT
<213> Oryza sativa

<400> 73

Met Glu His Val Phe Ala Val Glu Glu Ile Pro Asp Pro Leu Trp Ala
1               5                   10                  15

Pro Pro Pro Pro Val Gln Pro Ala Ala Ala Gly Val Asp Asp Val
                20                  25                  30

Gly Ala Val Ser Gly
            35

<210> 74
<211> 37
<212> PRT
<213> Oryza sativa

<400> 74

Met Glu His Val Phe Ala Val Asp Glu Ile Pro Asp Pro Leu Trp Ala
1               5                   10                  15

Pro Pro Pro Pro Val Gln Pro Ala Ala Ala Gly Val Asp Asp Val
                20                  25                  30

Gly Ala Val Ser Gly
            35

<210> 75
<211> 37
<212> PRT
<213> Oryza sativa

<400> 75

Met Glu His Val Phe Ala Val Asp Glu Ile Pro Asp Pro Phe Trp Ala
1               5                   10                  15

Pro Pro Pro Pro Val Gln Pro Ala Ala Ala Gly Val Asp Asp Val
                20                  25                  30

Gly Ala Val Ser Gly
            35

<210> 76
<211> 37
<212> PRT
<213> Oryza sativa

<400> 76

Met Glu His Val Phe Ala Val Asp Glu Ile Pro Asp Pro Leu Trp Val
1               5                   10                  15

Pro Pro Pro Val Gln Pro Ala Ala Ala Gly Val Asp Asp Val
            20                  25                  30

Gly Ala Val Ser Gly
            35

<210> 77
<211> 37
<212> PRT
<213> Oryza sativa

<400> 77

Met Glu His Val Phe Ala Val Asp Glu Ile Pro Asp Pro Leu Trp Ala
1               5                   10                  15

Pro Pro Pro Pro Gln Pro Ala Ala Ala Gly Val Asp Asp Val
            20                  25                  30

Gly Ala Val Ser Gly
            35

<210> 78
<211> 37
<212> PRT
<213> Oryza sativa

<400> 78

Met Glu His Val Phe Ala Val Asp Glu Ile Pro Asp Pro Leu Trp Ala
1               5                   10                  15

Pro Pro Pro Pro Val Gln Ser Ala Ala Ala Gly Val Asp Asp Val
            20                  25                  30

Gly Ala Val Ser Gly
            35

```
<210>  79
<211>  12
<212>  DNA
<213>  Oryza sativa

<400>  79
agccacgtgg ca                                                    12

<210>  80
<211>  12
<212>  DNA
<213>  Oryza sativa

<400>  80
acctacgtag ga                                                    12

<210>  81
<211>  12
<212>  DNA
<213>  Oryza sativa

<400>  81
agtgacgtca ca                                                    12

<210>  82
<211>  12
<212>  DNA
<213>  Oryza sativa

<400>  82
aggtacgtgg ca                                                    12

<210>  83
<211>  12
<212>  DNA
<213>  Oryza sativa

<400>  83
actgacgtaa ga                                                    12

<210>  84
<211>  12
<212>  DNA
<213>  Oryza sativa

<400>  84
ttccacgtag at                                                    12
```

```
<210>  85
<211>  12
<212>  DNA
<213>  Oryza sativa

<400>  85
gatgacatgg ct                                                              12

<210>  86
<211>  7
<212>  DNA
<213>  Oryza sativa

<400>  86
tgacaca                                                                     7

<210>  87
<211>  9
<212>  DNA
<213>  Oryza sativa

<400>  87
gatgactca                                                                   9

<210>  88
<211>  8
<212>  DNA
<213>  Oryza sativa

<400>  88
tgactcac                                                                    8

<210>  89
<211>  8
<212>  DNA
<213>  Oryza sativa

<400>  89
ggtgacac                                                                    8

<210>  90
<211>  9
<212>  DNA
<213>  Oryza sativa

<400>  90
gtatgtggc                                                                   9
```

```
<210>  91
<211>  12
<212>  DNA
<213>  Oryza sativa

<400>  91
gatccatgtc ac                                                        12
```